(12) United States Patent
Mohanty et al.

(10) Patent No.: US 12,040,164 B2
(45) Date of Patent: Jul. 16, 2024

(54) FREE RADICAL GENERATION DEVICE AND METHODS THEREOF

(71) Applicant: Somnio Global Holdings, LLC, Novi, MI (US)

(72) Inventors: Pravansu S. Mohanty, Canton, MI (US); Volodymyr Ivanovich Golota, Novi, MI (US); Tejasvi Chunduri, Ann Arbor, MI (US); Raj Siman Swamy Naidu Ugapathy, Novi, MI (US); Vigneswaran Hirachand Appia, Novi, MI (US); Vikram Varadaraajan, Novi, MI (US)

(73) Assignee: Somnio Global Holdings, LLC, Farmington Hills, MI (US)

( * ) Notice: Subject to any disclaimer, the term of this patent is extended or adjusted under 35 U.S.C. 154(b) by 53 days.

(21) Appl. No.: 17/727,285

(22) Filed: Apr. 22, 2022

(65) Prior Publication Data

US 2022/0246405 A1 Aug. 4, 2022

Related U.S. Application Data

(63) Continuation of application No. 16/327,647, filed as application No. PCT/US2017/050087 on Sep. 5, 2017, now abandoned.
(Continued)

(51) Int. Cl.
*H01J 37/32* (2006.01)
*A61L 2/20* (2006.01)
(Continued)

(52) U.S. Cl.
CPC .......... *H01J 37/32541* (2013.01); *A61L 2/20* (2013.01); *A61L 2/26* (2013.01); *C02F 1/4608* (2013.01);
(Continued)

(58) Field of Classification Search
CPC ............... H01J 37/32541; H01J 37/24; H01J 37/32449; H01J 37/32018;
(Continued)

(56) References Cited

U.S. PATENT DOCUMENTS

| 6,103,190 A | 8/2000 | Tanimura et al. |
| 2005/0174062 A1 | 8/2005 | Tanaka et al. |

(Continued)

FOREIGN PATENT DOCUMENTS

| FR | 2775864 A1 | 9/1999 |
| JP | H11333244 A | 12/1999 |

(Continued)

OTHER PUBLICATIONS

Supplementary European Search Report and Search Opinion for EP Application No. 17847685.9, issued on Apr. 14, 2020.

*Primary Examiner* — Xiuyu Tai
(74) *Attorney, Agent, or Firm* — Weston R. Gould; Dinsmore & Shohl, LLP

(57) ABSTRACT

A barrierless device and method for generating streamer discharge is provided including solid/liquid electrodes for free radical generation at high efficiency. A first electrode, including periodically positioned discharge ignition tips is deposed in proximity to a second electrode, creating a discharge gap with no dielectric barrier layer in between. The discharge gap includes an inlet and an outlet. Streamers with proximity constraints emerge from the first electrode and propagate through the discharge gap towards the second electrode by supplying either positive or negative pulse voltage to the first electrode, resulting in interaction of the streamer heads with the discharge gas and generation of radicals. Optionally, the second electrode is a liquid which interacts with the streamer head to generate additional radicals. The device can either be used to cause fast chemical (Continued)

reaction within the discharge gap or the generated radical gas can be removed for utilization outside the discharge gap.

19 Claims, 58 Drawing Sheets

Related U.S. Application Data

(60) Provisional application No. 62/383,046, filed on Sep. 2, 2016.

(51) Int. Cl.
  *A61L 2/26* (2006.01)
  *C02F 1/46* (2023.01)
  *H01J 37/24* (2006.01)
  *H05H 1/24* (2006.01)

(52) U.S. Cl.
  CPC ........ *H01J 37/24* (2013.01); *H01J 37/32449* (2013.01); *C02F 2303/04* (2013.01); *H05H 1/471* (2021.05)

(58) Field of Classification Search
  CPC ........... H01J 37/32027; H01J 37/32844; H01J 37/32568; A61L 2/20; A61L 2/26; A61L 2/14; A61L 2202/11; A61L 2202/21; A61L 2/202; A61L 2/0094; C02F 1/4608; C02F 2303/04; H05H 1/471; H05H 2245/36; H05H 1/4697; H05H 7/20; B01J 19/08; B01J 19/088; B01J 2219/0898; B01J 2219/0875; Y02C 20/30; B01D 2259/818; B01D 2259/4508; B01D 2258/06
  See application file for complete search history.

(56) References Cited

U.S. PATENT DOCUMENTS

| | | |
|---|---|---|
| 2007/0123422 A1 | 5/2007 | Steffen |
| 2010/0247403 A1 | 9/2010 | Hancock |
| 2011/0101862 A1 | 5/2011 | Koo et al. |
| 2011/0284437 A1 | 11/2011 | Johnson |
| 2011/0296996 A1 | 12/2011 | Gao et al. |
| 2012/0284950 A1 | 11/2012 | De Wit et al. |
| 2013/0012006 A1 | 1/2013 | Yamazaki et al. |
| 2015/0179411 A1 | 6/2015 | Laux et al. |
| 2017/0018410 A1* | 1/2017 | Laux ................. H01J 37/32541 |
| 2017/0081221 A1* | 3/2017 | Namihira ................. B03C 1/02 |

FOREIGN PATENT DOCUMENTS

| | | |
|---|---|---|
| JP | 2001321633 A | 11/2001 |
| JP | 2004000960 A | 1/2004 |
| JP | 2005116202 A | 4/2005 |
| JP | 2012089314 A | 5/2012 |
| KR | 10-1173641 B1 | 8/2012 |
| WO | 2004/026461 A1 | 4/2004 |

\* cited by examiner

FIG. 54

FREE RADICAL GENERATION DEVICE AND METHODS THEREOF

CROSS REFERENCE TO RELATED APPLICATIONS

This application is a continuation of U.S. application Ser. No. 16/327,647 filed Feb. 22, 2019, which is a U.S. National Stage under 35 U.S.C. § 371 of PCT/US2017/050087 filed Sep. 5, 2017, and depends from and claims priority to U.S. Provisional Application No. 62/383,046 filed Sep. 2, 2016, the entire contents of each of which are incorporated by reference herein.

TECHNICAL FIELD

The present disclosure relates to a device and method for generating streamer discharge in a dielectric barrierless discharge space including solid/liquid electrodes and more particularly to methods for enhancing free radical generation and the associated physiochemical reaction(s), while minimizing arcing, electrode erosion and corrosion at high moisture content.

BACKGROUND

Electric discharge through air or molecular gases and the resulting radicals such as: $O^*$, $N^*$, $OH^*$, $H^*$, $CH_2^*$, etc., have many practical applications ranging from sterilization, thin film deposition, surface treatment, and pollutant removal from a gas streams.

The most predominant method of generating discharge in a gas is by the use of a dielectric barrier between two conductors and then applying a high voltage between the electrodes to cause discharge in the gap, which is commonly known as "silent discharge" in the art. At a sufficiently high voltage between the electrodes the discharge starts in the gas volume. It spreads out until it reaches the electrodes, but at the dielectric surface it builds up a space charge that cancels the applied electric field. At that moment the discharge stops.

An alternative method utilizes an asymmetric electrode pair without the use of a dielectric barrier between them. Streamer or filament type discharges initiate from regions with strong electric fields which exist at a surface of an electrode with high curvature (needle, wire etc.). After being formed, a streamer is able to propagate for a long distance even in space where the field is relatively weak. However, to prevent complete breakdown (arcing) in the discharge gap, high voltage short pulses are used to stop the discharge before it transitions into an arc. The most common electrodes used in practice for this purpose are point-to-plane and wire-in-cylinder geometries.

The dielectric barrier discharge method can achieve high radical densities in the discharge gas across a small discharge gaps. However, barrier discharge is quite complicated since it is a combination of a gas discharge and a surface discharge along the dielectric. Scaling the process for large gas flows with large discharge gap is difficult to achieve using this method. The relatively long time duration of the applied voltage leads to energy loss and heat generation. Cooling system requirement results in further energy loss. Further, the inevitable buildup of ambient dust and similar contaminants on electrode components makes the long term operation of such devices problematic. The buildup of dusty, sticky, corrosive film over time, leads to reduction in discharge, short circuiting, rendering the device useless. Therefore, filtered and processed gases are required for the operation these devices. To address the buildup issue, a device with removable dielectric barrier layer has been suggested, however, it is not an economical solution.

In contrast, streamer discharge devices utilizing an asymmetric electrode pair are easier to scale up particularly for large gas flows. Typically, the electric field required to ignite streamers in air like mixtures is about $10^2$ -$10^3$ kV·cm$^{-1}$. Such high fields can easily be generated by using sharp electrodes such as wire and pins, with a modest applied voltage that is orders of magnitude lower. The field enhancement in front of streamer head is high enough to ensure a positive net ionization coefficient. A streamer can be considered as a self-sustained ionization wave propagating in neutral gas, which is converted into low-temperature plasma behind the wave front, resulting in a channel like appearance. The interior of the streamer channel consists of a conducting plasma with roughly the same electron and ion densities. The self-induced electric field of the streamer head allows the streamer to continue propagating even into regions where the applied electric field is insufficient to ensure a positive net ionization, and hence gives the scalability to these devices.

As illustrated in FIG. 1 depending upon the polarity of the active electrode, i.e., electrode with highest curvature, the electrons travel in different directions. For cathode directed (CDS) or positive streamer the electrons travel in the opposite direction of the streamer and for anode directed (ADS) or negative streamer the electrons travel in the same direction as the streamer. There are differences between the shape, electrical characteristics and the velocity of these two types of streamers. In general, a higher field should be applied to create negative streamer.

The local electric field in the streamer head can be in the order of 200 kV·cm$^{-1}$ for an applied voltage pulse in the order of 20 kV·cm$^{-1}$. Although, the population of electrons with lower energy levels can be significantly higher than the ones with higher energy levels, nevertheless, there is a tail of highly energetic electrons (with energies in the vicinity of 12 eV or higher) to dissociate and ionize gas molecules. For reference, dissociation and ionization of $H_2O$ can be achieved with electron energies in the order of 5 eV, whereas ionization of nitrogen requires higher electron energies in the order of 10 eV and ionization of oxygen requires electron energies in the order of 7 eV. In summary, the streamer head is an effective radical generator.

While the streamer head can be an effective radical producer, the active ionization region of a single streamer head is of order of hundreds of micrometers and it propagates with velocities in the order of $10^6$ m/s. The generated radicals are very unstable with very short life and often disappear by collision with the untreated gas, thereby making the radical density low, especially if the radicals were to be used outside the discharge space.

Citing the complexity and difficulty of deploying densely arranged sharp discharge pins to increase the discharge area, U.S. Pat. No. 7,042,159 B2 taught the use of electrodes with conical angles of 30° to 90°. It is claimed that the streamer discharge is formed owing to small electric arcs caused continuously from the pointed portion of the discharge electrode to the counter electrode. Further, it is claimed that due to this specified electrode angle, the streamer from each electrode expands over a wider region overlapping the inter electrode space [FIG. 2 of U.S. Pat. No. 7,042,159 B2].

Arcing between the electrodes should be avoided because arcing generates heat resulting in loss of radicals and damages the electrodes. Yet further, streamers of same nature (either positive or negative) would repel each other due to their enhanced electric field at the head. It is not apparent how the teachings of U.S. Pat. No. 7,042,159 B2 can achieve overlapping streamers from the same polarity discharge pins. It is possible that streamers would split and branch out before reaching the counter electrode, especially, when the discharge gap is large and the neighboring streamer influence is weak due to large inter pin distance. Instability of the thin space charge layer in the streamer head also leads to splitting. The branching instability can be accelerated by electron density fluctuations in the lowly ionized region ahead of the streamer. Under these circumstances, the radical generation efficiency will be very low. It is to be noted that, the net ionization coefficient is nearly zero in the secondary streamers and hence their formation should be discouraged.

Further, when the gap between the discharge pins is large, a significant portion of the feed gas will not interact with the ionization front and pass through the inter-electrode gaps. Especially, when the process gas flow rate is high (required for many commercial processes), the effective fraction of the gas interacting with the ionization front would be low, resulting in very low radical density.

US Patent Application # 2016/0179411 A1 disclosed a device with both electrodes having pins to maintain glow discharge. Distinction must be made between glow discharge and streamer discharge, and glow discharge is typically produced at (order of 1mbar) low pressure. With increasing pressure, the glow discharge has the tendency to become unstable and constrict: a glow-to-spark transition occurs. Such device arrangements will be difficult to operate in streamer mode as streamers travel with velocities in the order of $10^6$ m/s and streamers of opposite polarity will attract each other leading to arcing if pins are connected to opposite polarity, and if pins are connected to same polarity the streamers will repel each other.

From the aforementioned it is apparent that generation of radicals with a high density and with high efficiency by streamer formation and their collision losses with untreated gas is not easily solved. As such, new methods and devices are needed for effective generation of radicals.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

It is highly desirable that a radical generator be capable of utilizing gases with high moisture content (for useful OH* radicals) as well as other gaseous compounds (for removal of impurities, e.g., $CH_4$, $C_2H_4$ etc.), generate discharge gas including high energy radicals (O*, N*) at high density and with high efficiency. Heretofore, radical generators have been extremely susceptible to moisture in the feed gas, as water vapor in the gas may cause unwanted arcing. Further, generating significant amount of energetic electrons at the streamer head is required for dissociation and ionization efficiency, and preventing radical loss due to collision with untreated gas failing to interact with the streamer head to maintain high radical density has been challenging.

Provided is a radical generator wherein the discharge pin includes features with a sharp curvature to ignite streamers at low applied voltage. Also, a plurality of ignition tips are optionally provided on each discharge pin to generate a plurality of streamers. Further, the discharge pins are optionally arranged such that streamer heads constrain themselves to reduce secondary branching. Yet further, the discharge pins lend themselves amenable to cost effective manufacturing and assembly.

In general, streamer volume doesn't play an important role on the species concentration. Further, branching instability increases as the diameter of the streamer increases during propagation and is a function of streamer length. Branching and generation of secondary streamers reduce radical generation efficiency, and hence should be avoided. For reference, the electric field at the heads of smaller radii (as in the case of positive) streamers is much more enhanced than on the larger radii (as in the case of negative) streamers. The smaller radii streamers also move faster. Since radical production efficiency is determined by the local electric field (via the electron energy), narrow and primary streamers may be promoted for high radical generation efficiency in large discharge gaps.

Streamers originating from the same polarity discharge pins are repelled by neighboring streamers. If constrained uniformly by the field of neighboring streamers, radius thinning as well as field enhancement will occur. Further, the generation of secondary streamers will be restricted, thereby enhancing radical generation efficiency. Therefore, streamer ignition tips should be optimally positioned such that the field proximity of the surrounding streamers constrain each streamer head to keep it narrow and stable, and thus, achieving further field enhancement without increasing the applied voltage, and a significant fraction of electrons can cause dissociation and ionization of gas molecules, and thereby producing large amount of radicals. However, care must be taken to prevent arcing due to speed increase.

Large amount of high energy radicals can cause fast chemical reactions with impurities and moisture resulting in corrosive products. To develop reliable discharge devices, both the discharge pin and the ground electrode should have good electrical conductivity, erosion and corrosion resistance.

To maximize the radical density and generation efficiency, restricting the gas flow through the inter pin gaps is a design objective. Most of the feed gas may optionally be directed to interact with streamer head leaving little untreated gas in the device that can lead to radical loss due to collision. Further, the residual charges at the ignition tips may be removed between successive streamers to prevent arcing. Also, the device may be operable at high relative humidity without condensation on the electrodes. In other words, the gas velocity at the ignition tips may be strong.

Provided are devices that solve one or more above problems optionally by providing in at least one aspect a method for enhancing the interaction of the feed gas stream with the ionization front of the streamers, and thereby improving the efficiency of radical generation as well as their density. This includes increasing the number of primary streamers per unit volume, uniformity in their distribution in the flow path and hence increasing the interaction of the feed gas with higher number of energetic electrons capable of dissociation and ionization.

In some aspects, methods for self-constraining and directing the streamers are provided to increase the field enhancement at the streamer head as well as the number of energetic electrons for a given applied voltage. This optionally includes organizing discharge pins comprising a plurality of ignition tips on the discharge electrode assembly such that the streamers remain narrow due to the surrounding repulsive fields of the neighboring streamers, thereby, decreasing the probability of secondary streamer formation and increasing the probability that higher number of molecular dissociation events will occur due to the availability of higher number of energetics electrons inherent to the field enhancement effect at narrow streamer heads, and thus increasing the radical production efficiency as well as radical number density.

In yet other aspects, methods for selective radical generation are provided. This optionally includes narrowing the probability distribution of electrons with certain energy levels, due to streamer head modification by proximity field constraints of the neighboring streamers, and thereby providing the ability to generate a desired radical type compared to another, e.g., OH* vs N* in a gas mixture containing $H_2O$ and $N_2$.

In yet other aspects, manufacturing and assembly methods for the discharge pins are provided. This optionally includes organizing a plurality of substantially columnar discharge pins having a plurality of ignition tips on them, in a predetermined fashion providing uniform gap between the discharge pins as well as the ignition tips with high accuracy and density.

In other aspects, methods for preventing arcing between the discharge and counter electrodes are provided. This includes the application of a bias voltage to remove residual charges in the discharge gaps between successive voltage pulses. This ensures the same starting voltage for each pulse as applied to the discharge pins for streamer formation and prevents arcing between the electrodes.

In other aspects, methods for directing the feed gas through the discharge space are provided. This optionally includes a method for creating flow barrier between the discharge pins through their positioning which can be systematically organized and indexed with high accuracy and thereby providing high gas velocity around the discharge pins and enhancing radical production and reducing collision losses.

Accordingly, it becomes possible to solve the aforementioned problems and to generate radical gas at high density, selectivity and efficiency, which can either be utilized in the discharge space or supplied to an application site.

BRIEF DESCRIPTION OF THE DRAWINGS

The drawings are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention. Exemplary aspects will become more fully understood from the detailed description and the accompanying drawings, wherein:

FIG. 54 is an illustration showing possible mechanisms for toxin removal by free radicals from the discharge device disclosed here;

DETAILED DESCRIPTION

Figure 1:
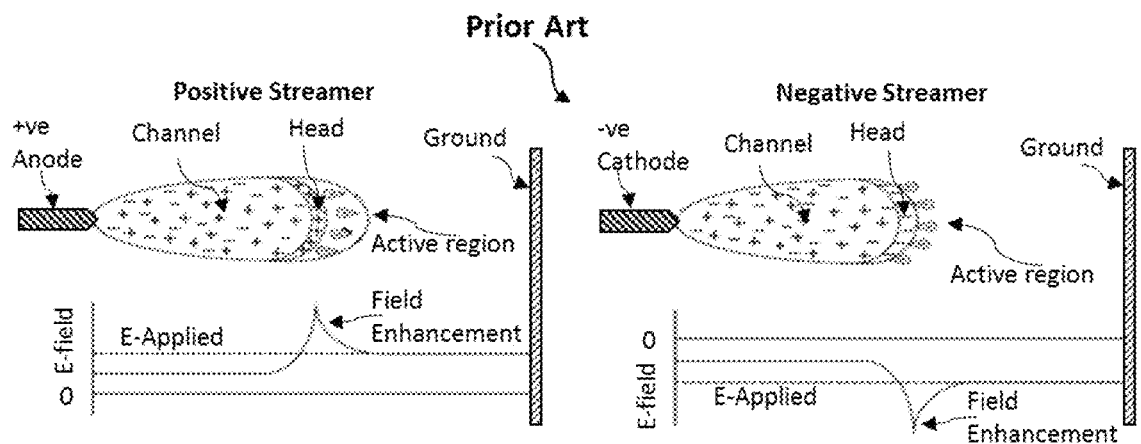
FIG. 1 is an exemplary schematic two dimensional illustration of positive and negative streamer propagation according to at least one known art.

Detailed aspects are disclosed herein; however, it is to be understood that the disclosed aspects are merely exemplary in nature and may be embodied in various and alternative forms. The figures are not necessarily to scale. Therefore, specific details disclosed herein are not to be interpreted as limiting, but merely as a representative basis for any aspect of the invention and/or as a representative basis for teaching one skilled in the art to variously employ the present invention.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Throughout this specification, where publications are referenced the disclosures of these publications in their entireties are hereby incorporated by reference into this application to more fully describe the state of the art to which this invention pertains.

The following terms or phrases used herein have the exemplary meanings listed below in connection with at least one aspect:

A "dielectric" material as used herein is a medium or material that transmits electrical force without conduction and as such has low electrical conductivity. An illustrative example of a dielectric material is glass.

"Discharge space" as used herein means the gap between the active electrode and the ground electrode.

"FRG" as used herein means "Free Radical Generator" operating according to the teachings of this disclosure.

"Carbonaceous material" as used herein includes graphite, woven carbon or graphite fiber filled with binders, graphitized carbon materials, and compacted carbon materials, among others.

"Mist" as used herein includes a cloud of tiny droplets of a liquid suspended in a gas wherein droplet weight is lower than the drag force exerted by the gas.

"Fumigation" as used herein includes applying a gaseous fume of certain radicals to disinfect or to rid of biological organisms or toxins.

"Superbugs" as used herein includes a strain of bacteria that has become resistant to one or more antibiotic drugs.

"Toxins" as used herein includes an antigenic poison or venom of plant or animal origin, optionally one produced by or derived from microorganisms and causing disease when present at low concentration in the body.

"Streamer" means a self-sustained ionization wave having substantial field enhancement in the range of 100-250 $kV \cdot cm^{-1}$ and propagating in neutral gas which is converted into low-temperature plasma behind the wave front, resulting in a channel like appearance. The interior of the streamer channel consists of a conducting plasma with roughly the same electron and ion densities.

"Free radical" means an atom or group of atoms that has an unpaired valence electron and is therefore unstable and highly reactive as those terms are recognized in the art. For example, free oxygen radicals are produced by following inelastic electron collisions:

$$O_2 + e^- \rightarrow O^+ + O + 2e^- \quad (1)$$

$$O_2 + e^- \rightarrow O + O + e^- \quad (2)$$

$$O_2 + e^- \rightarrow O^- + O \quad (3)$$

which are expressed in a generic form as: $O_2 + e^- \rightarrow O^* + O^*$. Other radicals may be produced by similar inelastic collisions depending upon the composition of the gas in the discharge space, such as:

$$H_2O + e^- \rightarrow OH^* + H^* \quad (4)$$

$$N_2 + e^- \rightarrow N^* + N^*. \quad (5)$$

"Field" means the electric field, which can be positive or negative in nature. Similar fields repel each other and opposite fields attract each other.

Figure 2:
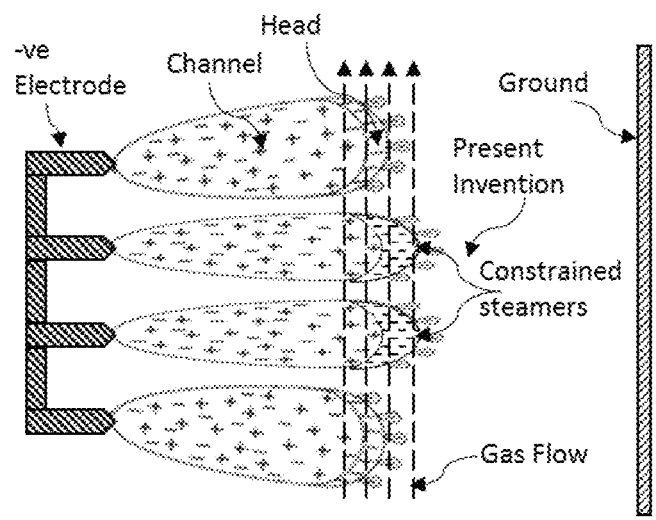
FIG. 2 is a schematic two dimensional illustration of field effects of neighboring streamers constraining the heads of internal ones and thereby limiting their radii growth according to at least one embodiment of the current disclosure.

Referring to FIG. 2, when multiple streamers are generated from identical discharge pins/ignition tips in close proximity, their own electrical fields would influence the characteristics of each other. For reference, identical ignition tips means having same geometric and material characteristics as well as same applied voltage across the counter electrode. As illustrated in FIG. 2, the top and the bottom streamers diverge away from the middle streamers due to the absence of any restrictive fields at the top and at the bottom side, respectively. Further, their radii are larger than the middle streamers. If constrained uniformly from all sides by the fields of neighboring streamers, radius thinning as well as field enhancement would occur as illustrated in the case of two middle streamers, thereby enhancing the product of the electron energy and the probability density distribution, and hence the free radical generation efficiency. The proximity field influence and its resulting streamer head field enhancement depends on several factors such as the inter pin gap and distribution of the ignition tips, the distance from the counter electrode, the discharge gas as well as the applied voltage.

Figure 3:
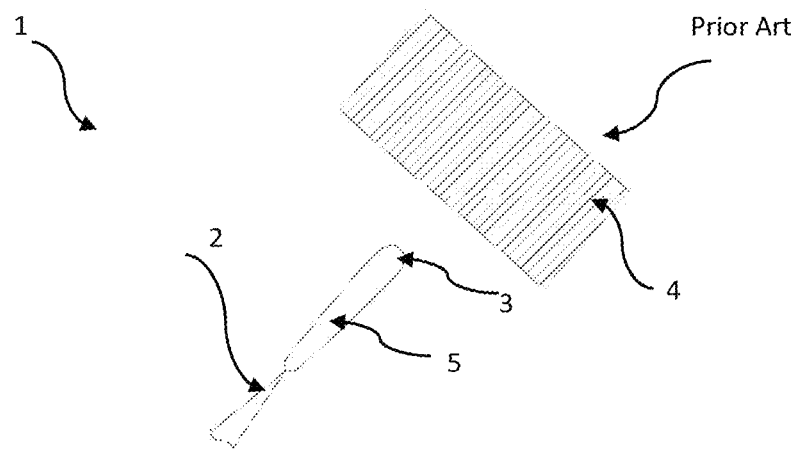
FIG. 3 is an exemplary schematic describing conventional discharge pin and streamer propagation from it according to at least one known art.

Referring to FIG. 3, when a sharp discharge pin 2 is placed against a ground/counter electrode 4, a streamer 3 would propagate through the discharge gap towards the ground electrode 4. The streamer channel 5 establishes a conductive path and hence the applied voltage needs to be removed prior to the streamer head 3 reaches the counter electrode 4 to prevent arcing. Therefore, a short voltage pulse is applied to the electrode. Sharp discharge pins are preferred for streamer as they lower the streamer ignition voltage. To generate multitude of streamers, many sharp discharge pins can be organized in close proximity, however, fabrication of such devices are very cumbersome. Citing the complexity and difficulty of deploying densely arranged sharp discharge pins, U.S. Pat. No. 7,042,159 B2 taught the use of electrodes with conical angles between 30-90° and it is claimed that due to this specified electrode angle, the streamer from each electrode expands over a wider region overlapping the inter electrode space.

Streamers originating from the same polarity discharge pins repel each other due to same (negative or positive) field enhancement at their heads. Further, streamer diameter enlargement reduces its field enhancement at the head, increasing the probability of secondary branching and hence in turn its radical generation capability. In other words, to enhance the radical generation efficiency, the discharge pin design and arrangement should aim at constraining the streamer enlargement as well as formation of secondary streamers and in turn enhance the field at its head.

Figure 4:
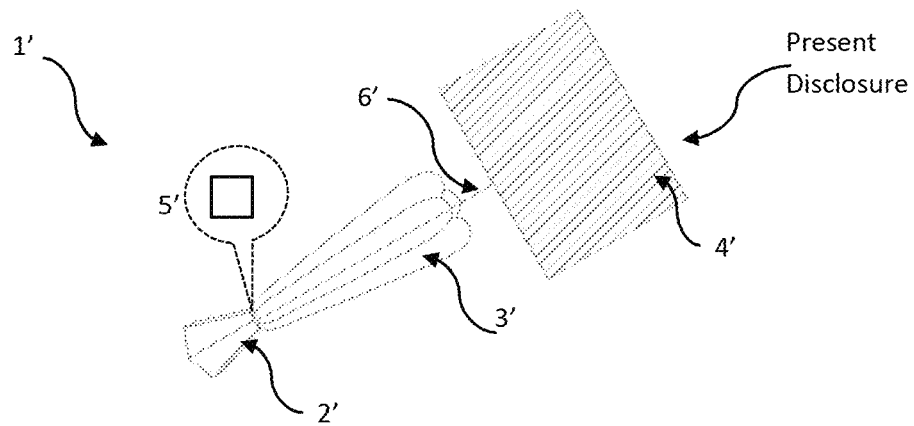
FIG. 4 is a schematic illustrating a columnar discharge pin with four streamer ignition tips to generate four diverging streamers according to at least one teaching of this disclosure.

Provided herein are discharge pin designs, their arrangement forming the active electrode assembly and devices that serve to improve streamer confinement, are readily manufactured, and thereby improve free radical generation. One example of an electrode is illustrated in in FIG. 4 depicting a discharge pin 2' having four sharp ignition tips (corners) (5'). When a voltage pulse higher than that of the streamer ignition voltage is applied across the discharge electrode pin 2' and the counter electrode 4', four streamers emerge from the four ignition tips and propagate towards the counter electrode. Accordingly, due to the field enhancement at the streamer head, the streamers would repel each other while propagating towards the counter electrode 4', or in other words, will diverge from the discharge pin normal 6'. Optionally, FIG. 5, further discloses a discharge pin 2" with six sharp ignition tips (corners) (5"). Accordingly, when an appropriate voltage pulse is applied across the discharge pin and the counter electrode, six streamers would emerge and propagate towards the counter electrode 4". Also, due to the repulsive forces at the streamer heads 3", the streamers would diverge from the normal 6" of the discharge pin.

It is appreciated that the number of ignition tips on the discharge pin may be any number greater than 1. The number of ignition tips is optionally 2, 3, 4, 5, 6, or more. Optionally, a device includes discharge pins with varying numbers of ignition tips. An ignition tip as used herein is a corner defining an angle at an edge or point and is sufficiently sharp to produce an individual streamer under the appropriate conditions.

Figure 5:
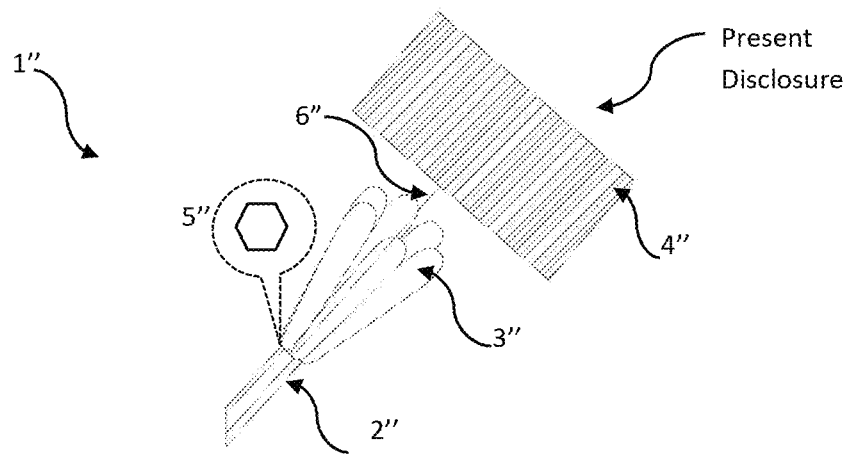
FIG. 5 is a schematic illustrating a columnar discharge pin with six streamer ignition tips to generate six diverging streamers according to at least one teaching of this disclosure.
Figure 6A:
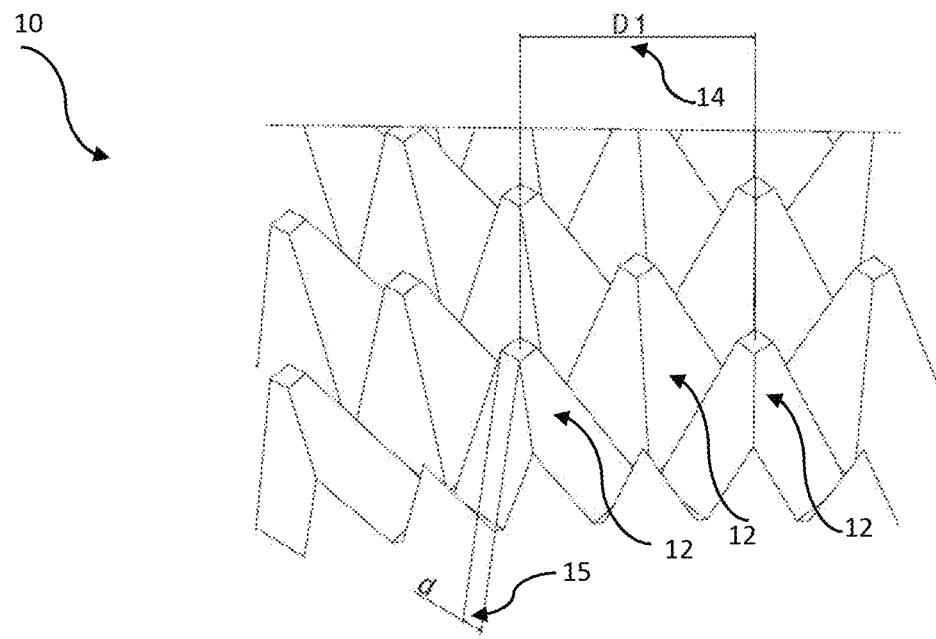
FIG. 6a is a schematic illustrating a periodic organization of columnar discharge pins with four-ignition tips according to at least one teaching of this disclosure.

Although the streamers of FIGS. 4 and 5, repel each other and diverge away from the pin normal, they would still continue to expand and thereby weakening the field enhancement at the streamer head and potentially form secondary streamers, in the absence of any surrounding electrical fields that can constrain them. However, in the presence of surrounding discharge pins that are identical and optionally uniformly positioned, streamers of similar characteristics will emerge from those and hence provide field constraints that will restrict the streamers from weakening and direct them towards the counter electrode. Accordingly, FIG. 6a discloses an electrode assembly 10 with discharge pins 12 that are positioned such that the distance (D1) 14 between pin normal is substantially identical all around. Further, the distance d between the ignition tips 15 on each discharge pin may be substantially identical. Although d is always smaller than D1, several considerations are taken into account for best operational and fabrication practice. The smaller D1 is, the larger is the number of discharge pins and higher is the number of streamers for a given surface area. In some aspects D1 is between 0.25 and 25 mm, and optionally D1 is between 1-10 mm. Further, very small d also poses problems for maintaining the tolerance of the ignition tips. As such, d is optionally between 0.05 mm and 10 mm, and optionally, d is between 0.1 mm-2.5 mm.

Figure 6B:
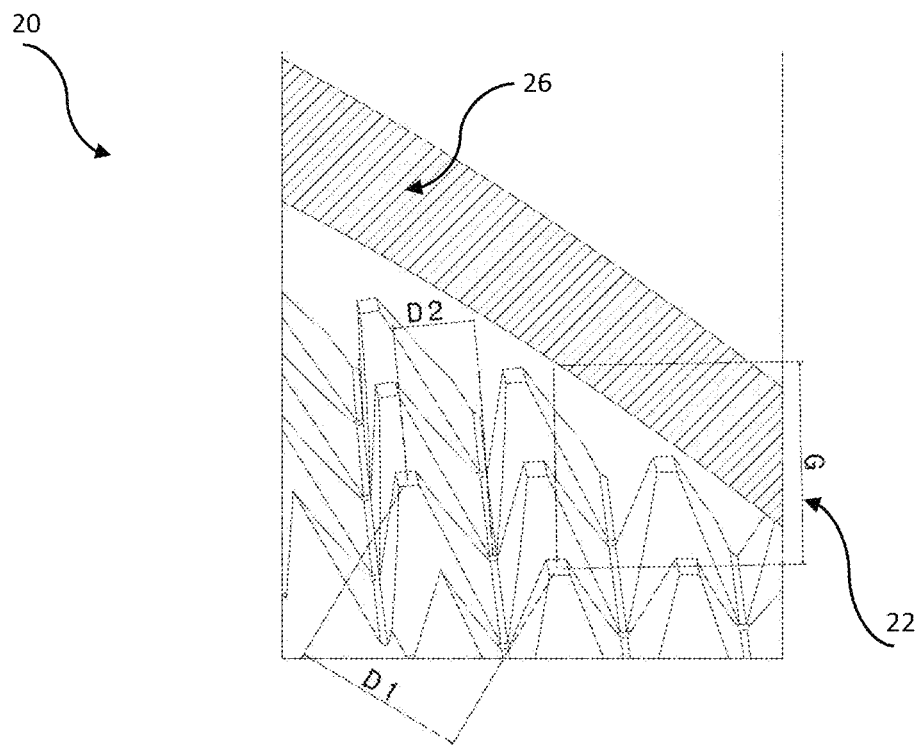
FIG. 6b is a schematic illustrating a discharge electrode assembly deposed adjacent to a common counter electrode keeping each discharge pin normal to the surface of the counter according to at least one teaching of this disclosure.
Figure 7:
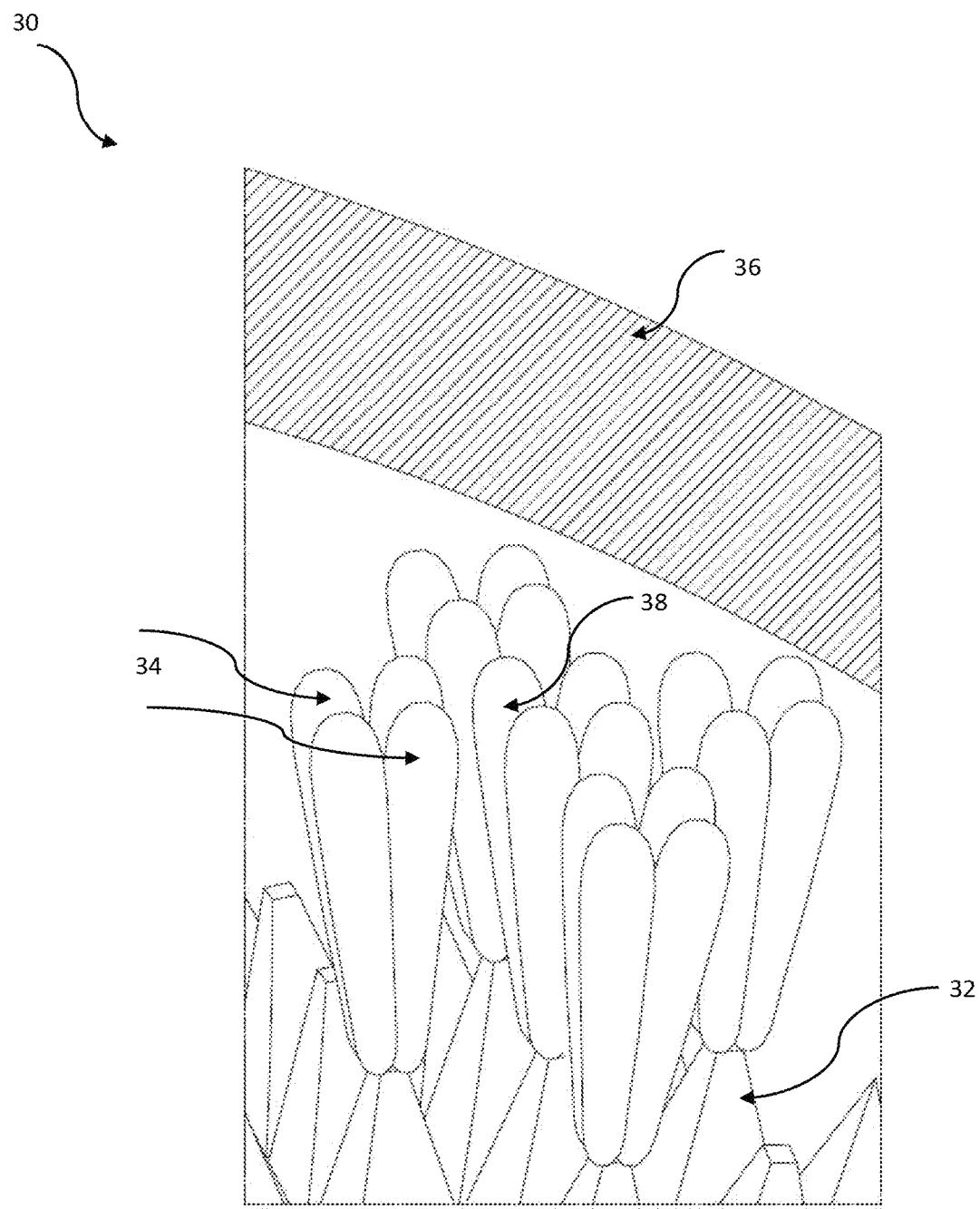
FIG. 7 is a schematic illustrating streamer propagation from the discharge pins towards a common ground electrode according to at least one teaching of this disclosure.

Further consideration is given to the distance between the ignition tip surface and the counter electrode. Now referring to FIG. 6b, the distance between the ignition tip to the counter electrode surface G is known as discharge gap and has considerable impact on the device performance. The discharge gap 22 influences the gas flow rate, the time required for the streamer to cross the discharge gap, as well as the streamer characteristics. If the time required for the streamer to cross the discharge gap is Ts and Tp is the full width at half maximum (FWHM) of the current pulse, then their ratio R=Ts/Tp plays an important role on the discharge gap as well as the power supply design. When R=1, the voltage pulse ends at the moment the streamers reach the counter electrode and this presents the best situation. If R>1, then the time required for the streamers to cross the discharge gap exceeds the pulse duration. In this case, the streamer stops propagating at a position in between the electrodes, and this situation is not desired. If R<1, then part of the pulse energy is not utilized in the discharge process and needs to be dissipated (heat) or recuperated. Since streamers travel at velocities in the order of $10^6$ m/s, the condition R=1 can be maintained either by maintaining a large discharge gap or applying very short pulses (~1 μs or less). A larger discharge gap would require a higher applied voltage for streamer propagation through the discharge gap. Extremely short pulses complicate the power supply design due to high switching frequencies and efficiency loss. Also, high switching frequencies lead to high EMI noise, making the electronic component operation very difficult. Therefore, it is preferred to operate the device under the condition R<1 along with an energy recuperation circuit to capture the portion of the pulse energy that is not utilized in the discharge process. The discharge gap may optionally vary between 0.5 mm and 30 mm and as such the discharge gap is optionally bigger than 1 mm and is optionally smaller than 15 mm. In the case of negative polarity shorter discharge gaps are preferred where as in the case of positive polarity longer discharge gaps are preferred. As such, for negative polarity, the discharge gap is optionally at or above 1 mm, optionally at or above 2 mm, optionally at or above 3 mm, optionally at or above 4 mm, optionally at or above 5 mm, optionally at or above 6 mm. For positive polarity, the discharge gap is optionally at or above 5 mm, optionally at or above 6 mm, optionally at or above 7 mm, optionally at or above 8 mm, optionally at or above 9 mm, optionally at or above 10 mm, optionally at or above 11 mm, optionally at or above 12 mm, optionally at or above 13 mm, optionally at or above 14 mm. Furthermore, it is preferred to keep D1=G, i.e., inter electrode distance equal to the discharge gap, however, it is not a necessary condition.

Figure 8:
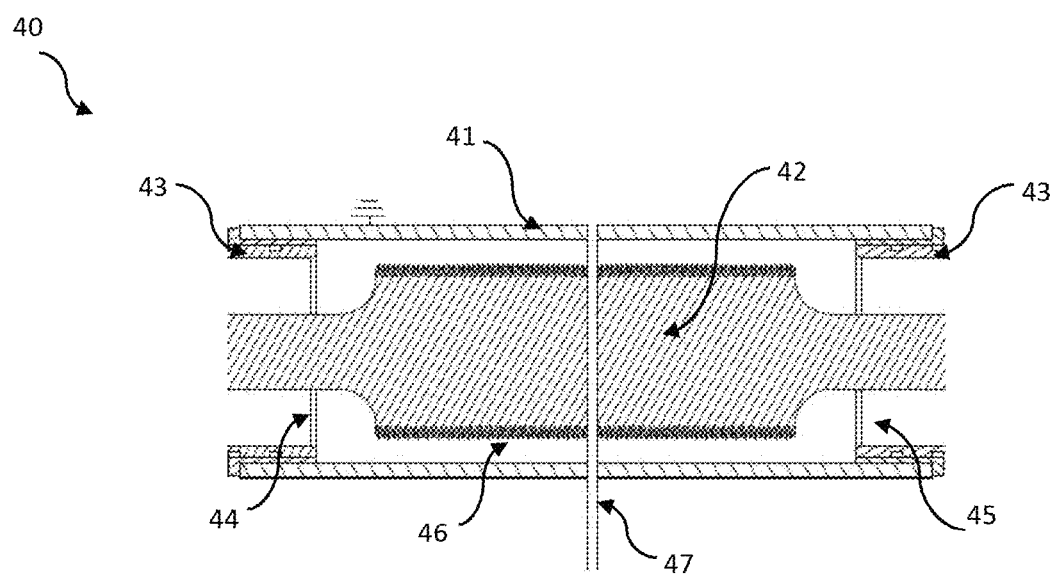
FIG. 8 is a schematic embodiment of a discharge device according to the teachings of this disclosure.

When a voltage pulse is applied to the electrode assembly 30, four streamers would emerge from each discharge pin with one streamer from each of the ignition tip. While each streamer 34 would try to diverge away from the normal of the discharge pin, it would also experience a repulsive force due to the electrical fields of the streamers 38 emerging from the surrounding discharge pin. This arrangement ensures that each streamer is constrained from all sides and travels towards the counter electrode. This constraint from the surrounding streamers prevents the formation of secondary streamers and ensures sufficient number of high energy electrons at the streamer head which lead to efficient ionization and radical formation. Deploying this teaching of proximity constraint by surrounding streamers, a radical generation device is disclosed in FIG. 8. The radical generator 40, comprises of a central cylindrical discharge electrode assembly 42 surrounded by a cylindrical counter electrode 41. The central discharge electrode assembly 42 is electrically isolated from the counter electrode by at least end cap 43. Optionally, the device includes two end caps for maintaining the concentricity of the discharge electrode assembly 42. The end cap includes a concentric inlet flow passage 44 and the outlet flow passage 45. It is to be noted that the inlet and outlet passages are interchangeable. The end cap 43 is made from a non-nonconductive material. Optionally, the material is acrylic, and optionally, the material is a ceramic. A gas supplier (not shown here) supplies the gas into the device, which passes through the discharge gap 46. Upon applying of a suitable electrical voltage pulse, streamers emerge from the discharge electrode assembly towards the counter electrode and in turn generate radicals in the gas stream within the discharge gap.

Figure 9:
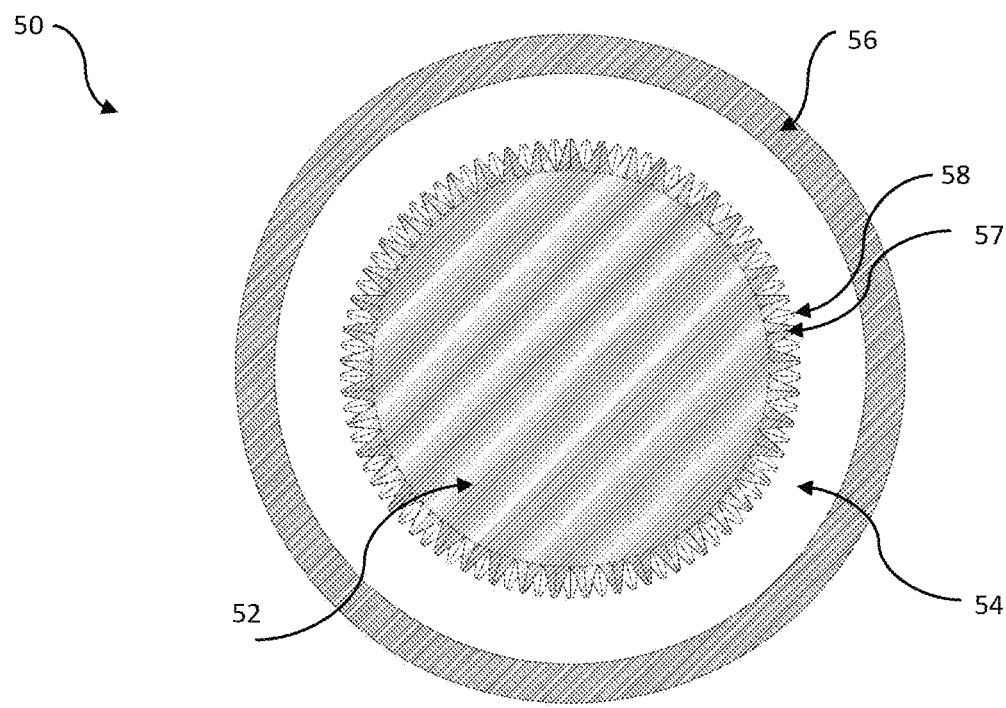
FIG. 9 is a cross (middle) sectional schematic of discharge device illustrated in FIG. 8, according to this disclosure.
Figure 10:
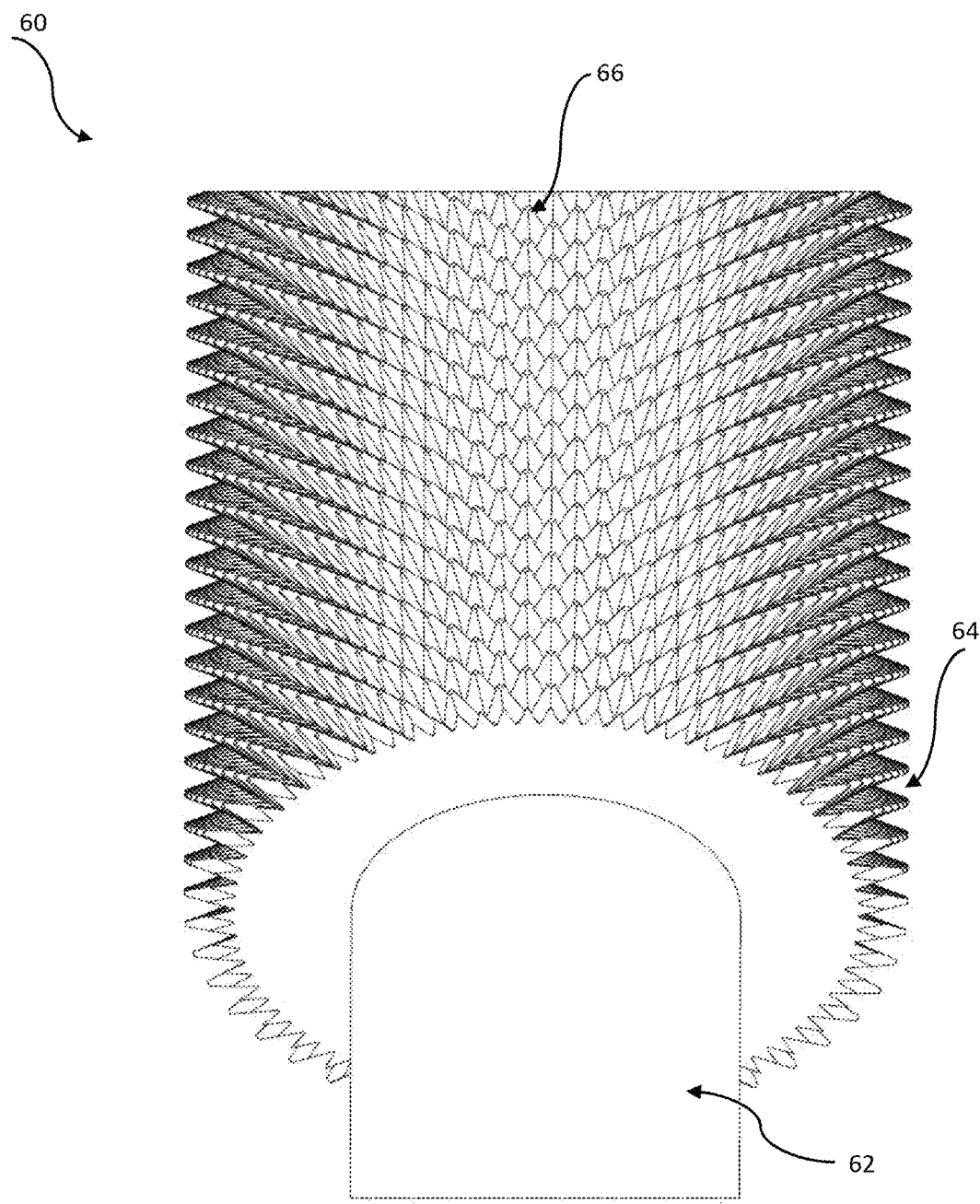
FIG. 10 is a perspective view of the discharge electrode assembly, showing periodically organized columnar discharge pins having four ignition tips, according to this disclosure.
Figure 11:
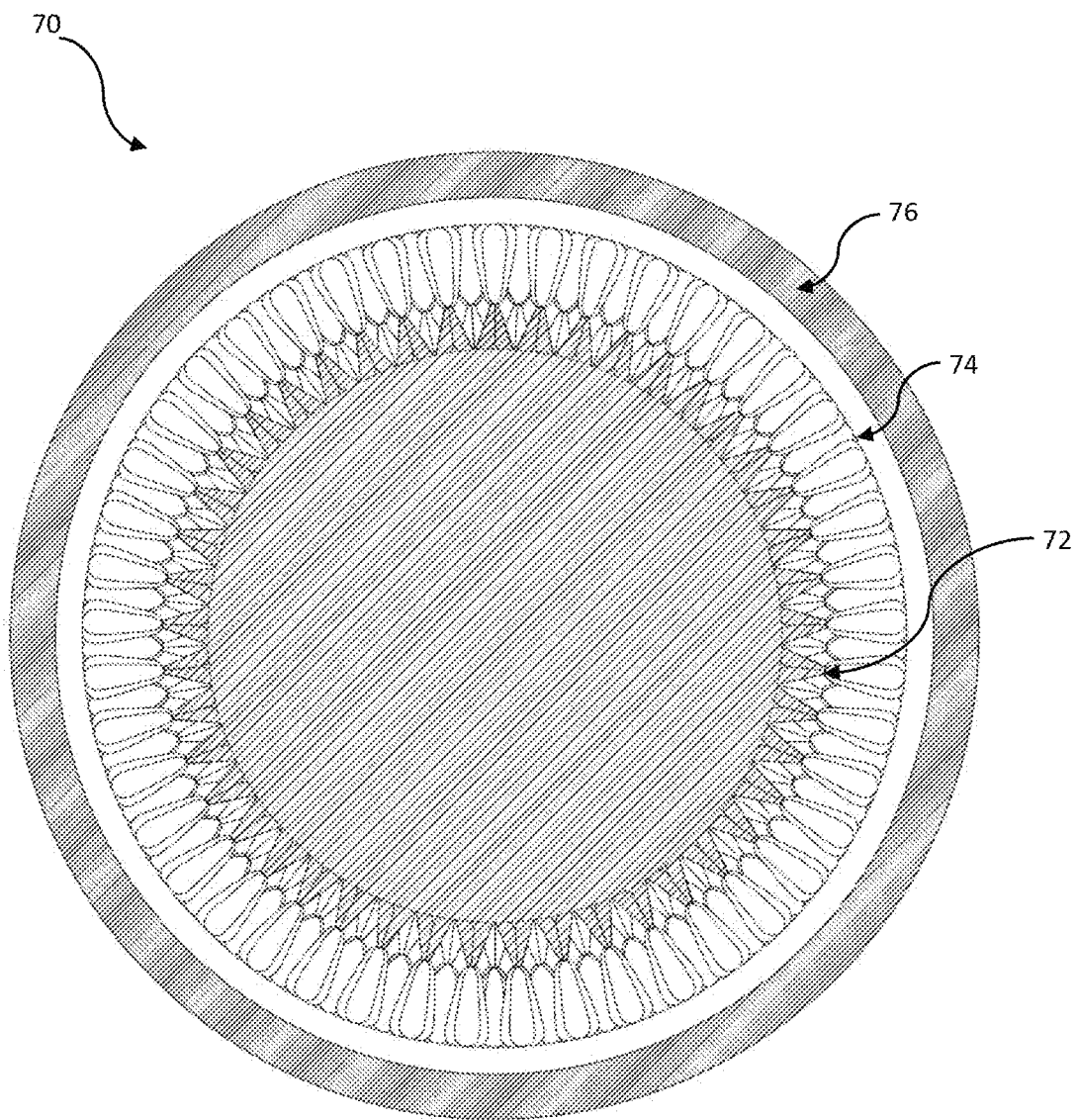
FIG. 11 is an illustration of streamer propagation from the discharge electrode assembly towards the common ground electrode forming an ionization front according to this disclosure.
Figure 12:
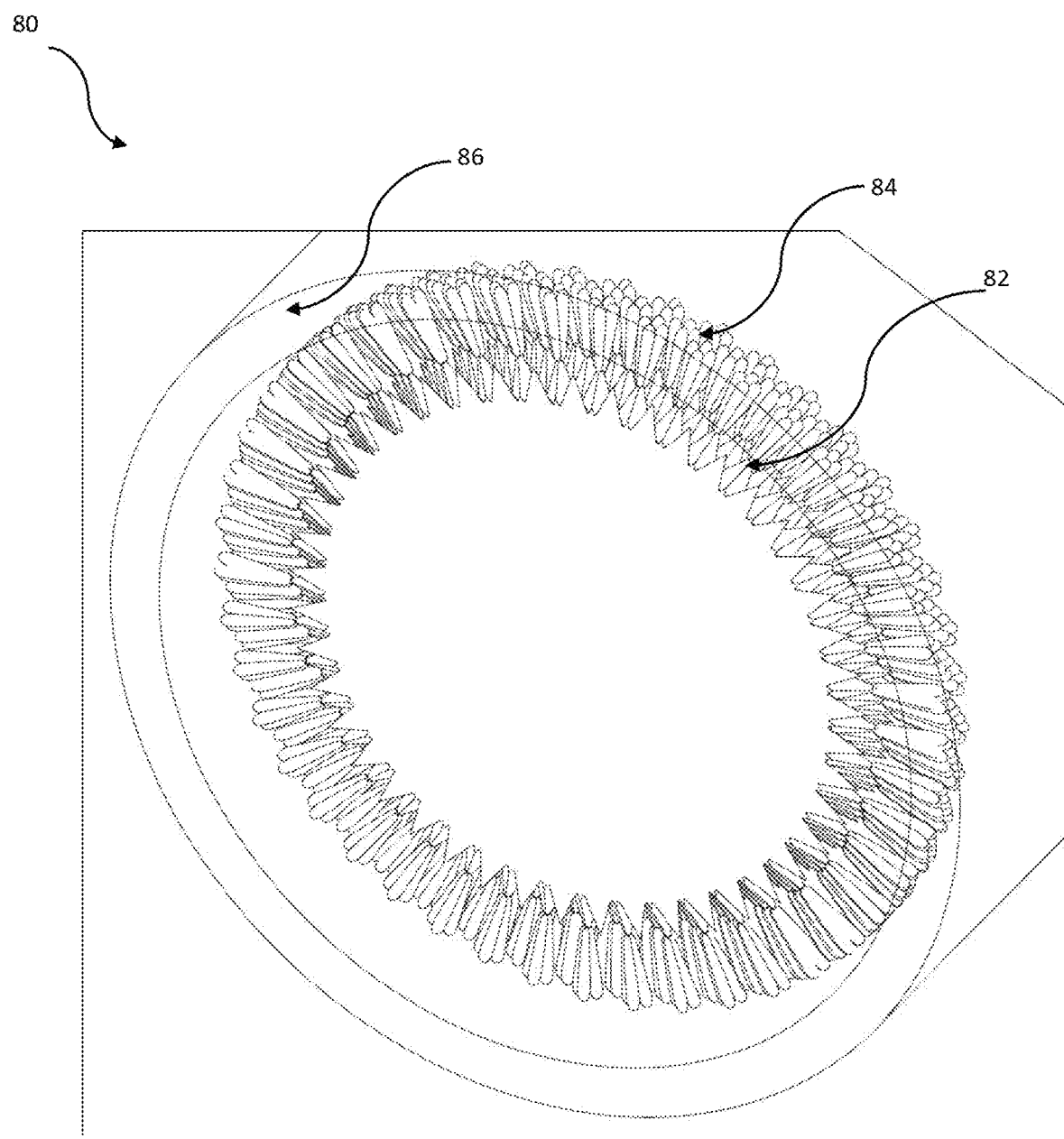
FIG. 12 is a perspective view of streamer propagation from the discharge electrode assembly towards the ground electrode forming an ionization front according to this disclosure.
Figure 13:
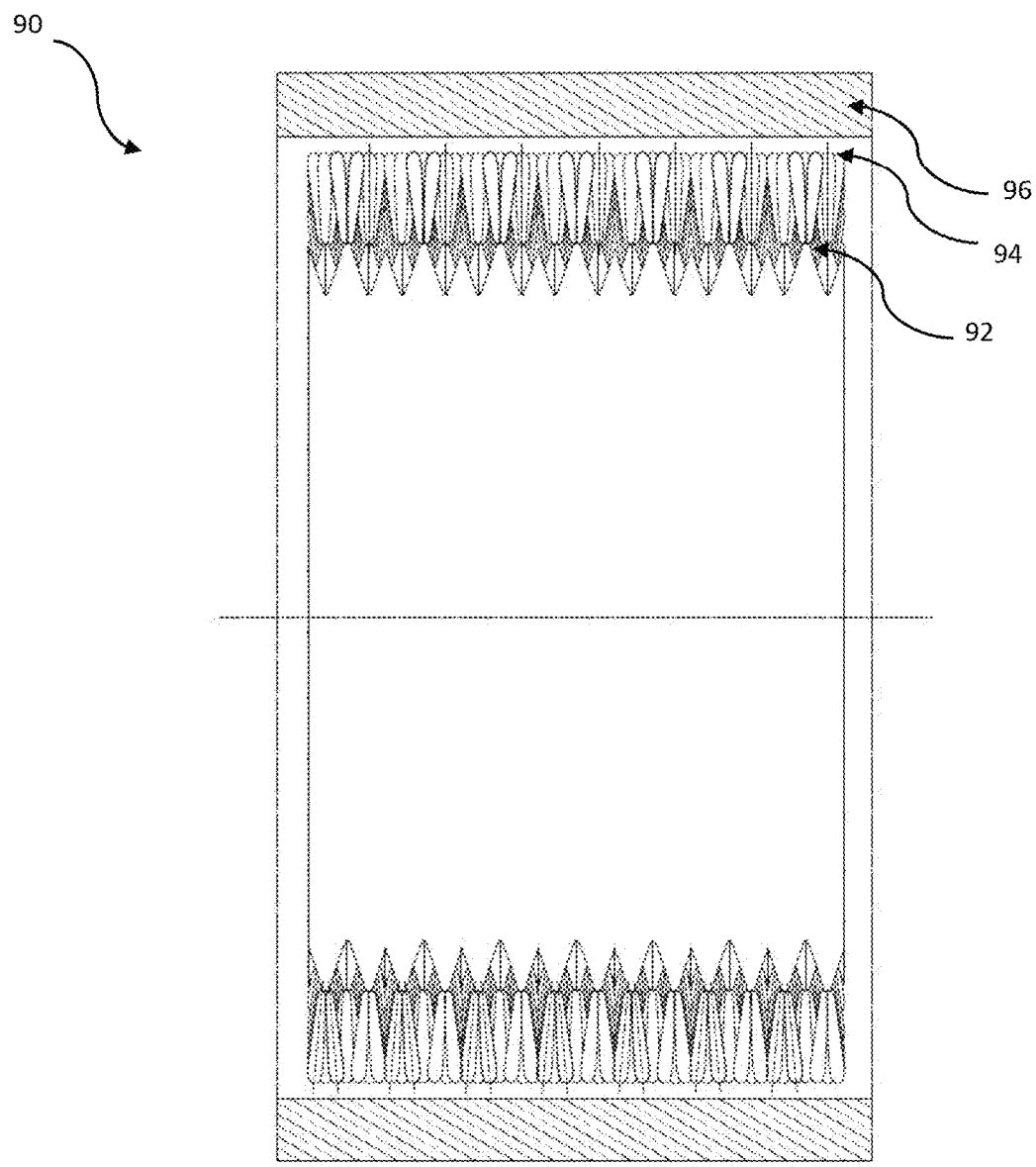
FIG. 13 is a cross section view of streamer propagation from the discharge electrode assembly towards the ground electrode forming an ionization front according to this disclosure.

Further attention is drawn to the construction of the discharge electrode assembly 52 in FIG. 9. This cross sectional view is taken at 47 of the radical generator 40. As illustrated, the discharge pin 58 is positioned at an angle from the discharge pin 57, thereby maintaining a uniform distribution of the pins along the surface discharge electrode assembly 52. Optionally a uniform field constraint is maintained around each streamer around the circumference of the electrode assembly. The periodic distribution of the discharge pins is further illustrated in FIG. 10. As mentioned earlier, higher the number of the discharge pins, higher number of streamers will be formed and better will be the radical generation efficiency. However, accurately positioning these discharge pins by cost effective fabrication techniques is a key consideration for the implementation the teachings of the present disclosure. The disclosed electrode assembly 60 can be machined by a mill/lathe machine cost effectively. The specific pyramidal structure enables one to maintain good accuracy and avoid pin deformation. Upon applying suitable voltage pulse, constrained primary streamers emerge from the entire electrode assembly and propagate through the discharge space as illustrated in FIG. 11. The head of the streamers form an ionization front 74 as it moves towards the counter electrode 76. Such arrangement ensures high radical generation efficiency. Particularly, when the gas is treated inside the discharge space for purification or chemical reaction, the uniform interaction of the ionization front formed by the streamer head enables effective fast chemical reaction. The perspective view of the ionization front 84, formed by the streamer head of the present disclosure is shown in FIG. 12. The cross sectional view of the streamer front 94 is shown in FIG. 13. As the gas passes through the discharge space, successive interaction with streamer front ensures ionization and radical formation as well as associated chemical conversion.

The ability to constrain the streamer heads by the repulsive fields of surrounding streamers without changing the applied voltage, as disclosed here, enables one to shift the probability density distribution with electrons of selective energy levels. Consequently, one can selectively generate abundant OH* radicals by focusing the probability density distribution to the vicinity of 5 eV, whereas the N* radicals can be effectively generated by shifting the probability density distribution to the vicinity of 9 eV. In a gas mixture, while OH* radicals can be selectively generated, it is not possible to select for O* and N* radicals. While higher energy electrons will form N* radicals, they will also form abundant OH* and O* radicals, if moisture and oxygen are present in the gas mixture. However, in a dry gas one can selectively generate O* radicals and suppress N*, which is important for ozone production. Optionally, purified oxygen can be used to generate O* radicals and in turn ozone only.

The polarity of the discharge pins, the applied voltage, the geometric parameters (discharge electrode assembly as well as the discharge gap) of the device, and the pulse width may be tailored to influence the selectivity as well as the yield of the radicals. The field enhancement at the positive streamer head continues to increase as it traverses through the discharge gap whereas the enhanced field at the tip of the negative streamer diminishes during its flight. Consequently, for positive streamer the availability of high energy electrons throughout the discharge space is generally higher than that of the negative streamers. The discharge gap and the pulse width determine the ratio R defined above. Higher applied voltage increases the streamer velocity and lowers the R. Highest yield occurs when R is small, however, very small R may not be desirable for complications associated with the power supply design as well as conversion efficiency. Generally, for selectively generating OH* radicals (requires low dissociation energy), larger discharge gaps may be preferred, whereas, radicals requiring higher electron energy a smaller discharge gap may be selected. Nevertheless, there are many other parameters such as discharge pin geometry and inter pin distance, which may be tailored to achieve similar outcomes for a given discharge gap and electrical parameter.

In addition to the streamer head confinement as disclosed herein, one can also select the polarity of the discharge electrode to achieve a selective outcome. The positive streamers have higher field enhancement compared to negative streamers. Hence, to maximize OH* or O* radicals, a negative polarity of the discharge electrode is preferred, whereas for N* radicals, a positive polarity of the discharge electrode is a preferred option. However, in both cases, the field enhancement methodology due to streamer head confinement as disclosed here, is available.

Figure 14:
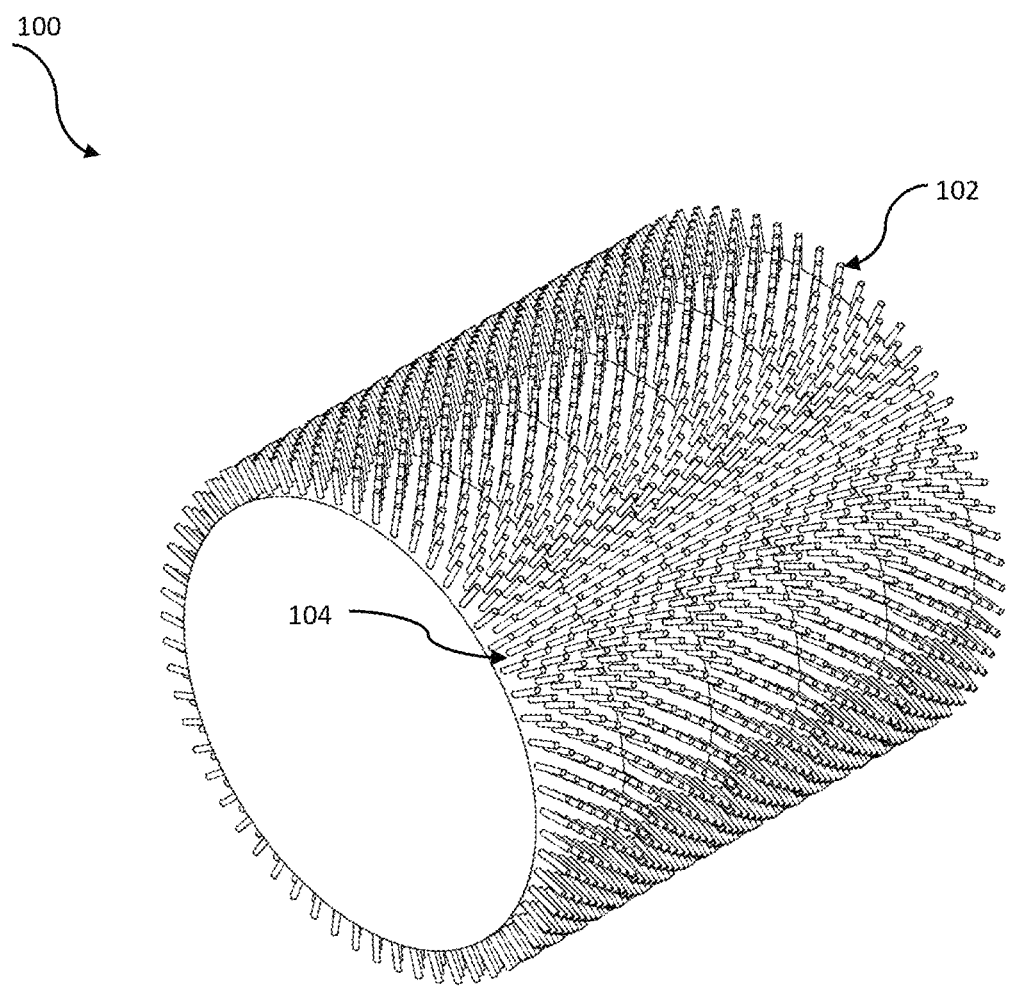
FIG. 14 is an exemplary illustration showing possible discharge pins arrangement according to prior art.
Figure 15:
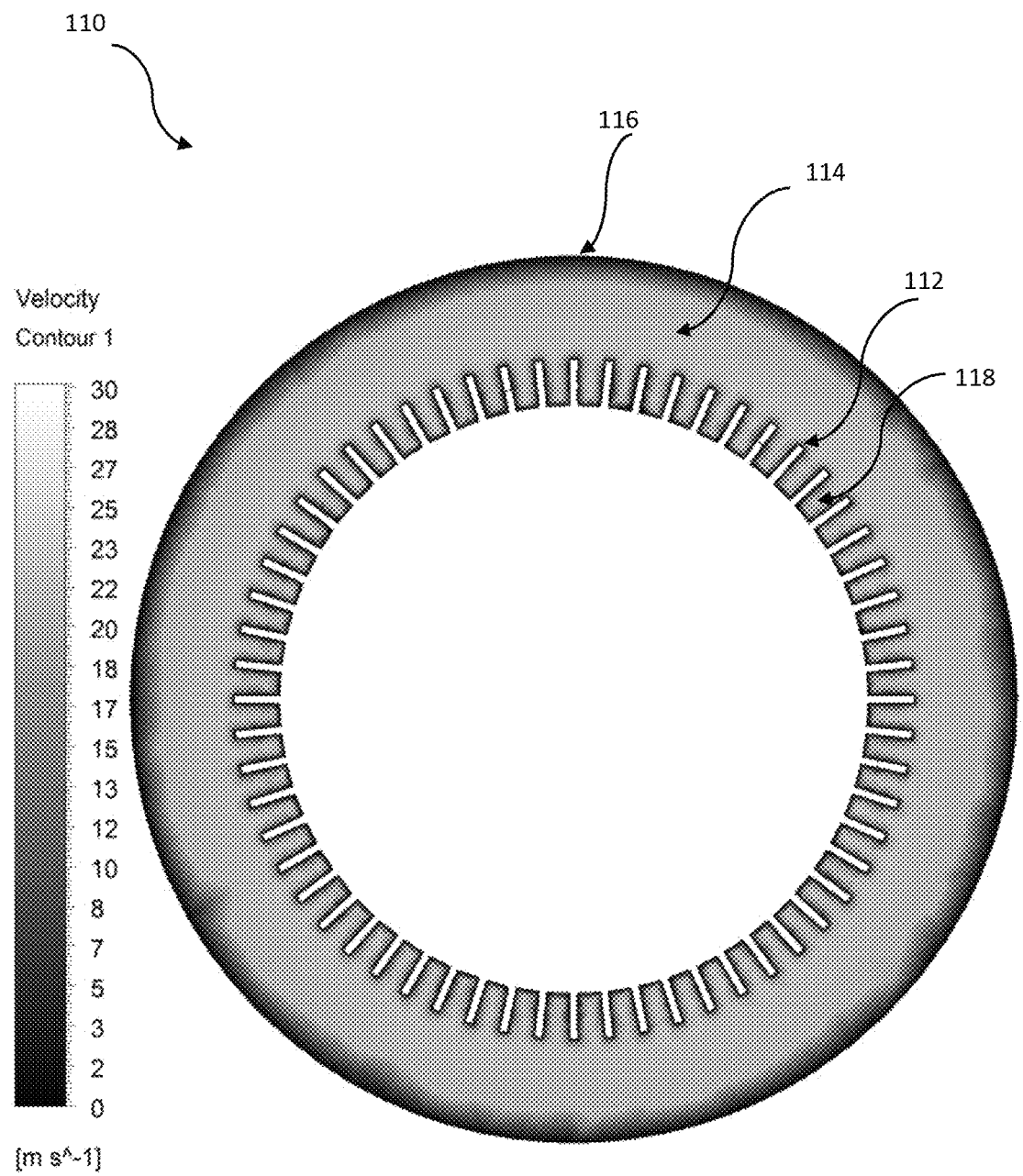
FIG. 15 is a flow simulation illustrating the gas flow through inter pin gaps of an exemplary discharge electrode assembly shown in FIG. 14, according to prior art.
Figure 16:
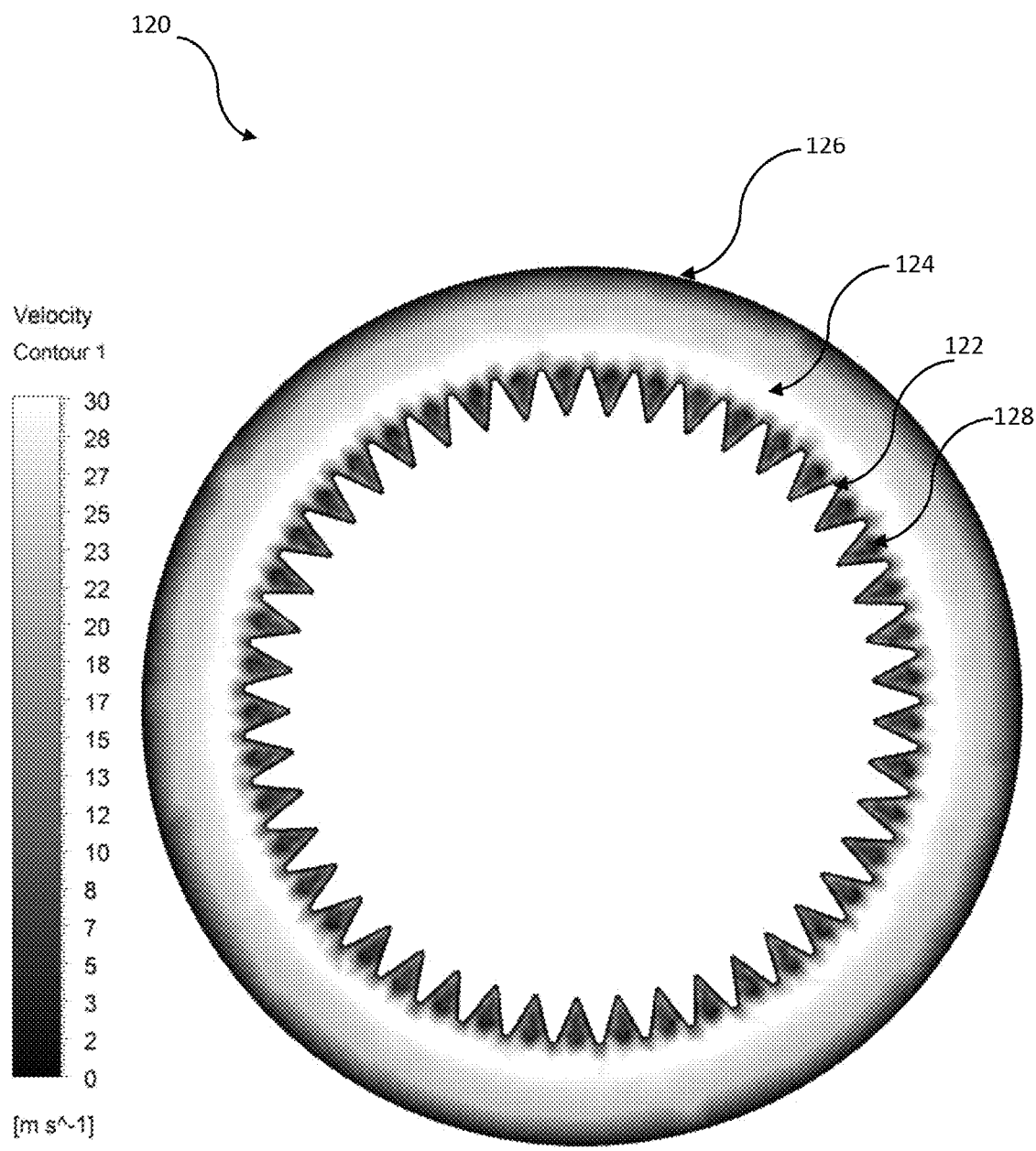
FIG. 16 is a flow simulation illustrating the gas flow obstruction in the inter pin gaps of the discharge electrode assembly shown in FIG. 10 according to this disclosure.
Figure 17:
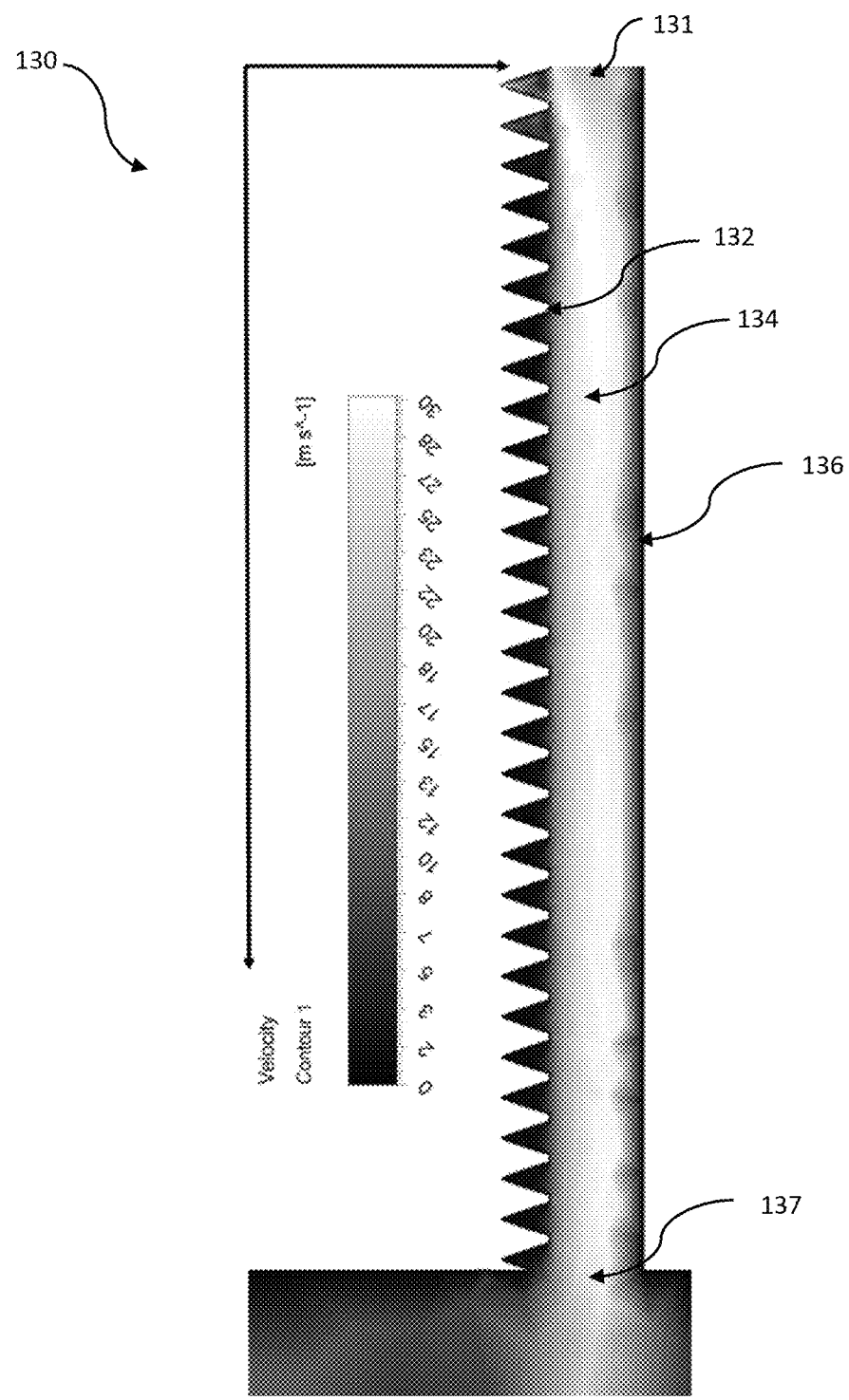
FIG. 17 is a flow simulation illustrating the gas flow obstruction in the inter pin gaps while maintaining high gas flow at the ignition tips of the discharge electrode assembly shown in FIG. 10 according to this disclosure.

Now referring to FIG. 14, many sharp discharge pins can be arranged on a cylindrical surface to provide a large number of streamers and hence effective radical generation. However, fabrication of such sharp pins is cumbersome and expensive. Further issues with this type of pins 102 is illustrated in FIG. 15 which shows a flow simulation of a feed gas in a device fabricated deploying the electrode assembly 100. The simulations were carried out by flow simulation software Fluent 16.0 with 30 m³/hour airflow and a discharge gap of 5 mm. As can be seen by the extensive light shading, a significant fraction of gas passes through the inter-electrode space 118. Since the streamers emerge from the pin tips, the fraction of the gas that passes through the inter-pin space would never interact with the ionization front of the streamer head. In fact, when this gas collides with the ionized gas that has interacted with the streamer head, it leads to significant radical loss. The benefits of pyramid shaped discharge pins 122 is illustrated in FIG. 16 which shows a flow simulation of a feed gas in a device fabricated deploying the electrode assembly 60. The electrode assembly 60 provides an obstruction to the gas flow through the inter pin space. Referring to FIG. 16, it can be seen from the dark shading that the flow velocity in the inter-pin space 128 is the lowest and the majority of the gas is forced to pass through the discharge space where it is forced to interact with the ionization front of the streamers. This ensures high degree of ionization and radical formation as well as effective chemical reaction. Although the gas velocity in the inter pin gap is low, the gas velocity at the ignition tips 132 is quite similar to that of the discharge space 134 as shown in FIG. 17. The gas flow at the ignition tip is beneficial as it prevents accumulation of impurities, moisture and ions. The accumulation of impurities impacts the performance of the device and especially accumulation water droplet may lead to arcing and pin damage. The significance of gas flow in the discharge space will be further discussed below.

Figure 18:
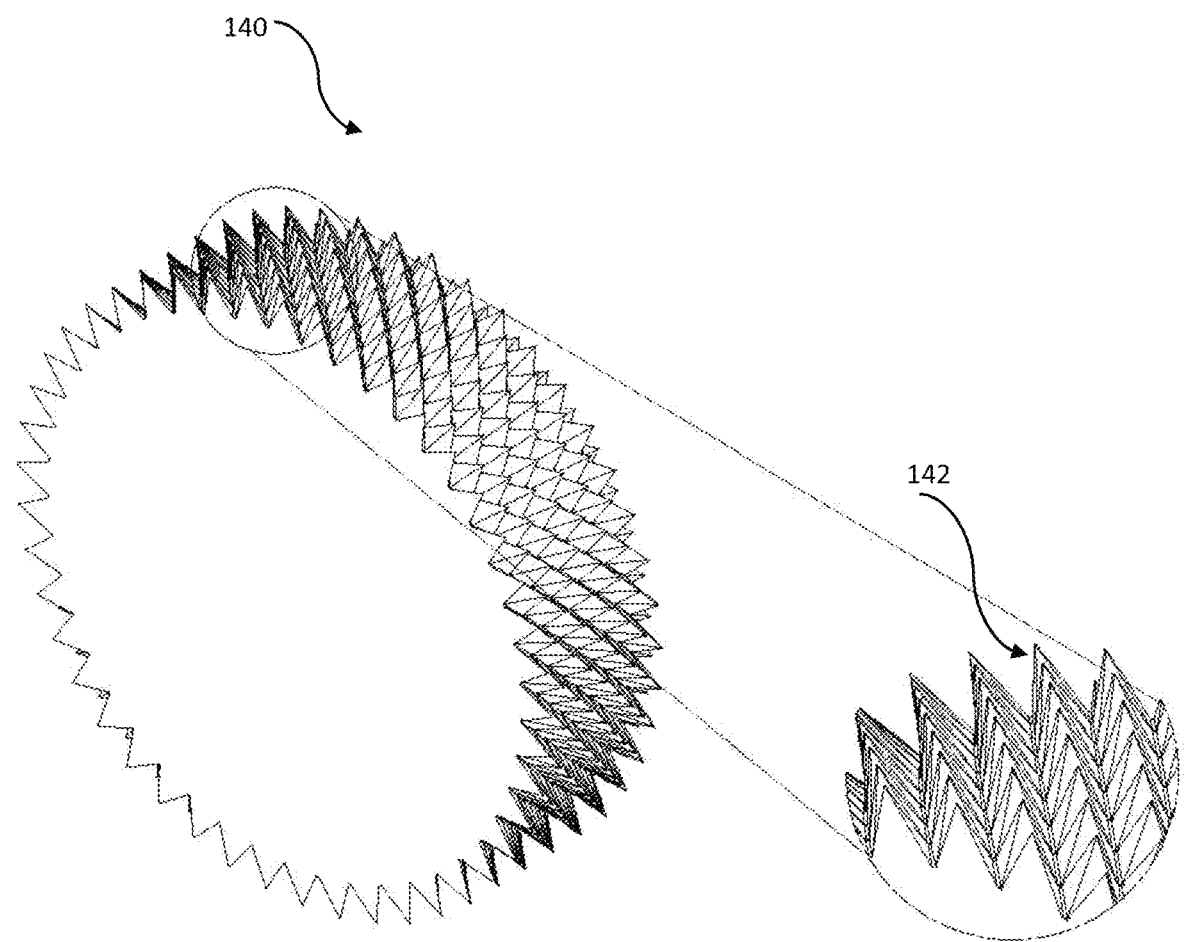
FIG. 18 is an illustration showing pyramidal discharge pins with single ignition tip arranged periodically on the discharge electrode assembly according to one optional embodiments of the current disclosure.

An optional design for the discharge electrode assembly is presented in in FIG. 18 where the pyramidal discharge pins include only one ignition tip. The bases of the pyramids as shown in FIG. 18 are substantially joined, and in some aspects may include a space between pyramid bases while other air flow prevention designs, optionally, as illustrated herein may be used. Although, the flow benefits illustrated in FIGS. 16 and 17 will be mostly realized in the design, the reduction in the ignition tips will reduce the number of streamers. One can potentially machine equivalent number discharge pins and hence equivalent number of ignition tips, however, that would necessitate narrower pyramids with deeper valleys between the discharge pins. Especially, due to the low mass and hence stiffness at the ignition tip, it will be extremely cumbersome to maintain sharp tips during machining. On the other hand, the square profile taught here provides a rigid base for achieving tight tolerance in addition to providing four ignition tips. Further, maintaining the geometric accuracy during handling as well as operation is easier with the electrode assembly comprising of discharge pins with multiple ignition tips as disclosed here. Although, the discharge electrode assembly presented in FIG. 10 is cylindrical, optionally, it can be of other shapes such as flat, conical or hemispherical. The cylindrical and flat electrodes are convenient for fabrication by standard machining techniques and scaling up.

Further attention is drawn towards the materials utilized for fabricating the discharge electrode assembly. The environment in the discharge space is chemically very active due to the presence of free radicals. Depending upon the feed gas, the radicals may oxidize, nitride or hydrolyze the discharge pins forming complex compounds. Therefore, the electrode should be made from a group of materials possessing good chemical resistance as well as good electrical conductivity to prevent unwanted deterioration. Particularly, the discharge pins with sharp ignition tips tend to react quickly and lose their geometric as well as electrical conductivity. Further, the polarity of the discharge electrode also affects its life; positive polarity (anode) increases the chemical activity compared to negative (cathode) polarity. Materials such as silicon carbide are preferred for discharge pins with positive polarity, whereas materials such as stainless steel, among others, can optionally be used for discharge pins with positive polarity. A graphite or carbonaceous counter electrode is optionally used to prevent corrosive reaction due to continuous bombardment of the streamers on it, although metals such as titanium and stainless steel, among others, can optionally be used.

As discussed above the electrical parameters applied to the discharge device determines the operational characteristics of the device and in turn the resulting nature and the yield of the radicals. Generally, the applied electric field may optionally range between 10-200 kV/cm, optionally 10-100 kV/cm. However, while the applied electric field should be maximized for a given type of streamer, it should be at a tolerable range without breaking down the resistance of the discharge space. Higher applied voltage increases ionization in the discharge gap and discharge current and lowers the ignition delay. The applied electric fields for ADS (negative) is optionally between 25-50 kV/cm and is optionally between 20-40 kV/cm for CDS (positive). Extremely short pulses and large discharge gaps should be avoided. The pulse width may optionally vary between 10 nanoseconds (ns) to 50 microseconds. As such, the pulse width is optionally between 50 ns and 5 microseconds and is optionally between 200 ns and 1 microsecond. The energy transfer efficiency can be increased considerably by decreasing the discharge gap. Firstly, the average electric field increases with decreased discharge gap, resulting in decreased plasma resistance. Secondly, for shorter discharge gap the streamer propagation duration decreases. The energy per pulse and the pulse frequency are two important parameters that determine the overall power consumption by the device. The energy dissipated per discharge pin may optionally be between 0.1 µJ to 100 µJ, optionally between 1.0 and 20.0 µJ. The frequency may optionally range between 100 Hz to 100 kHz, optionally between 10 kHz and 30 kHz. It is imperative that the device can be scaled up by assembling more and more discharge pins and supplying the energy accordingly. However, as the radicals form, the characteristics (ignition voltage) of the discharge gap change which may necessitate differing applied voltage as the gas travels through the discharge space from one end to the other. Therefore, a very long discharge channel is not recommended and the discharge channel length, may optionally be between 1 cm and 1 meter, may optionally be between 5 cm and 50 cm. The gas flow rate considerably influences the energy that can be delivered to the device and in turn the radical concentration as well as quantity. While low gas flow increases the radical concentrations, the yield is lowered due to competition between generation and destruction rates as well as space charge build up which leads to unstable ignition voltage and arcing. Higher gas flow reduces the radical concentration but improves the yield. For a given pressure gradient, the gas flow rate depends on the discharge gap, and hence, the gas velocity in the discharge space is a useful parameter for proper device operation. The gas velocity in the discharge space may optionally be in the range of 0.1 m/s to 200 m/s. As such, the gas velocity in the discharge space is optionally 2 m/s, optionally 5 m/s, optionally 10 m/s, optionally 15 m/s, optionally 20 m/s, optionally 30 m/s, optionally 40 m/s, optionally 50 m/s, optionally 60 m/s. The volumetric energy, i.e., energy/liter of gas, is an important characteristic of the device. The volumetric energy may optionally vary from 5 J/L to 5 kJ/L, optionally 200 J/L to 1 kJ/L.

Figure 19:
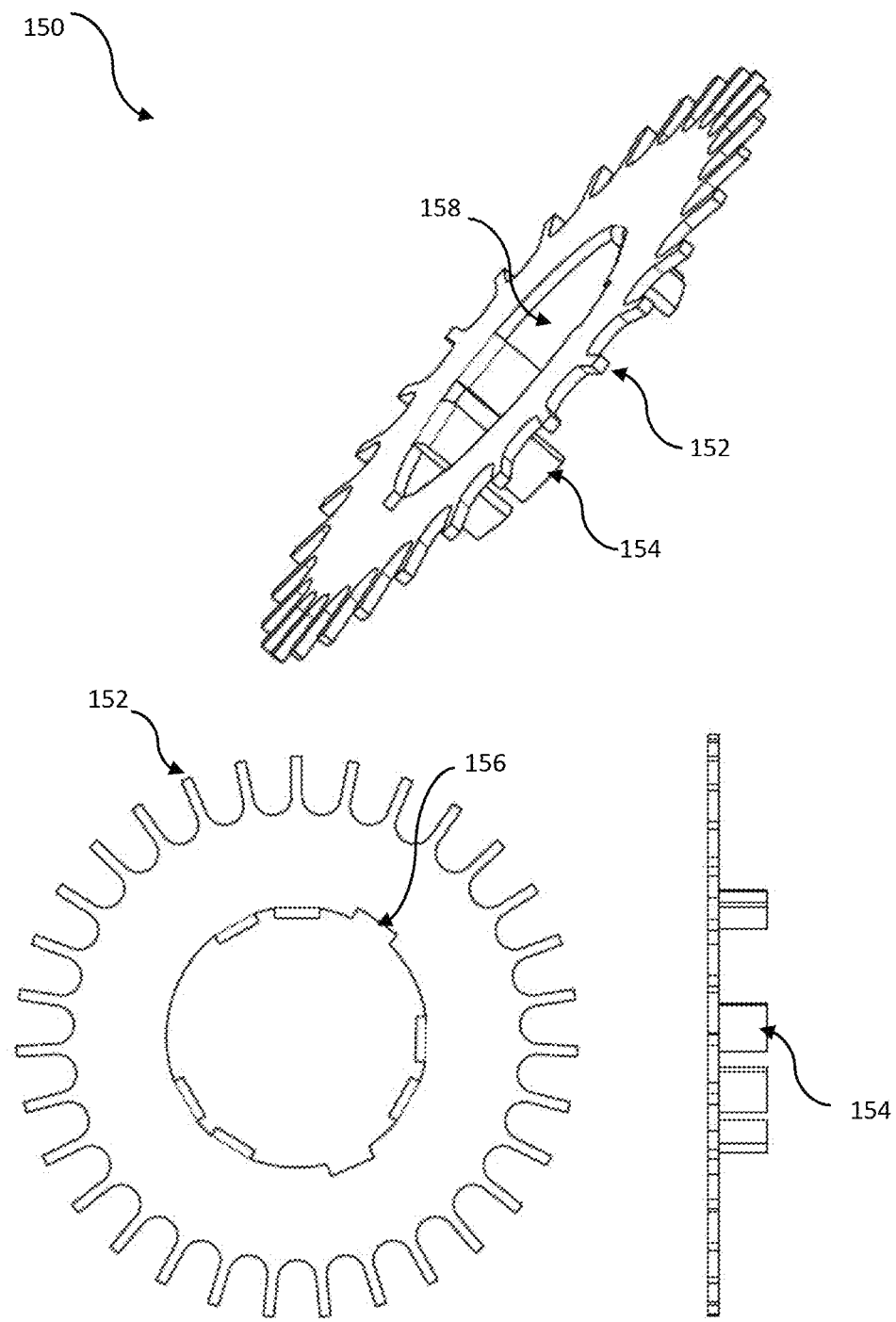
FIG. 19 is an illustration of a disc type discharge electrode having columnar discharge pins with four ignition tips according to the teachings of one optional embodiments of this disclosure.
Figure 20:
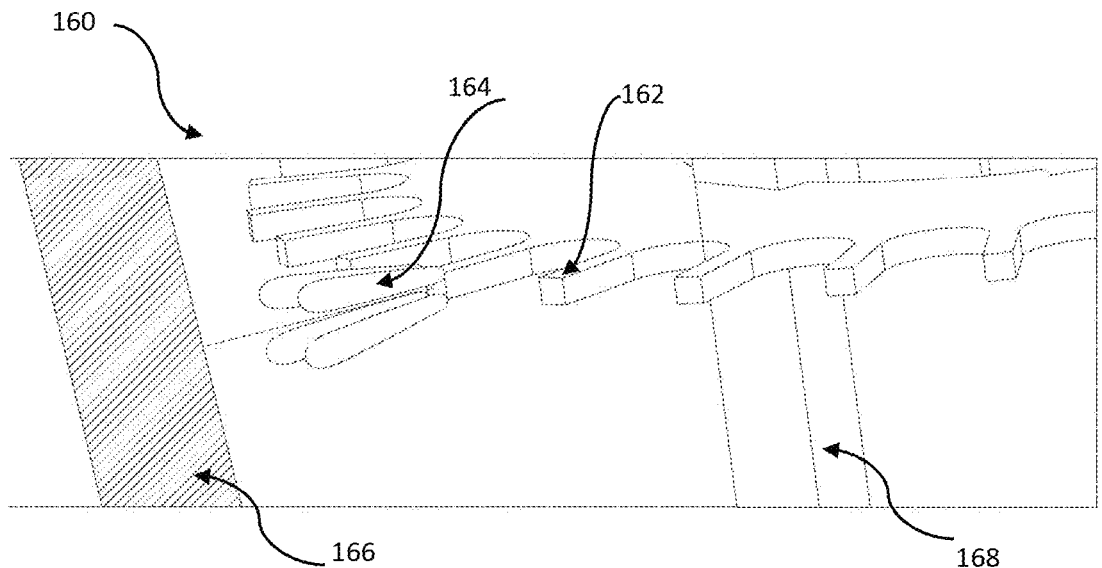
FIG. 20 is a schematic illustration of streamer propagating towards a counter electrode from a discharge pin of the disc type discharge electrode according to one optional embodiments of this disclosure.
Figure 21:
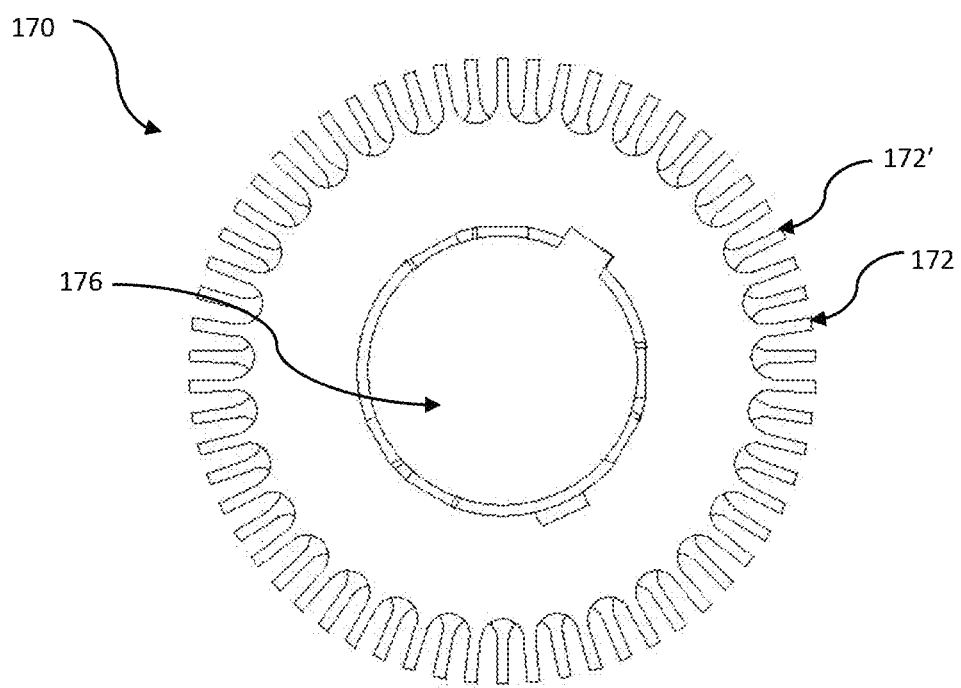
FIG. 21 is a schematic view illustrating the staggering of two disc type discharge electrodes according to one optional embodiments of this disclosure.
Figure 22:
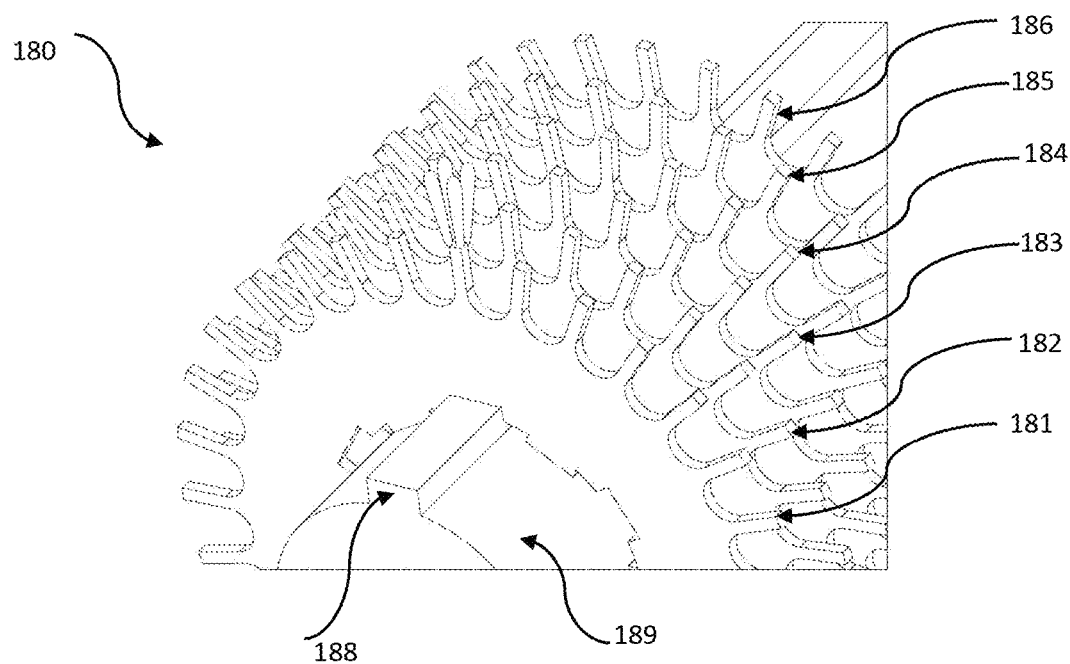
FIG. 22 is a perspective view illustrating the staggered assembly of six disc type discharge electrodes according to one optional embodiment of this disclosure.
Figure 23:
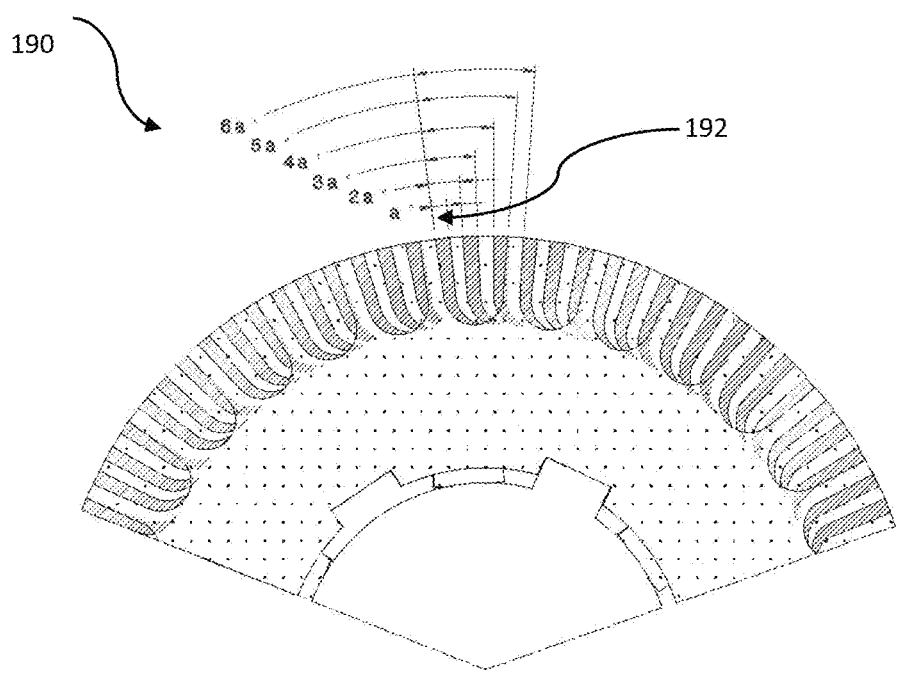
FIG. 23 is a partial view illustrating the staggering of six disc type discharge electrodes to restrict the flow through the gaps between the discharge pins according to one optional embodiment of this disclosure.
Figure 24:
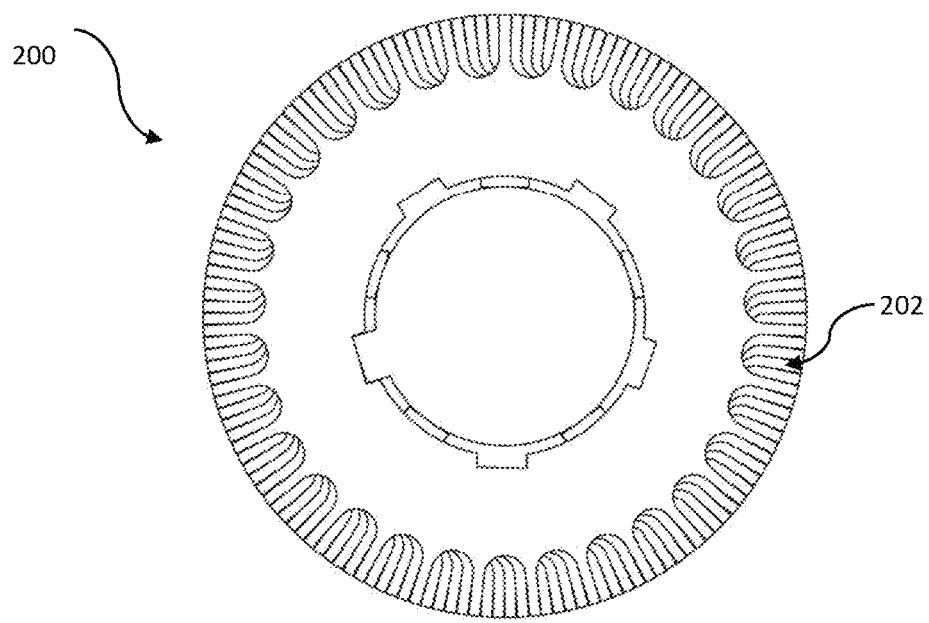
FIG. 24 is a full view illustrating the staggering of six disc type discharge electrodes to restrict the flow through the gaps between the discharge pins according to one optional embodiment of this disclosure.
Figure 25:
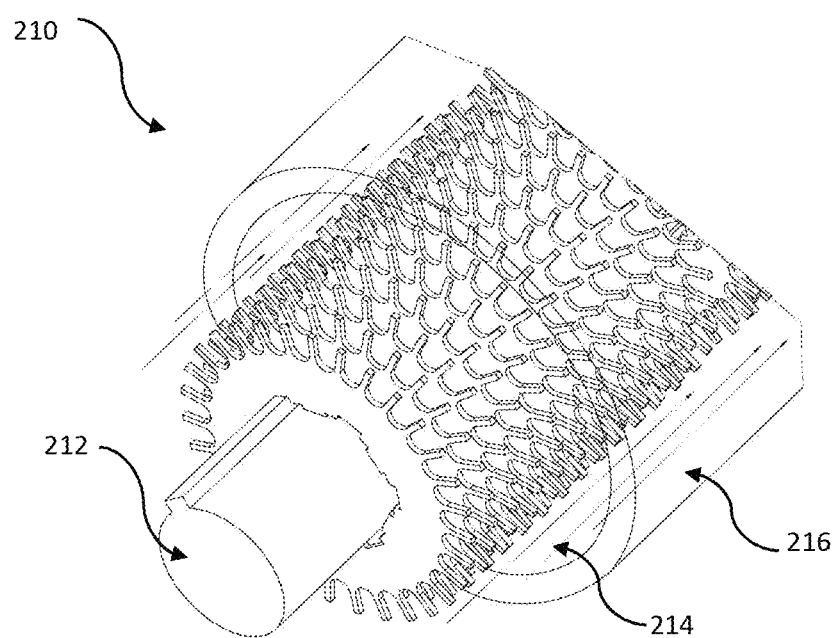
FIG. 25 is a perspective view of a disc type discharge electrode assembly deposed inside a cylindrical ground electrode according to one of the embodiments of the current disclosure.

Now referring to FIG. 19, an optional disc type discharge electrode is provided. The discharge electrode 150 comprises of discharge pins 152 having four ignition tips, arranged along the circumference of a disc. Further, the discharge electrode includes a central hole 158 and spacers 154. Although a separate spacer may optionally be used, it is preferred to have an integral spacer 154 which can be fabricated during making the central hole 158. Further key slots 156 are provided to position these electrodes on the central rod according to a predefined pattern. The number of the key slots are determined based on the diameter of the discharge electrode, size of the discharge pin and the gap between the discharge pins. Aligned with the teachings of the present disclosure, the discharge pin is designed to generate four streamers when brought to the proximity of a counter electrode and a suitable voltage is applied across them according to the teachings of the present disclosure as illustrated in FIG. 20. For illustration purpose only, assembly 160 shows a single discharge electrode fixed on the key 168 and four streamers 164 emerging from one of the discharge pins towards the counter electrode 166. However, in an actual device many discharge electrodes will be assembled together and each discharge pin would generate identical streamers to achieve the field proximity constraint taught in this disclosure. FIG. 21 illustrates a first discharge electrode superimposed on a second discharge electrode, such that the discharge pins 172 of the first electrode are in the middle of the gap between the discharge pins 172' of the second electrode. Accordingly, FIG. 22 illustrates the perspective view of six discharge electrodes 181-186 organized on the central rod 189. The organization of the discharge electrodes are done according to a predefined pattern. Although one key is used to lock the discharge electrodes in place, the key slots enable the positioning of each electrode such that a desired angle between the discharge pins of the successive electrode with respect to the previous electrode can be maintained. This is further illustrated in FIG. 23, where one cannot see through the inter pin gaps after six electrodes are assembled. In other words, if the pin width is "a", the inter pin gap is "5a", then the sixth electrode is a repeat of the first electrode. As such, a discharge pin with 0.25 mm×0.25 mm cross section would require an inter pin gap of 1.25 mm. The dimensional ratio of pin width to inter-pin gap may optionally vary and may not always stay at 1:5 ratio. The important objective here is to position the discharge pins such that the distance between the streamers is kept uniform and they are uniformly distributed on the circumference of the discharge electrode assembly. This arrangement provides an obstruction to air flow through the inter-pin gap, forcing the feed gas to interact with the streamer head for effective radical generation and the associated reactions. An exemplary assembly of electrodes is shown in FIG. 24 and as can be seen when looked from the top, the tips of the sixth electrode is not visible. In alternative aspects, instead of continuing the rotational direction of the inter-pin gap, following the pin that completes blockage of gas flow in the inter-pin gap, the directional rotation may optionally be reversed so as to form an alternating directional configuration for the inter-pin gap. FIG. 25 shows the perspective view of the electrode assembly 212 deposed concentrically inside a cylindrical counter electrode 216 and the spacing between the discharge pins is equal both in radial as well as in axial direction. This ensures uniform streamer confinement as taught in this disclosure as well as uniform interaction of the feed gas 214 with the ionization front as it passes through the discharge gap. These electrodes can be conveniently precision cut by a laser beam or electron beam or stamped for mass manufacturing. In some aspects, the spacer of the discharge electrode is optionally between 0.5 and 20 mm, optionally between 1 mm and 10 mm, optionally between 1.5 mm and 5 mm. Accordingly, the inter pin gap is optionally between 0.5 and 20 mm, optionally between 1 mm and 10 mm, optionally between 1.5 mm and 5 mm. As such, the cross section of the pin is optionally between 0.05 mm×0.05 mm and 10 mm×10 mm, optionally between 0.1 mm×0.1 mm and 2.5 mm×2.5 mm.

Figure 26:
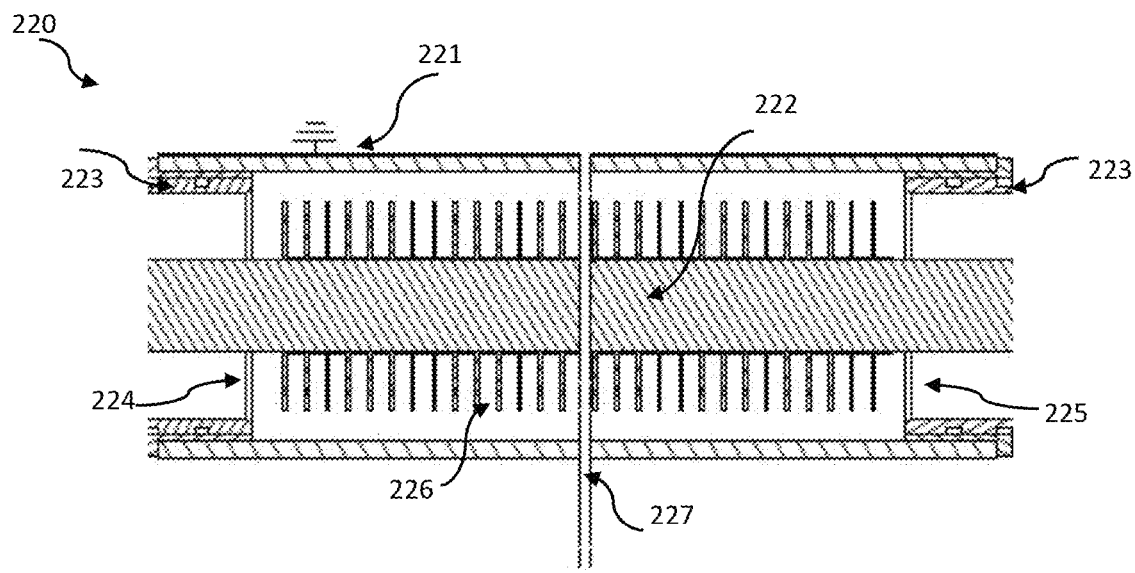
FIG. 26 is a schematic optional embodiment of the discharge device utilizing a disc type discharge electrode assembly according to the teachings of this disclosure.
Figure 27:
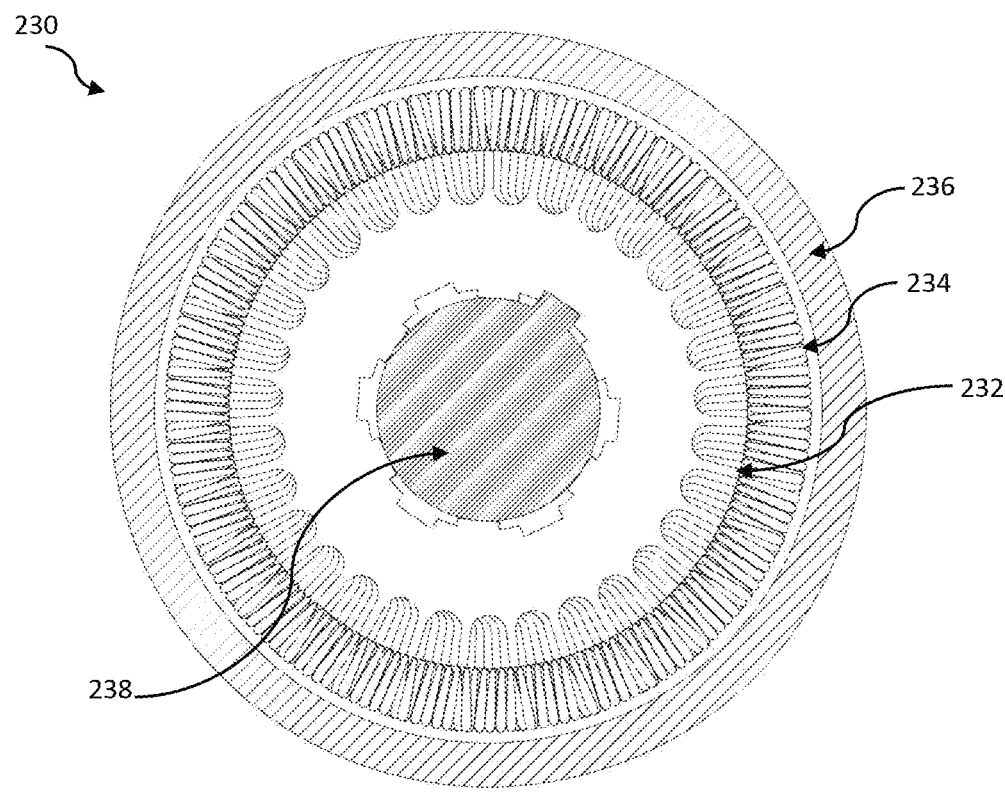
FIG. 27 is a schematic view of streamer propagation forming uniform ionization front, from a disc type discharge electrode assembly deposed inside a cylindrical counter electrode.
Figure 28:
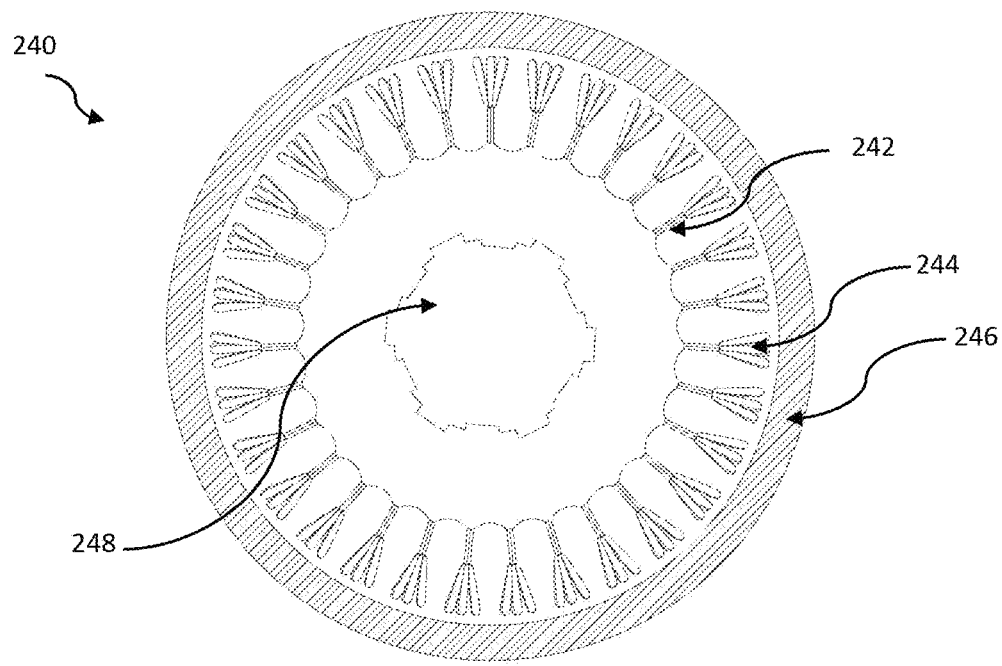
FIG. 28 is a schematic view of streamer propagation from an optional disc type discharge electrode having hexagonal discharge pins with six ignition tips.
Figure 29:
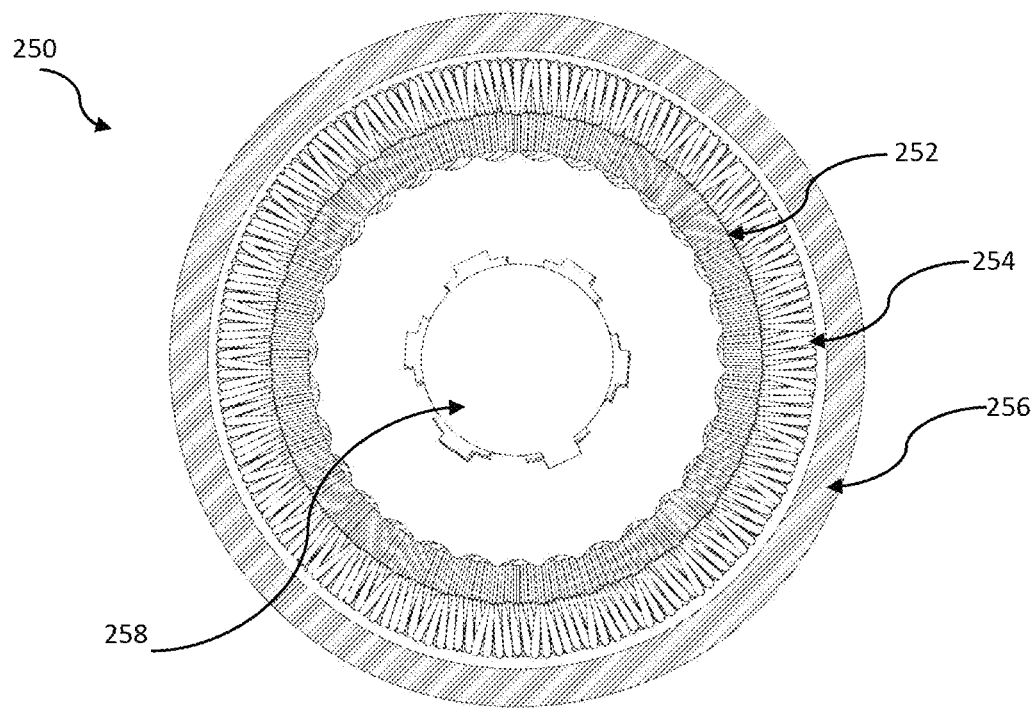
FIG. 29 is a schematic view of streamer propagation forming uniform ionization front, from an optional disc type discharge electrode assembly having hexagonal discharge pins with six ignition tips.

Referring to FIG. 26, the free radical generator of the present disclosure comprises of the discharge electrode assembly 222 comprising the disc type discharge electrode arranged according to the teachings of this disclosure, disposed coaxially inside the counter electrode 221 via the end caps 223 which electrically isolate them. When an appropriate voltage is applied, a multitude of self-constrained streamers would emerge from the discharge electrode 232 and propagate towards the counter electrode 236 presenting a uniform ionization front 234 which generates copious free radicals in the feed gas as illustrated in FIG. 27. Instead of square discharge pins one can optionally utilize hexagonal pins as illustrated in FIG. 28. Although the hexagonal pin 242 would generate six streamers 244, however fabrication of hexagonal pins through automated machining process is cumbersome. Nevertheless the streamer density for such an electrode assembly will be high as illustrated in FIG. 29.

Figure 30:
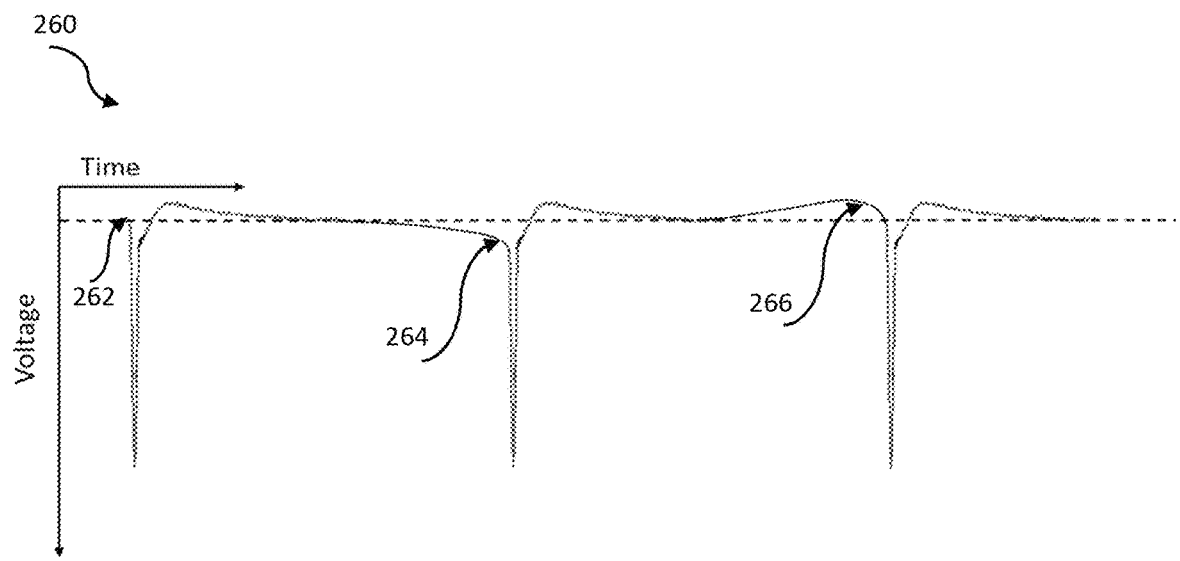
FIG. 30 is a schematic illustrating different starting voltages for successive pulses in the presence of residual charges in the discharge space.
Figure 31:
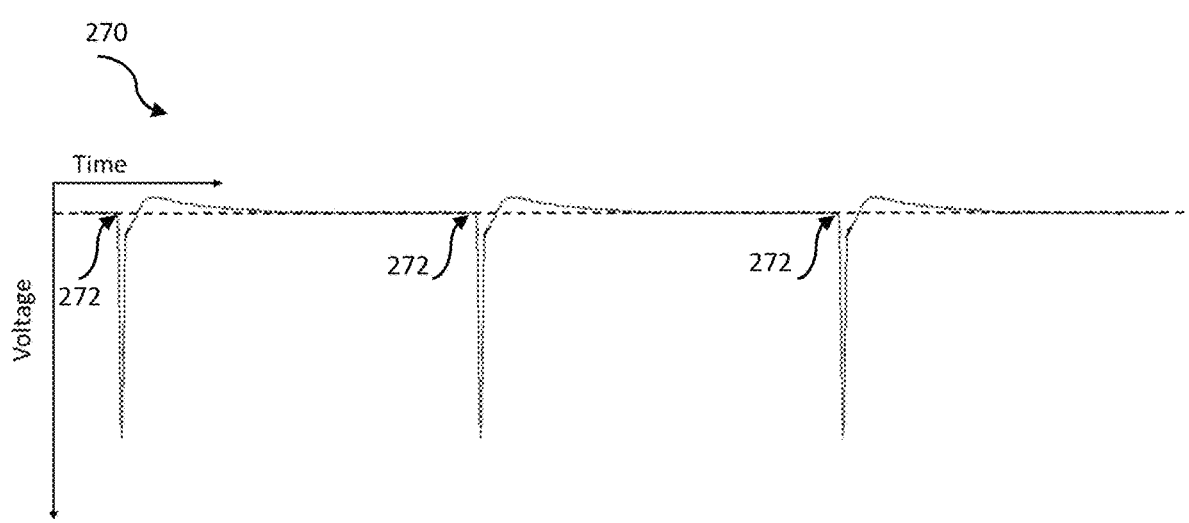
FIG. 31 is a schematic illustrating similar starting voltages for successive pulses with the application of a bias voltage between each pulse.

It will be appreciated that when the streamers traverse through the discharge space both electrons and ions will accumulate in the discharge space. The conductivity of the discharge space plays an important role on the application of successive voltage pulses for successive streamer generation. Therefore the gas flow in the discharge space plays an important role. Higher the gas flow the more effective is the drifting of the ions from the discharge space, especially from the ignition tips. On the other hand low gas velocity (~2 m/s) results in higher radical concentration. One of the design goals of a practical device is that the generator should have the ability to run at different gas flow rates to enable generation of radicals at a desired concentration. Particularly space charge build up in the discharge space plays an important role in the functioning of the device. As illustrated in FIG. 30, the typical starting voltage (262, 264, 266) for successive pulses varies due to space charge build up in the discharge space. This creates a practical issue for controlling the device operation. Due to varying resistivity, arcs may be established between electrodes even if the applied voltage pulse is accurately timed to match the streamer traverse duration. Arcing is detrimental to the device life as well as its efficiency. Accordingly, a control mechanism is disclosed here which comprises of applying a bias voltage between successive pulses to exhaust the space charge accumulated in the discharge space. Referring to FIG. 31, when a bias voltage is applied, the space charge in the discharge space is exhausted and hence brings the resistance of the discharge space to a base level, and in turn each pulse starts with a fixed voltage 272. The bias voltage is optionally between 0 and 500V compared to the actual pulse voltage (1 to 100 kV, optionally 5 to 20 kV, optionally 7 kV to 20 kV) and its magnitude depends on several parameters such as the gas flow rate and its composition, electrode design, and the applied voltage. Streamer discharge is also known to produce a gas flow. The ions within the discharge space are accelerated and, through collisions, the momentum of ions is transferred to neutrals, resulting in a gas flow. The effect of the bias voltage becomes less important when the gas velocity in the discharge space is high (>5 m/s), as the conductivity is reduced due to migration of space charge from the discharge space, more particularly from the ignition tips.

In a gas mixture containing oxygen, nitrogen and moisture, the ratio of $O^*:N^*:OH^*:H^*$ will depend upon the gas composition as well as the product of the electron energy and its probability density distribution. In a conventional volume discharge, the probability density distribution and the electron energy levels are coupled. In other words, a higher applied voltage would increase the probability density distribution, which would include electrons with energy levels spanning between ~0-10 eV or higher. Hence, in a moist gas to increase the number of $OH^*$ radicals (requires electron energies ~5 eV) one has to deal with some unwanted $O^*$ radicals (requires electron energies ~7 eV). On the other hand to generate $N^*$ radicals in a gas mixture, one will automatically generate $OH^*$ and $O^*$ radicals. Further, the radicals $O^*$, $N^*$, $OH^*$, $H^*$ may react rapidly with other molecules to form secondary radicals such as $HO^*_2$ or $O^*_3$. If contaminations such as $CO_2$, $SO_2$ or NO or $C_2H_4$ are present, $O^*$, $N^*$, $OH^*$, $H^*$, $HO^*_2$ and $O^*_3$ may react with their radicals or directly with them leading to other byproducts. For example, $N^*$ radical can reduce NO to $N_2$. The ability to tailor the type of radicals selectively enables several novel applications as will be illustrated in detail below.

Figure 32:
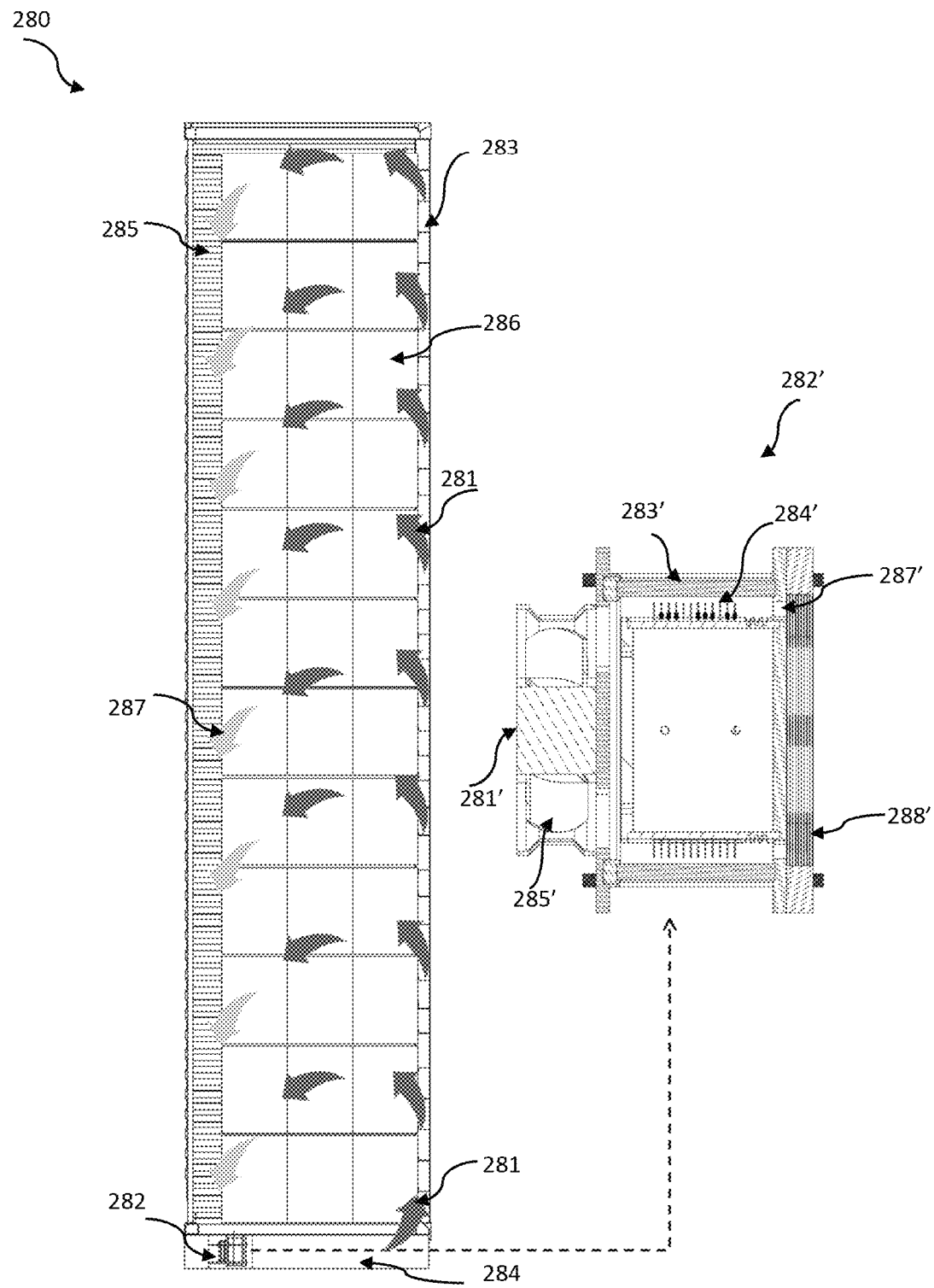
FIG. 32 is a schematic arrangement for scrubbing ethylene and microbial contaminants from a reefer container environment by an optional embodiment of the discharge device of the present disclosure.

As a way of background, the shelf life of fresh produce and fruits depends on the storage temperature as well as the storage environment. Ethylene is a natural plant hormone that has many effects such as triggering ripening and senescence. Some fruits and vegetables produce ethylene gas as a natural product of ripening and respond to this gas by accelerating their ripening. Others do not produce ethylene but are very sensitive to it. For sensitive produce, minute quantities of ethylene gas will greatly accelerate the ripening process even at low storage temperatures. In prolonged air or Controlled Atmospheres (CA) storage, fruits and produces undergo ethylene induced softening and in some cases leads to ethylene induced skin cell death. Maintaining very low ethylene concentrations during the early stages of storage are critical in delaying softening during prolonged storage. Further, the microbial growth in a storage environment also promotes rotting and spoilage. Therefore, decontaminating the storage environment is critical to achieve longer shelf-life. Now referring to FIG. 32, although there are many variations, a typical refrigerated (reefer) transportation container includes a refrigeration compartment 284, through which the return air 287 from the storage compartment passes through a heat exchanger releasing its excess heat load and the resulting cold air 281 recirculates back to the storage compartment where the produce 286 is stored. Typically, the container bottom comprises of air distribution channels 283 which distribute the cold air 281 through the produce load 286. The cold air 281 while removing heat from the produce, also picks up the naturally formed ethylene as well as microorganisms on the produce. The contaminated air 287 returns through the air collection path 285 back to the refrigeration compartment. Although, the refrigeration system removes the heat, the ethylene and microorganism load recycles back to storage chamber in the absence of any intervention methodology. Eventually, the ethylene level keeps building up and causes irreparable damage to the produce. A method to remove ethylene and microorganism from the air stream deploying the radical generator is disclosed here. This method comprises disposing free radical generator 282 of this disclosure in the air circulation path of the reefer transportation container to scrub ethylene and microbial contaminants. The free radical generator 282 optionally includes a fan/blower 285' which draws contaminated air 281' from the air circulation stream and pushes it through the discharge space formed by the discharge electrode assembly 284' and the counter electrode 283'. Optionally, the counter electrode may contain catalytic material/s to augment catalytic reaction. Optionally, the circulation blower of the refrigeration system may be utilized to direct air through the radical generator. Optionally, the discharge device 282' is deployed inside the storage compartment. As the contaminated air passes through the discharge space depending upon its composition many free radicals as well as metastables from in the discharge space, which eventually lead to other forms of chemical reactions. The free radicals also destroy the microorganisms in the air stream. Typically the fresh produce/fruits storage environment contains high relative humidity in the order of 85-90%. The water molecules dissociate into $OH^*$ radicals and require electron energies in the order of ~5 eV. Incidentally, ethylene $C_2H_4$ also has a dissociation energy in the same range (~4.5 eV). In addition to these, $O^*$ radicals also form in the discharge space. Further, vegetables and fruit respire; they take in oxygen ($O_2$) and give off carbon dioxide ($CO_2$). $CO_2$ in the return air may also dissociate in the discharge space into CO and O. There are several pathways for ethylene and $CO_2$ to convert into other chemical forms in the discharge space, particularly in the presence of O* or OH* radicals as well as their secondary radicals. In addition to the free radicals, the discharge space optionally also generates UV, which together decontaminate the air stream from microorganisms. The free radical generator 282' optionally includes a filter 288' through which the treated air 287' from the discharge space is filtered. The filter 288' optionally absorbs the byproducts of the complex chemical reactions occurring in the discharge space. For example, due to the presence of oxygen usually ozone forms in the discharge space. Although a low level of ozone in the treated air can be beneficial in decontaminating the surface of the produce, many produce and fruits are sensitive to elevated level of ozone. Filter 288' optionally destroys ozone. There are many ways to design this filter to absorb/destroy different compounds and one optional method is to adopt a catalytic path which utilizes a particulate bed such as manganese dioxide/copper oxide. Optionally the radical generator includes a bypass (not shown) mechanism which avoids passing the treated air through the catalytic filter. In this case, some free radicals such as OH* and $O_3$ is sent into the container for beneficial surface decontamination. Although the produce and fruits storage example here is illustrated via reefer container, the methodology can effectively be utilized in conventional stationary cold storages or any other storage space following the teachings of this disclosure.

Figure 33:
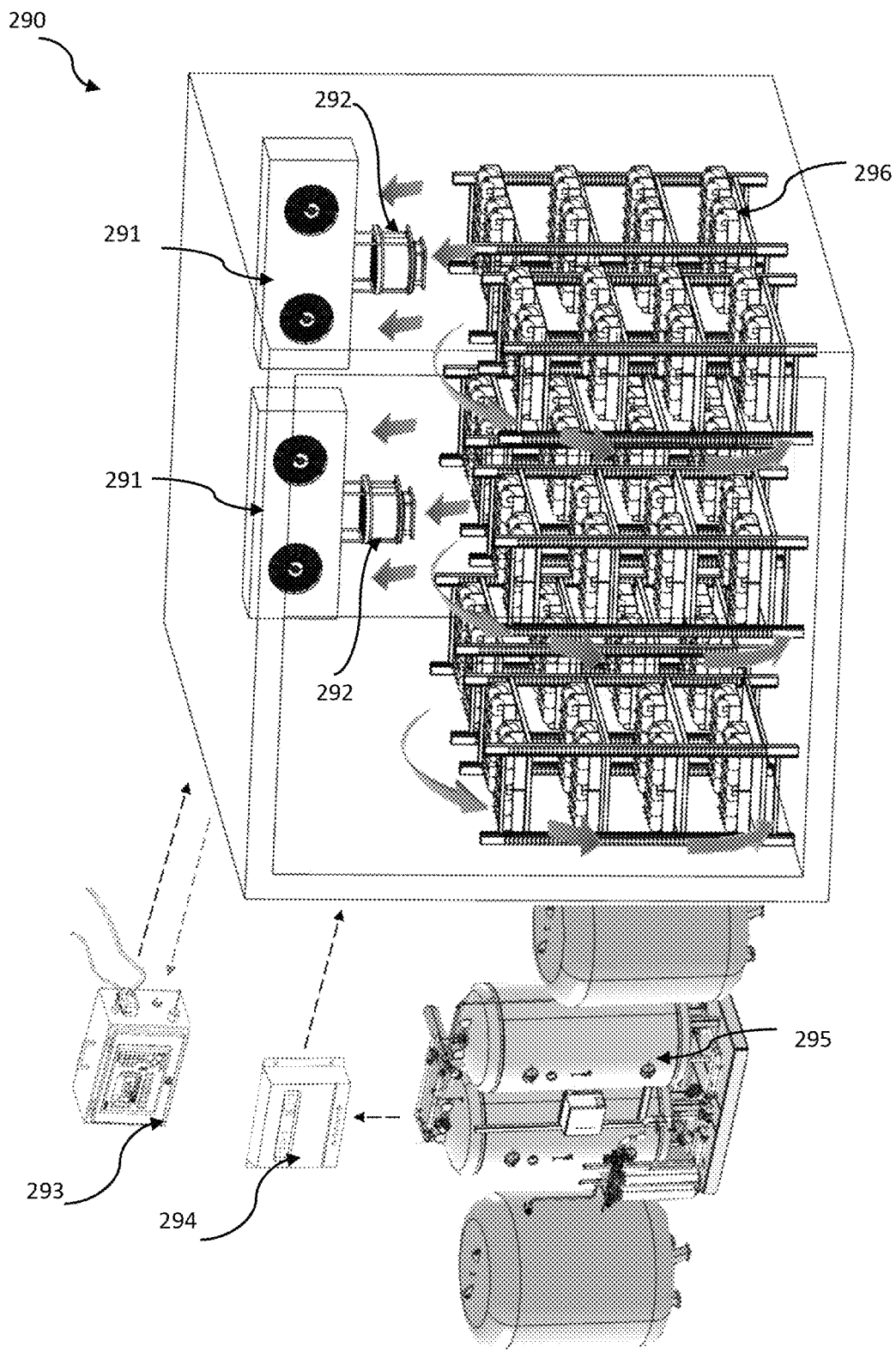
FIG. 33 is a schematic arrangement for scrubbing ethylene, CO2 and microbial contaminants from a controlled atmosphere (CA) storage environment by an optional embodiment of the discharge device of the present disclosure.

As a way of background, controlled atmospheric storage (CA) is a preferred alternative to standard refrigerated cold storage, whereby the level of oxygen is reduced and $CO_2$ is increased. Exposure of fresh produce to low $O_2$ and/or elevated $CO_2$ atmospheres within a range tolerated by each commodity reduces their respiration and ethylene production rates; however, outside this range respiration and ethylene production rates can be stimulated, indicating a stress response. This stress can contribute to incidence of physiological disorders and increased susceptibility to decay. Elevated $CO_2$-induced stresses are additive to and sometimes synergistic with stresses caused by low $O_2$, physical or chemical injuries, and exposure to temperatures, relative humidity (RH), and/or $C_2H_4$ concentrations outside the optimum range for the commodity. Therefore, the level of $CO_2$, $O_2$, RH and $C_2H_4$ are carefully controlled within a range for CA. Under optimal CA conditions, many produce types can be stored for 2 to 4 times longer than usual. Typical CA storage facility comprises of $CO_2$, $O_2$, and $C_2H_4$ scrubbers in addition to temperature and humidity control systems. Now referring to FIG. 33, a method to control $C_2H_4$ and $CO_2$ in a CA storage environment is disclosed. The method 290 includes deploying free radical generator 292 to direct the contaminated air through the discharge space to chemically convert the ethylene and $CO_2$ to products that can be absorbed in the filter as discussed earlier. Particular attention is drawn to the operation of the free radical generator in an oxygen deficient environment. U.S. Pat. Nos. 8,293,171 and 8,388,900 have disclosed techniques utilize ozone to convert ethylene into $CO_2$. The rate of reaction between ethylene and ozone is kinetically slow and it requires high ozone level to achieve reasonable conversion rate. Further, such techniques will not work in an oxygen deficient environment like CA. Further, the byproduct $CO_2$ puts additional load on the $CO_2$ scrubber. However, the disclosed method here is not dependent on oxygen as the CA atmosphere contains significant moisture which can optionally be dissociated into OH* radicals for the conversion of $C_2H_4$ which also dissociates due to electron collision in the discharge space. Kinetically, the conversion process is faster and works at a very low concentration of radicals. Simultaneously, $CO_2$ conversion also can be obtained and possibly eliminate the need for separate $CO_2$ scrubber.

Figure 34:
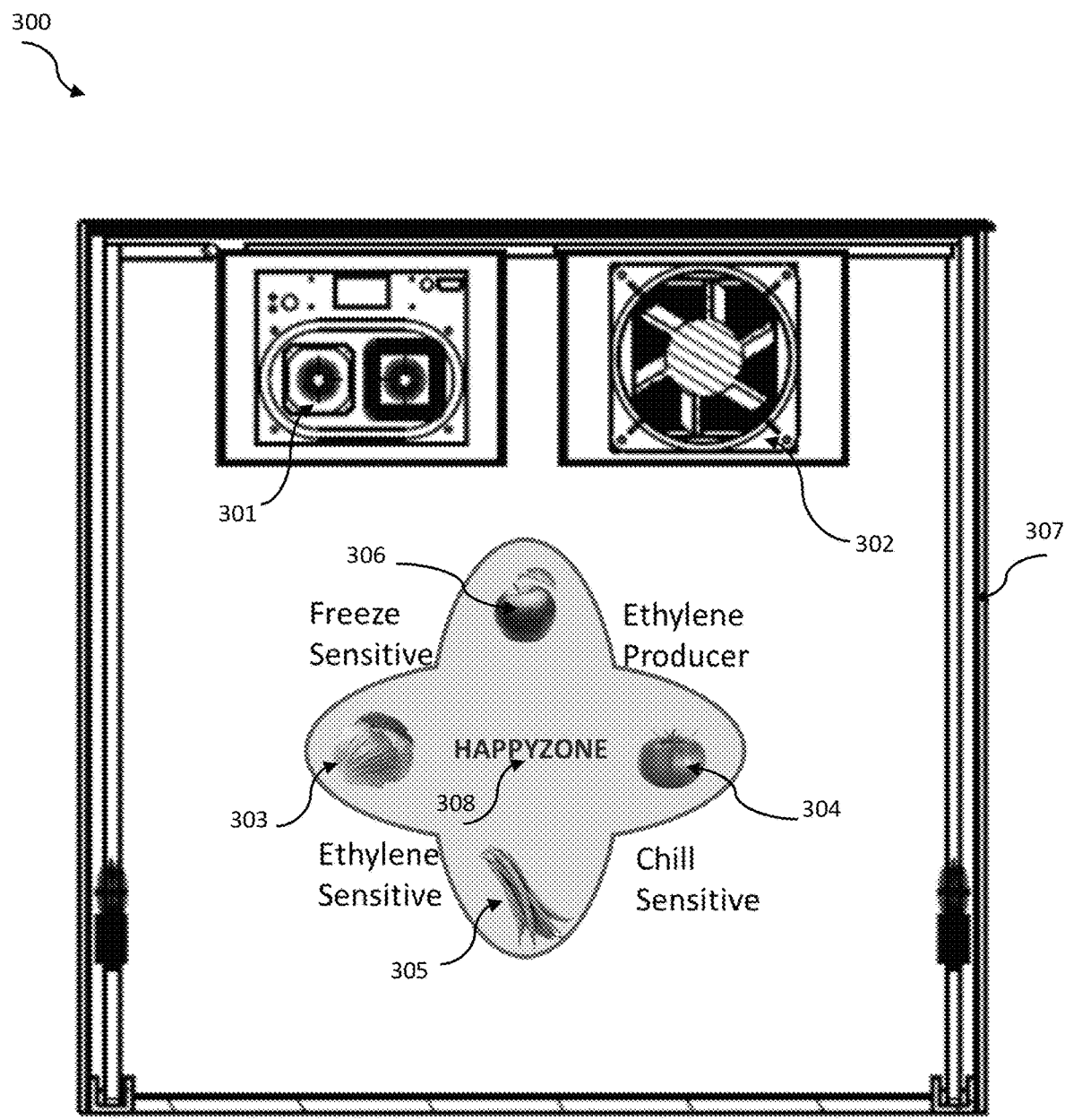
FIG. 34 is a schematic arrangement for scrubbing ethylene and microbial contaminants from a non-refrigerated storage environment by an optional embodiment of the discharge device of the present disclosure.
Figure 35:
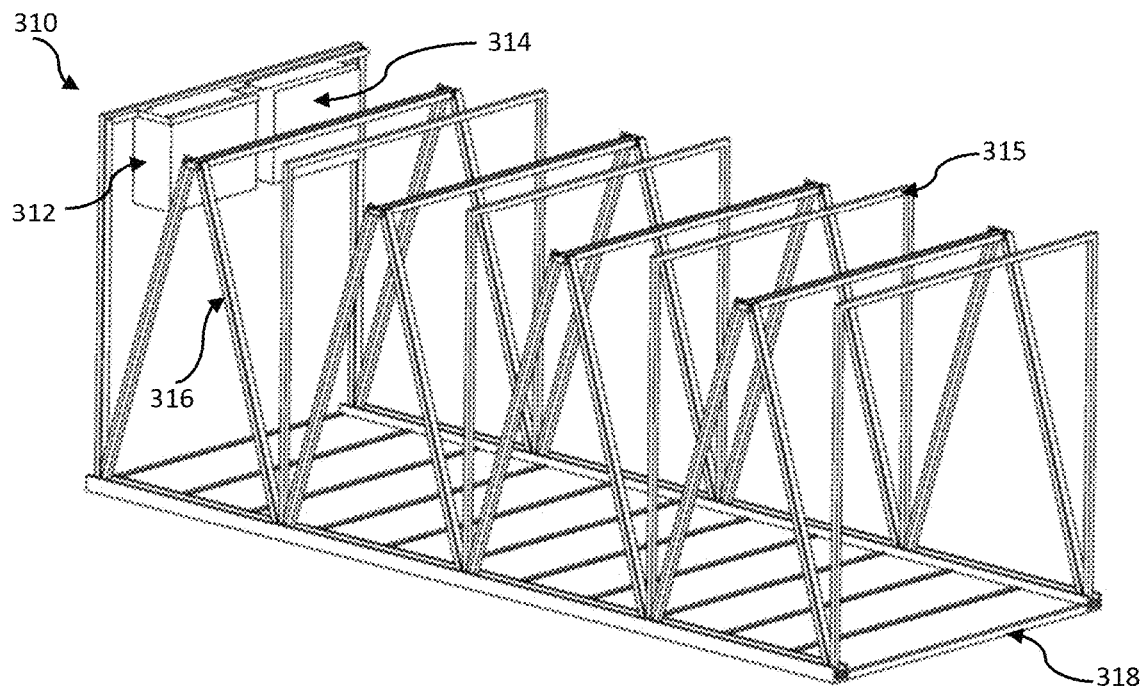
FIG. 35 is a schematic optional arrangement for a retractable frame for collecting air and distributing air in a retractable shade.
Figure 36:
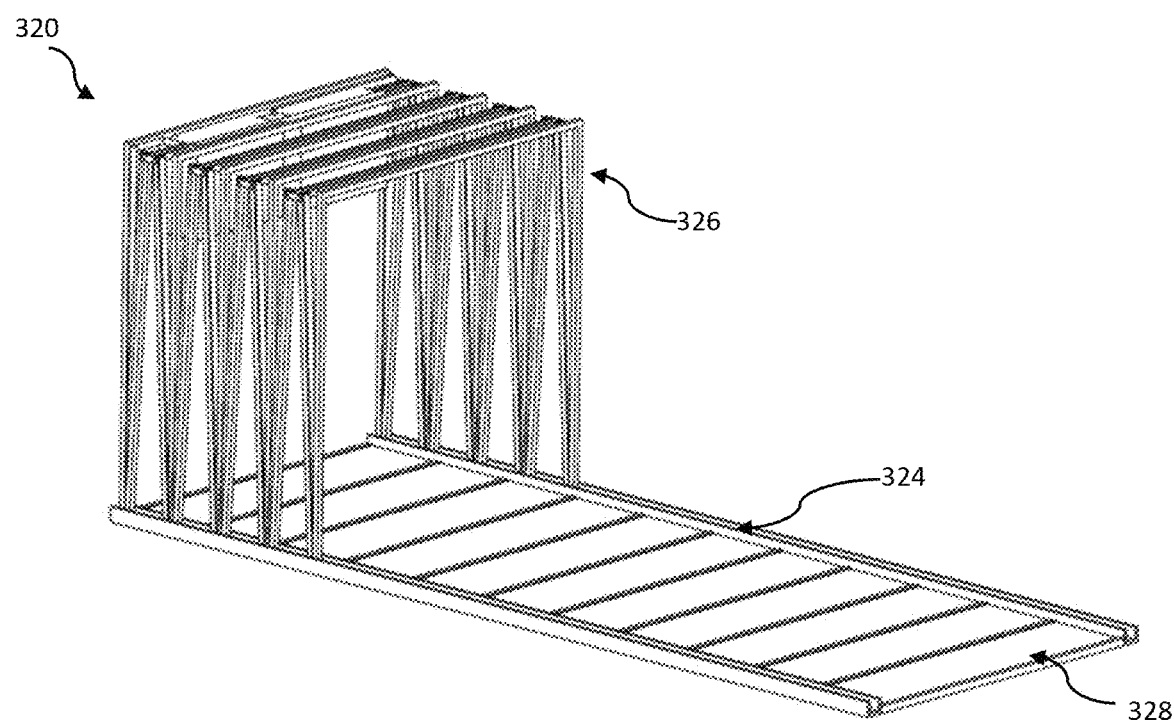
FIG. 36 is a schematic optional arrangement for the retractable frame in closed position.
Figure 37:
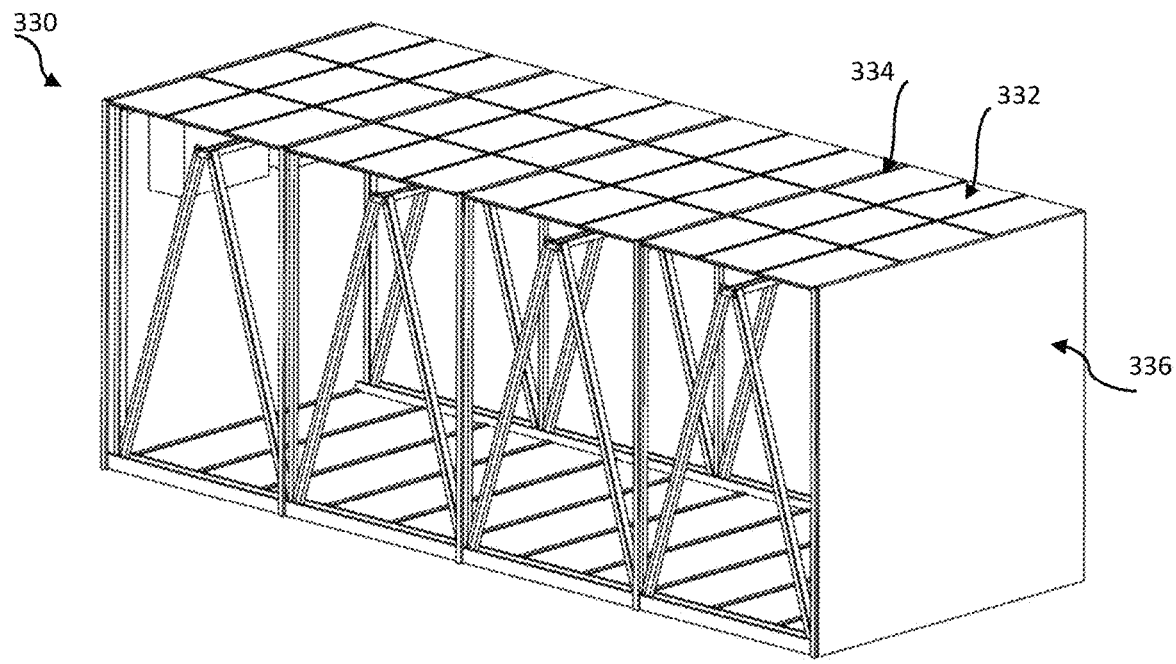
FIG. 37 is a schematic arrangement for retractable storage shade with optional solar panel.
Figure 38:
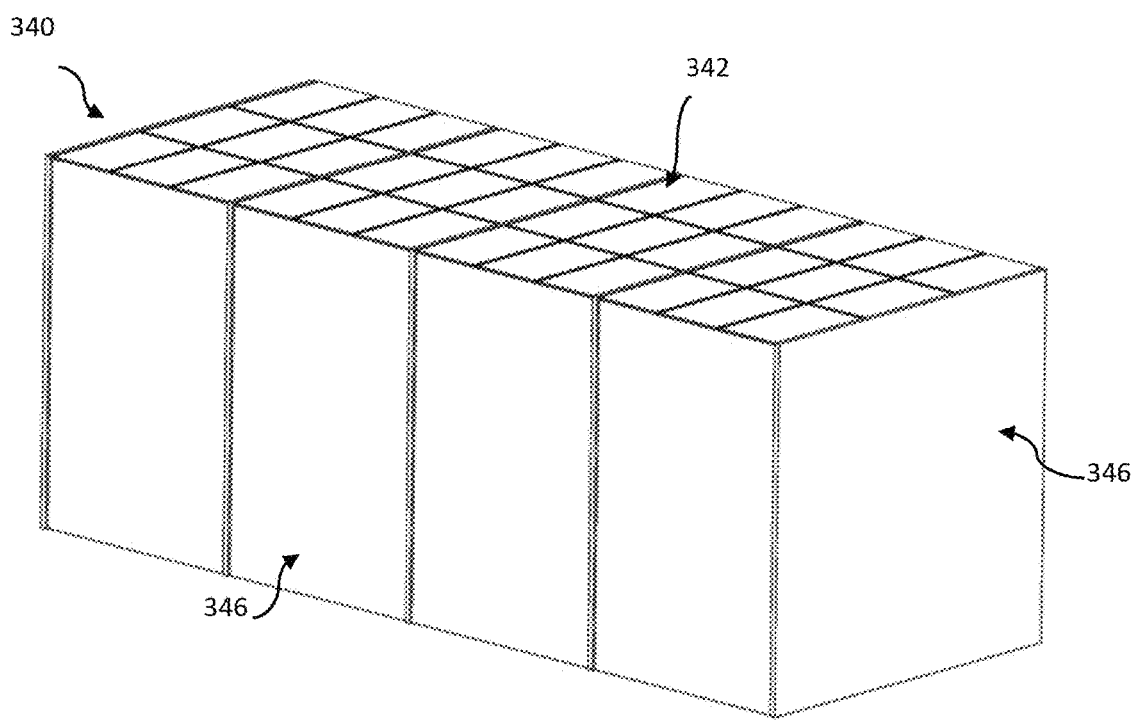
FIG. 38 is a schematic arrangement for an off-grid retractable storage shade having the discharge device of the current disclosure to scrub ethylene and microbial contaminants.

Although, refrigerated containers and cold storages have become the norm for fresh produce logistics in the developed world, many parts of the world still rely on non-refrigerated storage and transportation. To this end, a method to manage ethylene and microorganism scrubbing in non-refrigerated enclosures to extend shelf life is disclosed here. Referring to FIG. 34, the enclosure 300 may include a radical generator 301 of this disclosure, an optional evaporative cooler 302 and optionally a retractable frame 307. As a way of background, fresh produce and fruits have different sensitivities. For example, apples and tomatoes are ethylene producers. However, apples are typically stored around ~32° F. to minimize metabolic activities and ethylene production but, tomatoes cannot be stored at those temperatures as they are chill sensitive. Similarly, cabbages and beans don't produce ethylene but are highly sensitive to ethylene. Further, cabbage is typically stored around ~32° F., while beans are chill sensitive. With a technique for removing ethylene and microorganisms in place, both ethylene producers and ethylene sensitive produce can be co-stored to extend their shelf life, although in the absence of a temperature management system, the utility will be limited. To this end, evaporative coolers can be used and can optionally maintain the temperature around ~50-55° F. Thus, an economic storage environment termed as "Happyzone" for co-storing freeze sensitive, chill sensitive, ethylene producer and ethylene sensitive products is created. Although this temperature is not ideal for freeze sensitive products like apple and cabbage, the ability to remove ethylene from the environment provides the next best alternative to cold chain logistics. Now referring to FIG. 35, an optional retractable frame that provides support for a flexible cover such as tarpaulin as well as to collect the contaminated air and distribute treated air inside the enclosure is disclosed. The retractable frame slides on a flatbed 318 and includes two channels, out of which the distribution channel 316 is connected to the output of the radical generator which distributes treated air into the enclosure and the collector channel 315 is connected to the inlet fan/blower of the radical generator which supplies contaminated air to the reactor. In some aspects, unlike a refrigerated space, the air inside the enclosure doesn't recirculate. The distribution and collection channels of the retractable frame provides that function here. The retracted view of the enclosure frame is shown in FIG. 36. To operate the radical generator as well as the evaporative cooler, one can draw electricity from the wall or optionally use a battery storage system along with solar panels. The grid independence enables one to use the enclosure for transportation as well as storage in remote places where electricity may not be available. FIG. 37 illustrates the solar panel 332 integration on the roof of the enclosure. Since this needs to be retractable, the panels are designed such that it folds 334 along with the underlying frame. FIG. 38 illustrate the complete enclosure comprising of top solar panels 342, side tarpaulin 346 and the internal radical generator, air distribution retractable frame and an optional evaporative cooler. It is to be noted that the evaporative coolers need a water supply to function. Especially, for transportation use of the enclosure water can be optionally generated by thermoelectric principles from air which will be discussed below.

Figure 39:
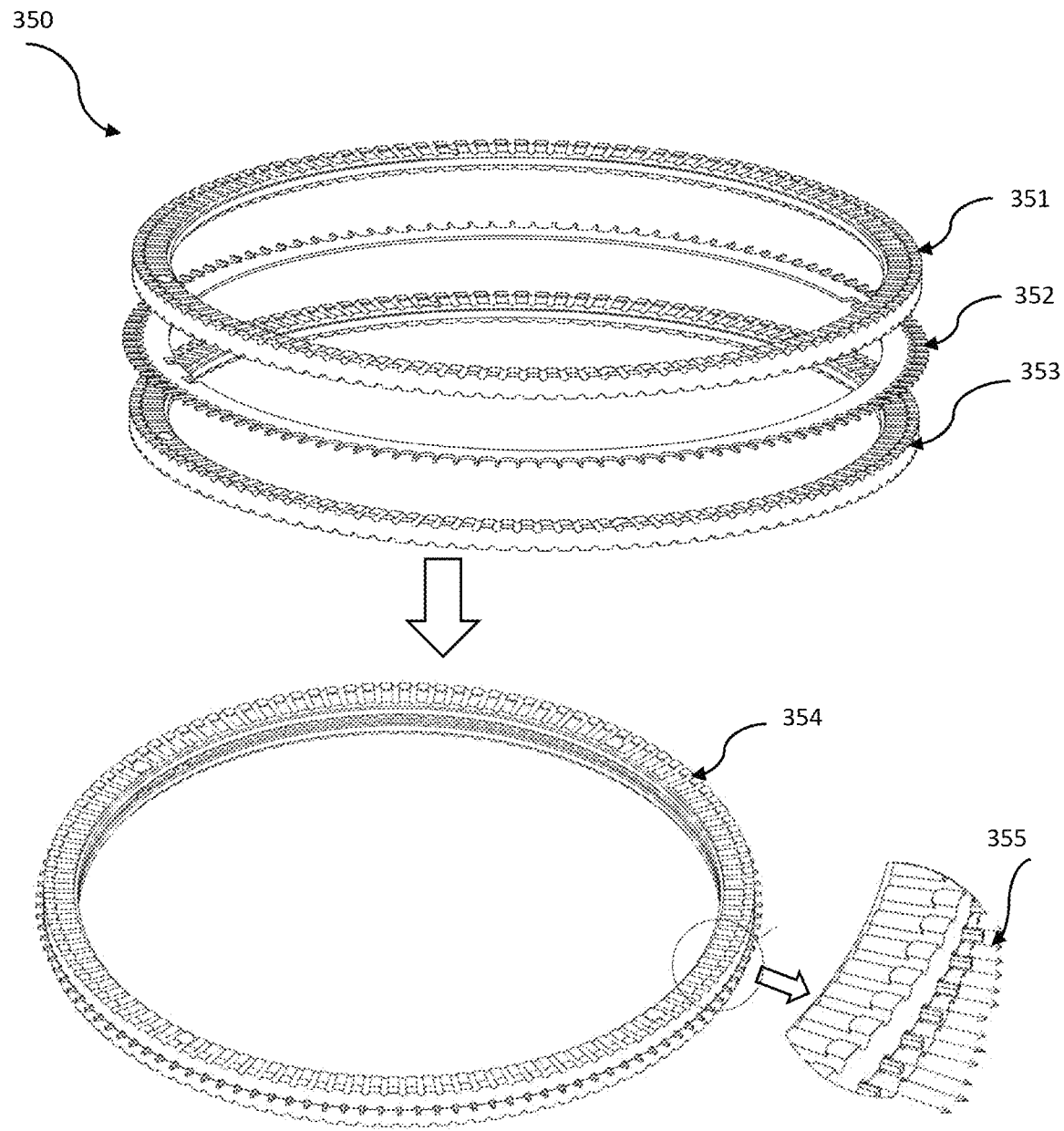
FIG. 39 is a schematic optional arrangement for disc type discharge electrode with diverging discharge pins encapsulated in a cassette to provide airflow around the discharge pins.
Figure 40:
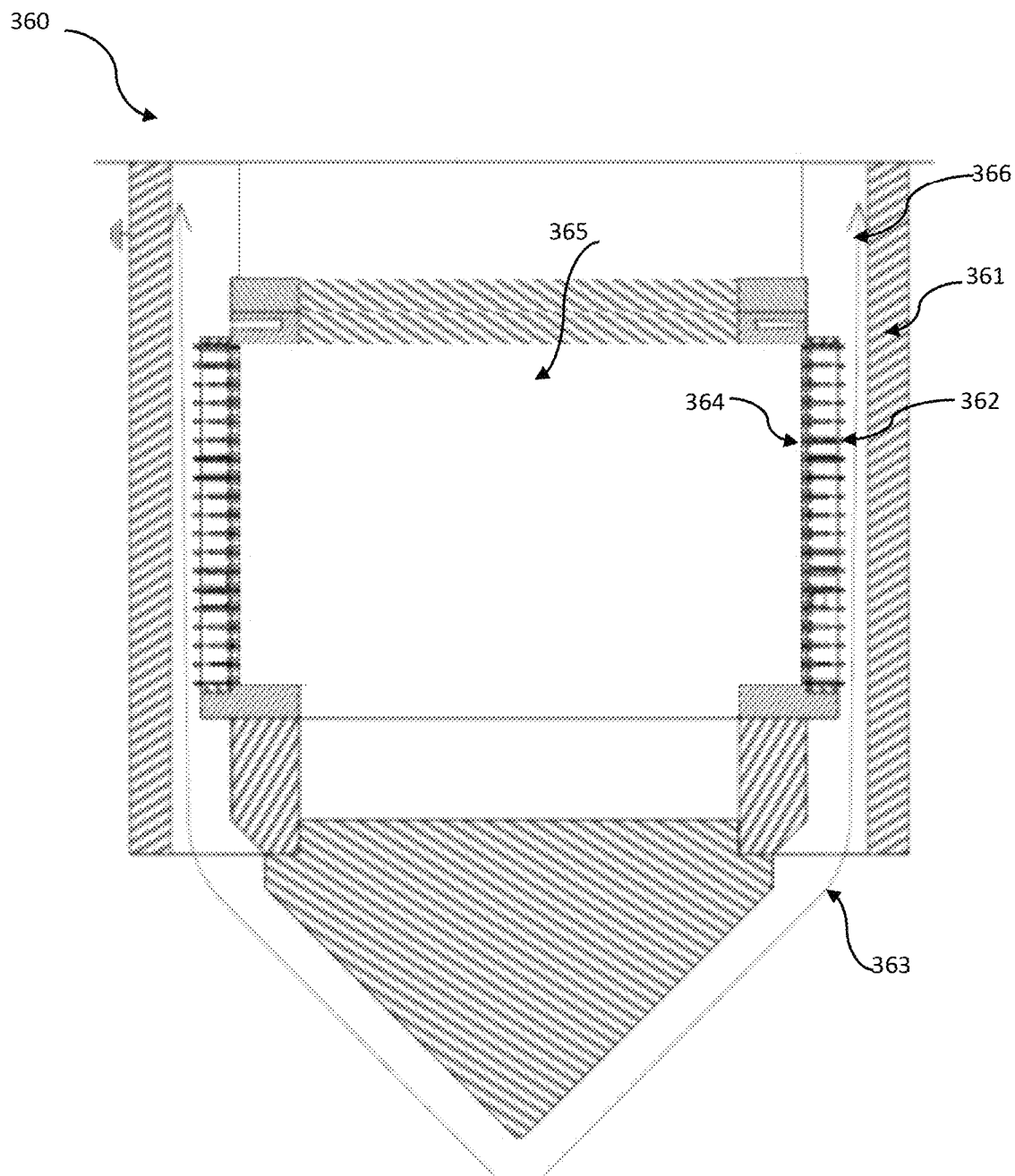
FIG. 40 is a schematic arrangement for a discharge device operating with a gas feed optionally having suspended liquid droplets (or a mist) and diverging discharge pins according to the teachings of the present disclosure.
Figure 41:
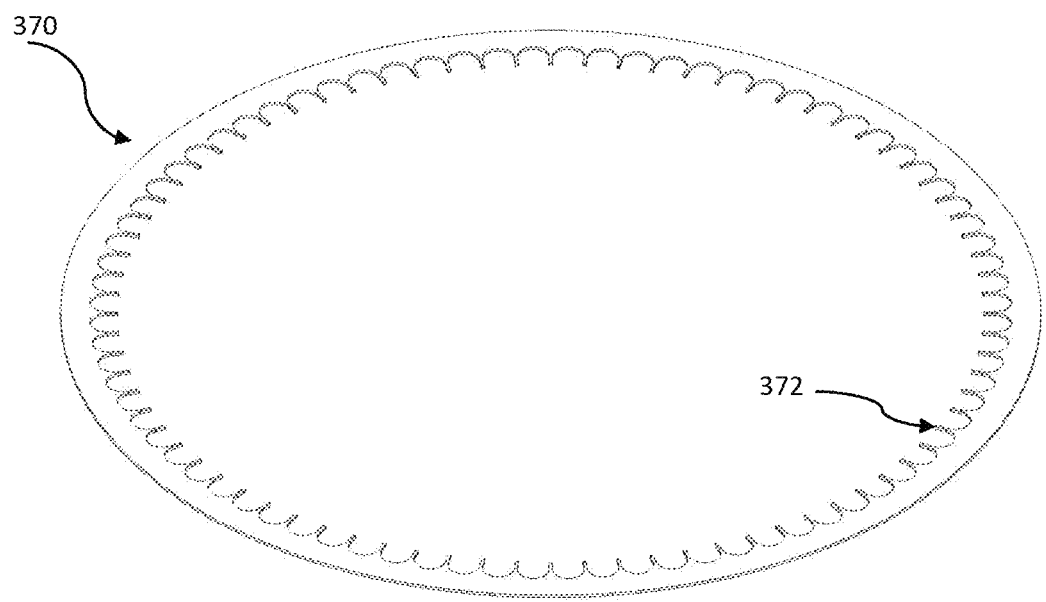
FIG. 41 is a schematic view of a disc type discharge electrode having converging discharge pins.

As noted above the presence of humidity in the feed gas plays an important role on the selectivity of the radicals to be generated by the radical generator as well as the subsequent reactions involving those radicals. For example, the O* and OH* radicals may react rapidly with other molecules to form secondary radicals such as $HO_2^*$ or $O_3^*$. But, the effective water content in the air is dependent on the temperature and pressure and accordingly the OH* and the related radical concentration will depend on the effective water content. For example, at one atmospheric pressure, the specific humidity is 10 g(w)/Kg(air) at 15° C., whereas it increases to 49.8 g(w)/Kg(air) at 40° C. Optionally, the addition of moisture beyond the saturation point or in other words feeding a mist to the discharge space can lead to innovative applications. However, special care must be taken to prevent the accumulation of liquid at the ignition tips for reliable and continuous operation of the discharge device. To this end, FIG. 39, illustrates a cassette design to enable airflow around the discharge pins. The cassette assembly 350, comprises of two patterned cover slips 351 and 353, which houses the discharge electrode 352. When closed, the assembly 354 creates radial flow paths from inside to outside around each discharge pin 355. This radial flow prevents accumulation of liquid at the ignition tips. It is to be noted that accumulation of liquid at the ignition tips affects the discharge characteristics and often leads to arcing and electrode damage. The encapsulated electrodes can now be deployed to fabricate a fumigation device that can utilize a mist containing varying amount of liquid droplets as the feed as illustrated in FIG. 40. The fumigation device 360 includes a discharge electrode assembly 365 comprising of encapsulated discharge electrodes 364, a counter electrode 361 facing the ignition tips 362, and a misting source 363. Accessories such as the power supply, pumps and misting device and fittings etc., are not shown here. The discharge electrode assembly 365 is closed from the top and bottom forming a chamber that can be pressurized to enable air flow around the discharge pins through the radial flow path disclosed here. When the mist passes through the discharge space, many complex radicals are formed which are carried by the outgoing mist 366 and can be deployed in many applications as illustrated below.

FIG. 41 illustrates an optional discharge electrode design where the discharge pins 372 are directed towards the center of the disc. Here the discharge pins are convergent and the tip to tip distance is smaller compared to an equivalent electrode 352. As shown in FIG. 42, these electrodes can be encapsulated in a cassette 380 to provide airflow 382 around the convergent discharge pins. Utilizing the cassette assembly 380 a fumigation device can be fabricated following the teachings of this disclosure. FIG. 43 illustrates an exemplary fumigation device deploying the convergent discharge electrode assembly 392, the counter electrode 391, the air chamber 394 and the misting source 393. The outgoing mist can be utilized for a variety of applications. It is to be noted that the characteristics of the outgoing mist will depend on several parameters such as the carrier gas, the droplet size and content, the applied energy and the interaction time. Accordingly, one can design selective mist characteristics for a given application. The droplet size in the feed gas may optionally vary between 0.2 and 45 microns. As such, the droplet size is optionally between 0.4 and 9 microns. High air velocity through the discharge space may avoid droplet accumulation at the ignition tips. The air velocity in the discharge space may optionally vary between 10 m/s and 200 m/s, optionally between 50 and 150 m/s, optionally between 75 m/s and 125 m/s. At 25° C. and atmospheric pressure, the water content in the feed gas is optionally between 10 g per kg of air and 200 g per kg of air, optionally between 40 g per kg of air and 100 g per kg of air.

Now attention is drawn to the streamer interaction with the mist and the associated chemical reactions and species generation. Depending on the type of discharge (positive and negative), its energy, and the chemical composition of the surrounding environment (of both gas and liquid phases), various types of chemical reactions can be initiated and a number of primary and secondary species can be formed by the streamers in the gas and at the gas-liquid (water) interface, which can dissolve into the liquid and thus provide the chemical and biocidal characteristics to the mist. It is to be noted that besides dissociation of water leading to $H_2O+e^-\rightarrow OH^*+H^*$, other collision events are likely to occur due to the presence of $O_2$ and $N_2$ in the gas stream. For example, the oxygen radicals will possibly contribute towards OH* radical generation through the following:

$$O(^3P)+O_2+M\rightarrow O_3+M(M=N_2, O_2, O_3 \text{ or } H_2O) \quad (6)$$

$$O_3+OH^-\rightarrow O_3^{*-}+OH^* \quad (7)$$

$$O_3^{*-}\rightarrow O^{*-}+O_2 \quad (8)$$

$$O^{*-}+H_2O\rightarrow HO^*+HO^- \quad (9)$$

$$O(^1D)+H_2O\rightarrow OH^*+OH^* \quad (10)$$

where, $O(^1D)$ and $O(^3P)$ are excited states of atomic oxygen, M is an arbitrary third-body collider, for example, $N_2$ or $O_2$, as a third body is required here to conserve energy and momentum. Note that $O(^1D)$ can lose its excessive energy due to relaxation collision with gas molecules via $O(^1D)+M\rightarrow O(^3P)+M$, but, in the presence of high level of moisture many events involving $O(^1D)+H_2O\rightarrow OH^*+OH^*$ reaction will occur. Although, OH* radicals can be consumed in many possible reactions, $H_2O_2$ formation in the condensed moisture can occurs through the following;

$$OH^*+OH^*+M\rightarrow H_2O_2+M(M=N_2, O_2, H_2O) \quad (11)$$

$$HO_2^*+HO_2^*\rightarrow H_2O_2+O_2 \quad (12)$$

$$HO_2^*+H_2O\rightarrow H_2O_2+OH^* \quad (13)$$

and, $HO^*_2$ secondary radical formation occurs through the following;

$$O_3+OH^*\rightarrow HO_2^*+O_2 \quad (14)$$

$$OH^*+OH^*\rightarrow HO_2^*+H^* \quad (15)$$

$$OH^*+H_2O_2\rightarrow HO_2^*+H_2O \quad (16)$$

$$O^*+H_2O_2\rightarrow HO_2^*+OH^* \quad (17)$$

necessitating the formation of OH* radical. Among various chemical species produced by the streamer at the oxygen gas-liquid (water) environment, OH* radical, atomic oxygen, ozone and hydrogen peroxide are the main reactive oxygen species (ROS) generally accepted to play the dominant role in the chemical and bio-inactivation process, particularly at lower pH levels induced by the streamer interaction.

In the presence of nitrogen (e.g. air), the transient species produced at the gas-liquid interfaces will also include reactive nitrogen species (RNS) such as NO* and $NO_2$*, and peroxynitrite. The transient species are highly cytotoxic. However, they are difficult to measure due to their short lifetimes and fast disproportionation in the streamer/liquid systems. Because of the complexity of the reactions, giving rise to both stable and non-stable intermediates and reactions products, biological effects in streamer-treated mist are the result of complex interactions at the streamer/gas-liquid interface and subsequent reactions in the liquid droplets. The exact mechanism and contribution of these species in the biological effect of the mist are not yet fully understood. There are possible synergistic effects of the processes occurring during the discharge, and post-discharge reactions in the streamer-treated mist. Prolonged antibacterial activity of streamer-treated aqueous solutions has been observed, and without being limited to one particular theory, probably involve the presence of long-lived reactive species transferred from the discharge into the liquid. These post-discharge reactions may contribute significantly to the biological effects induced by these types of electrical discharge. Formation of nitrogen transient species at the gas-liquid interface has been evidenced mainly indirectly through the detection of nitrogen products $NO^-_2$ and $NO^-_3$ in the streamer treated water.

The formation of transient species (OH*, $NO_2$* and NO* radicals) and long-lived chemical products ($O_3$, $H_2O_2$, $NO^-_3$ and $NO^-_2$) produced by the gaseous discharge at the gas-liquid interface and directly in the liquid and the aqueous phase chemistry induced by these species contribute to the chemical and biocidal effects to the mist. Depending upon the application one can select a desired gas environment to achieve specific characteristics. Now referring to FIG. 44, a fumigation device 400 including several discharge devices 401, a common mist intake 402, a water reservoir 405 and the control unit 406 is disclosed. The misting chamber also includes fans 403 to blow the mist through the intake 402 and the discharge devices. Optionally, the discharge devices may include individual fans to achieve further control in the flow and operation. The control unit includes power supply and optionally sensors and programmable interfaces for the device operation. The cross section view of the exemplary device is illustrated in FIG. 45. The mist generation system 417 is submerged in the liquid 418. The misting technique may include ultrasonic atomization, heating and evaporation or simply air atomization. Once the mist is generated the blower fans 415 lift the mist through the column 416 and feed to the discharge devices. The column 416 ensures that heavier droplets fall back to the reservoir and only a desired size fraction is fed to the discharge devices. Each discharge device 412 optionally includes a fan 414. The fan 414 provides additional control to the device operation. In a given application it may be desired to run only a selected number of discharge devices. Under the circumstance, only the active discharge devices receive the mist through their individual fans. Additionally, the blower fans 415 may optionally include a heater. The heated air increases the saturation limit and hence carries a lot of moisture with it. Upon cooling the saturated moisture condenses to droplets carrying radicals that can provide functional applications. The device assembly can be mounted on a mobile platform with remote operational capability as illustrated in FIG. 46. The mobile assembly 420 includes the fumigation device 422, the accessories assembly 424, X-Y-θ translational motion system 426 and the vertical lift 428. Due to high level of active radicals generated for disinfection applications, it is desired to have remote operational capability without exposure to working personnel. There are many possible pathways to achieve sophisticated motion control for the device.

An exemplary application of the fumigation device of this disclosure is illustrated in FIG. 47. A fumigation device 432 with remote operational capability is deposed in a medical facility for sanitization against harmful microorganisms. As a way of background, antibiotic resistant bacteria or otherwise known as "superbugs" have become one of the world's most pressing public health concerns. Drug-resistant forms of tuberculosis, gonorrhea, and staph infections are just a few of them. Some of the most dangerous superbugs such as *Staphylococcus aureus* (MRSA), *Clostridium difficile, Pseudomonas aeruginosa*, vancomycin-resistant *Enterococcus* spp. (VRE), *Acinetobacter baumannii* etc., are often picked up from the health care setting. Deadly pathogens can survive for long periods of time on hospital surfaces, making the environment a continuous reservoir of infectious agents. The adhesion of pathogens to a surface followed by biofilm formation in less than 24 h is a critical microbiological problem for healthcare services. In fact, the concentration of disinfectants required to kill sessile bacteria may be 1000-fold higher than that required to kill planktonic bacteria of the same strain. There are few prevention techniques to control biofilm formation without causing side effects. The most frequently contaminated surfaces are floors, door-knobs, television remote control devices, bed-frame lockers, mattresses, bedside tables and toilet seats in rooms previously occupied by an infected patient. Therefore, disinfecting hospital rooms and health care facilities is a critical global concern. Disinfection techniques involve the use of chemical agents such as ammonium compounds, aldehydes, alcohols and halogens, or radiation and heat. Prohibiting factors are; effectiveness, toxicity, and cost. Alcohol disinfectants cause protein denaturation and are effective against vegetative bacteria, fungi and viruses, but have no effect on spores. Chlorine-releasing agents can oxidize membrane proteins and are very effective in removing biofilms from surfaces, requiring short exposure times for growth inhibition. However, these chemical agents are corrosive to metals and can be inactivated by the presence of organic matter. The use of chlorine has been associated with the formation of carcinogenic compounds and some pathogens have been shown to be resistant to chlorine. The aldehyde-based disinfectants disrupt proteins and nucleic acids by alkylation and have antimicrobial activity against spores, bacteria, viruses and fungi. Ammonium compounds and phenols solubilize the membrane and the cell wall. Hydrogen peroxide and peracetic acid promote protein denaturation, and are active against several groups of microorganisms and pathogens. Hydrogen peroxide vapor (HPV) is also used for decontamination of clinical surfaces and equipment. HPV appears to have low toxicity and has good compatibility with most inanimate materials. UV light exposure has also been applied for room decontamination. However, UV light is a line of sight process and cannot sterilize hard to reach areas. The reactive oxygen and nitrogen species (ROS and RNS) generated in the mist as disclosed here, can be very harmful to a spectrum of microorganisms depending upon the dose induced in the mist. At high doses, reactive species have been shown to induce apoptosis or necrosis in various cell types. The functional diversity of different reactive species discussed above can be applied to solve various sterilization challenges particularly against the superbugs. Particularly, the transient species (OH*, $NO_2$* and NO* radicals) and the mist form provide unique attributes- compatibility with the infrastructure and the ability to penetrate into hard to reach crevices and surfaces. Notably, the process is chemical supply chain independent and consumes electricity and water only.

Figure 47:
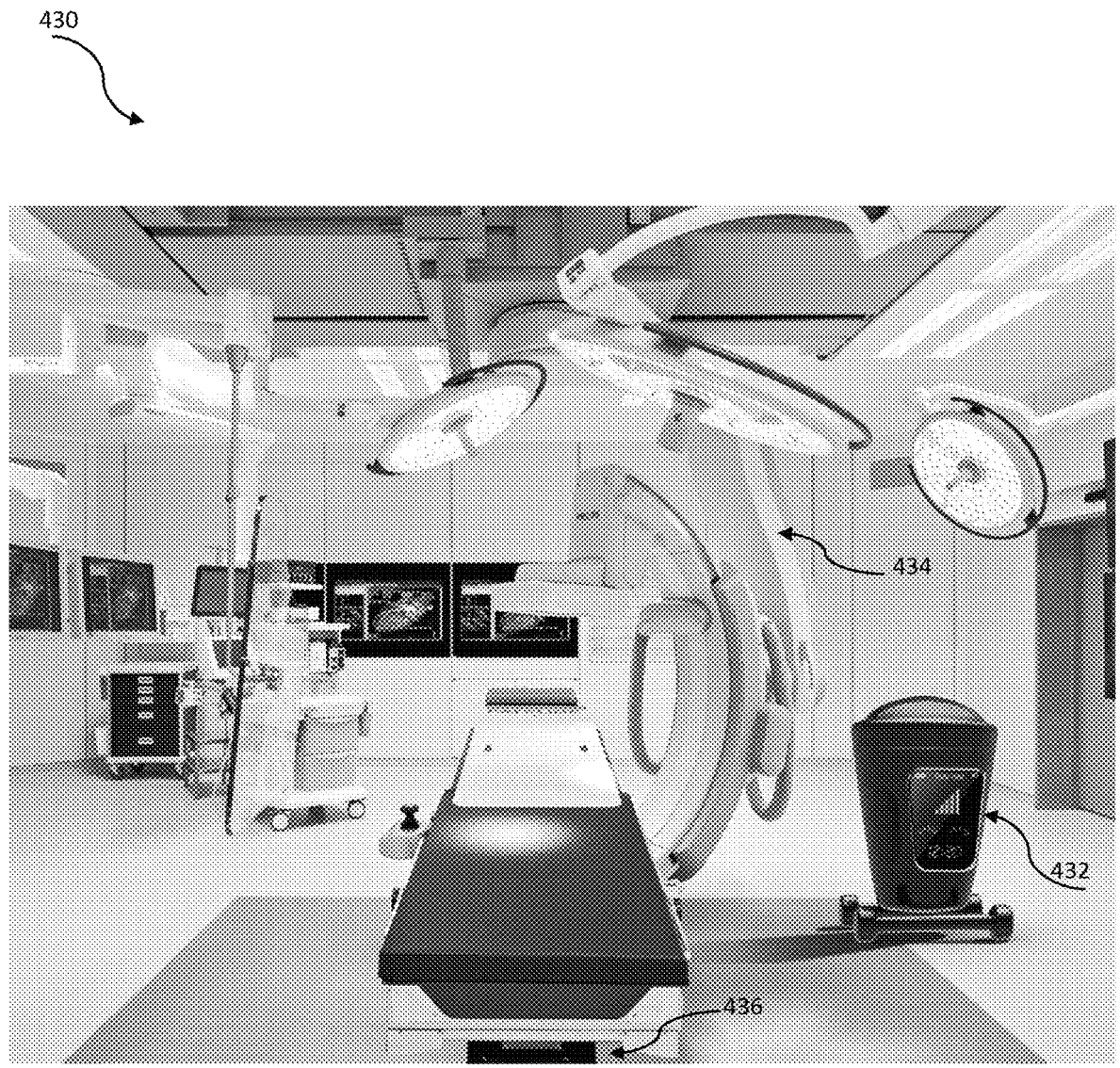
FIG. 47 is an illustration showing the fumigation operation of a healthcare facility with a programmable mobile fumigation device operating according to the teachings of the present disclosure.
Figure 48:
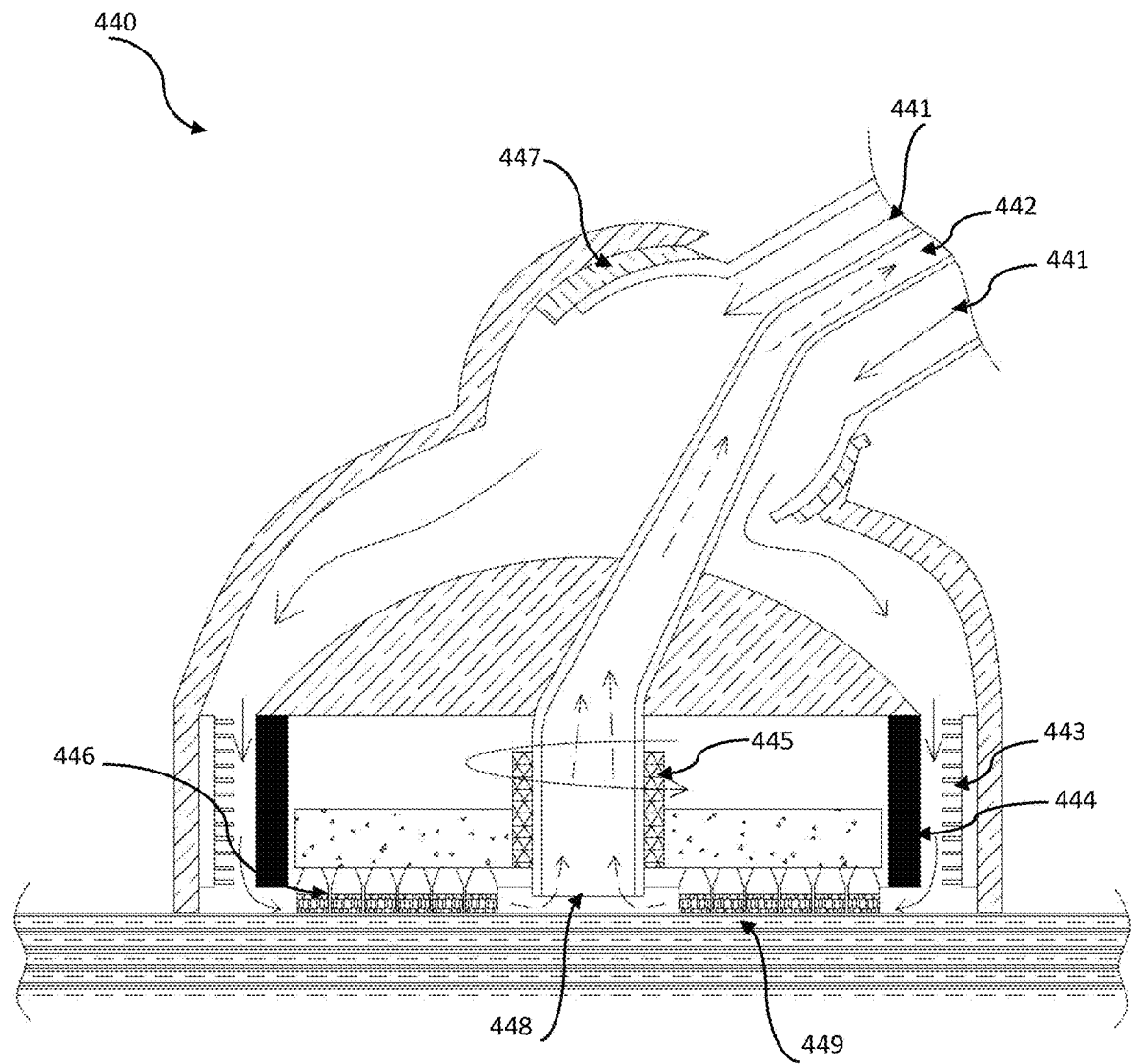
FIG. 48 is a schematic of a surface sanitization system, optionally having a discharge device operating according to the teachings of this disclosure, a provision for vacuum suction and a provision for surface brushing.
Figure 49:
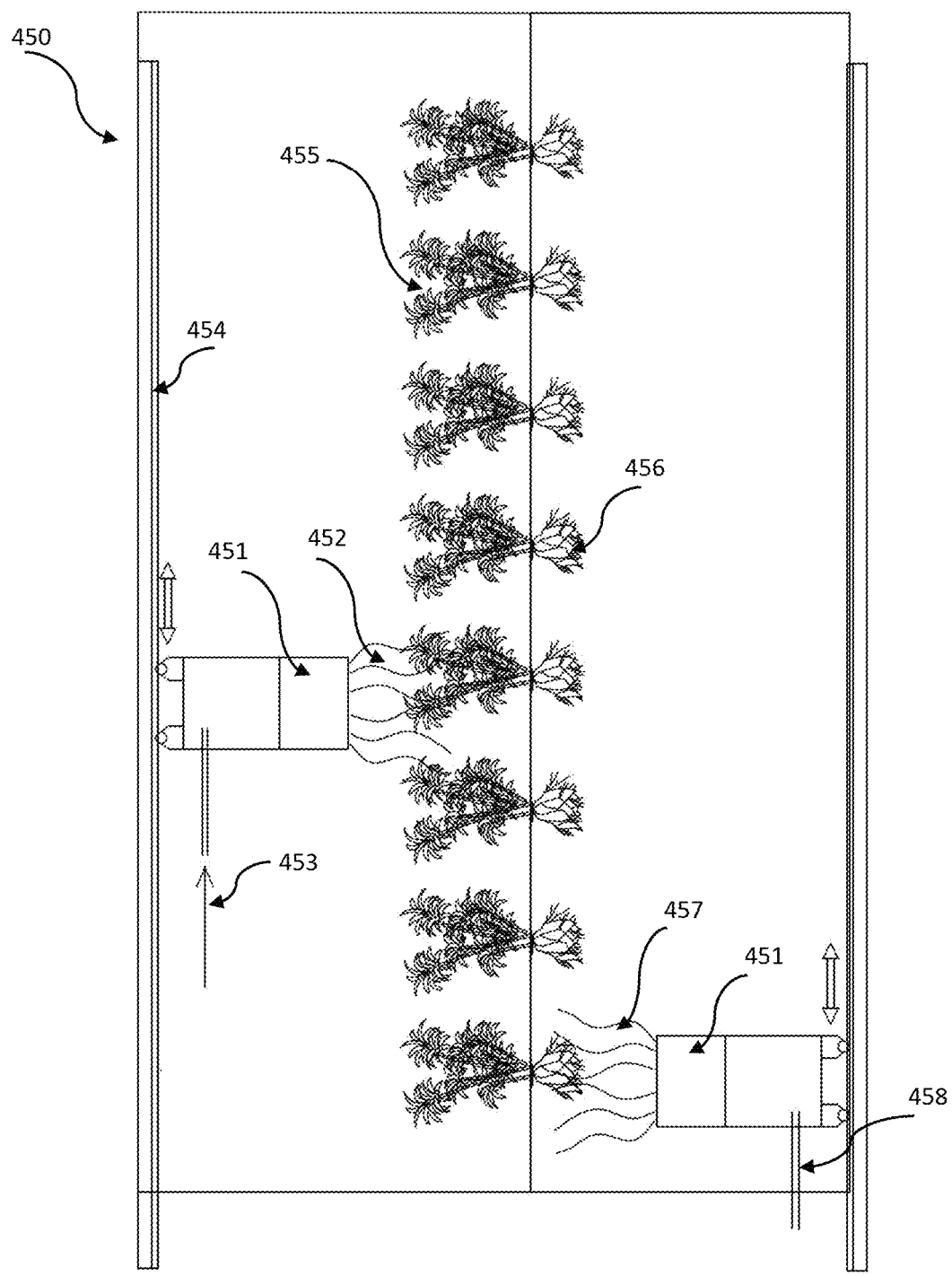
FIG. 49 is a schematic optional arrangement for fumigating hydroponic/green house plants for disease and mold control while providing nutrition by deploying discharge device operating according to the teachings of the present disclosure.
Figure 50:
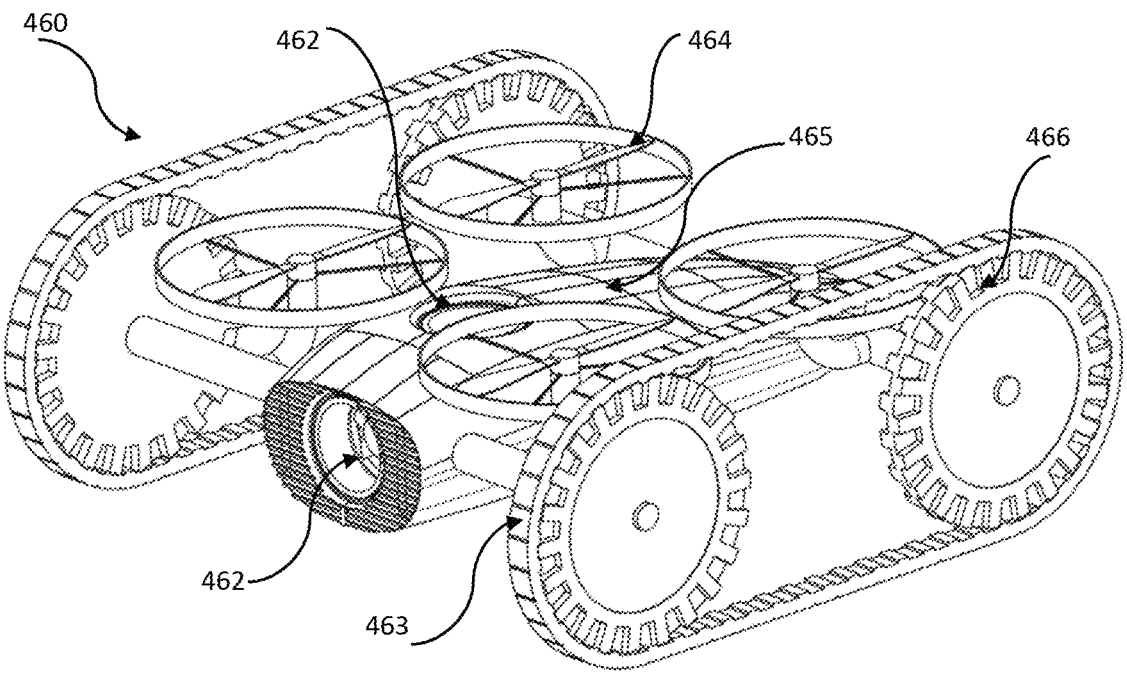
FIG. 50 is a schematic arrangement for a fumigating drone having discharge device(s) operating according to the teachings of the present disclosure.
Figure 51:
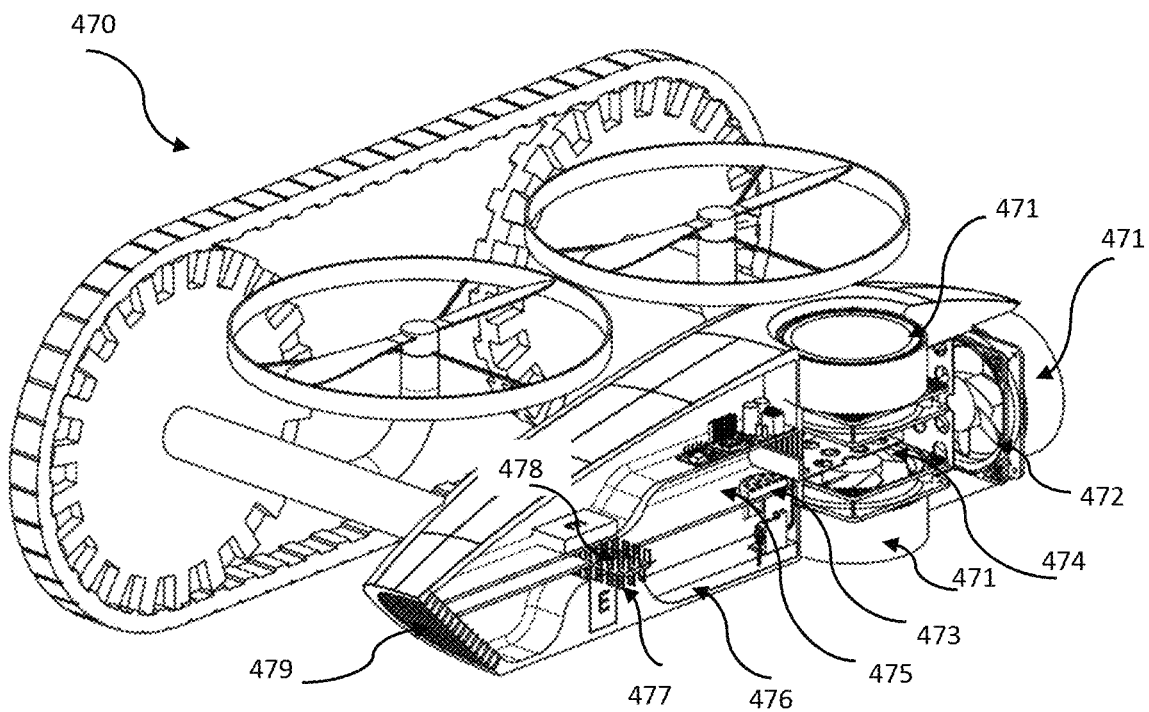
FIG. 51 is a longitudinal cross section view of the main body of the fumigating drone shown in FIG. 50.

The fumigation techniques disclosed above require the removal of patients and health care personnel from the room. Referring to FIG. 48, an optional sanitization device for localized application is disclosed. The sanitization device 440 includes a discharge electrode assembly 443 and a counter electrode 444, being supplied with a mist from a supply source 441. Further, a rotary brush assembly 445 is deposed inside the counter electrode. Optionally, the discharge electrode assembly may be deposed centrally where the discharge pins project outward and correspondingly, the counter electrode surrounds the central discharge electrode assembly. When operational, the mist from the supply source passes through the discharge space where active radicals are generated according to the teachings of the current disclosure. The active radicals are drawn through the brush 446 towards the suction port 448 of the device. During this process the active radicals interact on the target surface and sanitize the surface killing the microorganisms. The spent mist is collected through 442 for further treatment and disposal. Unlike the fumigation device illustrated in FIG. 47, the sanitization device 440 doesn't release any radicals to the atmosphere and hence can be safely used in open space. Optionally, the closed loop sanitization device disclosed here can be configured to treat the ambient air in an occupied space instead of a target surface. Accordingly, the mechanical system may be altered to suit the application.

Figure 52:
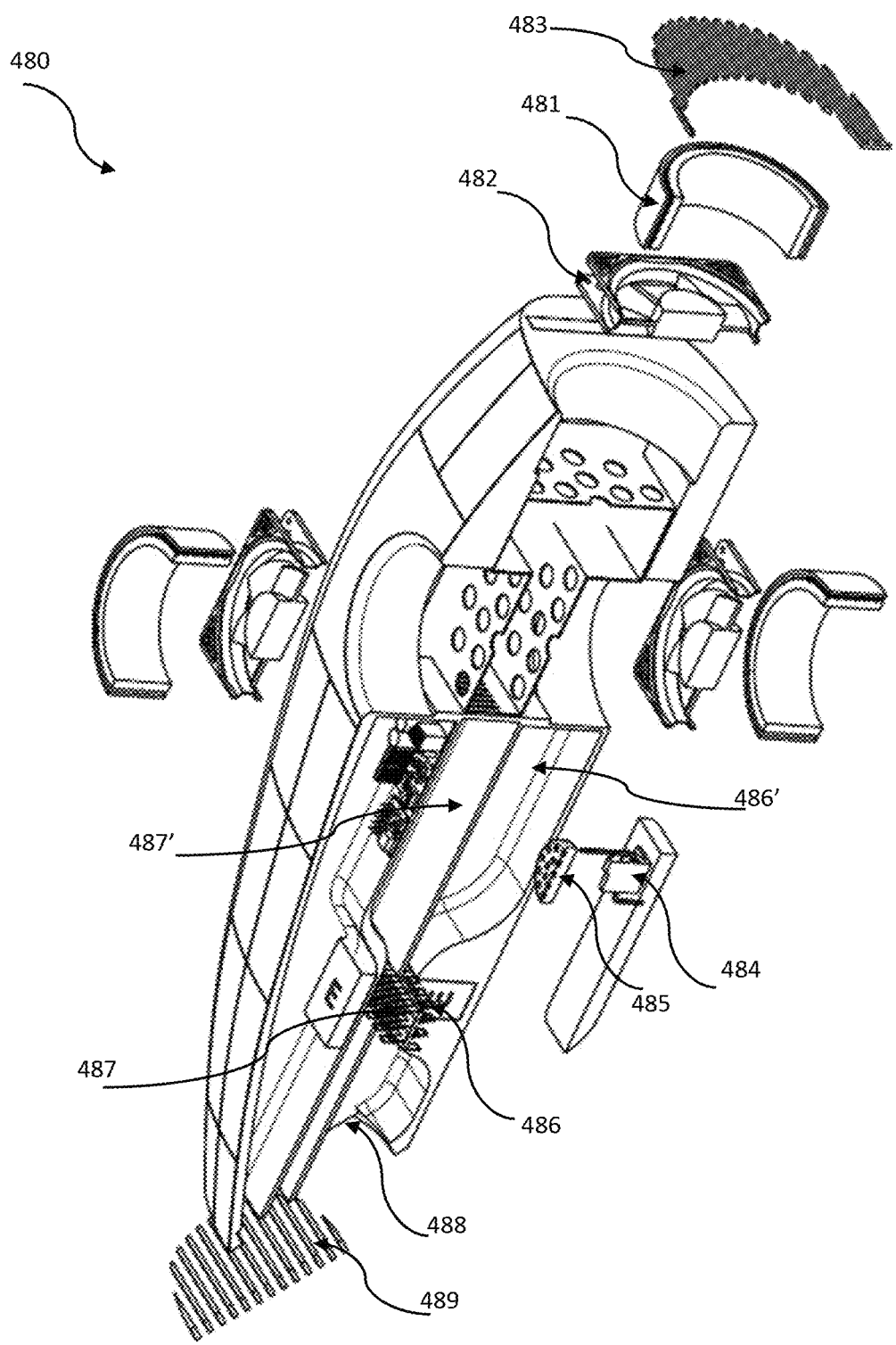
FIG. 52 is an exploded cross sectional view of the main body of the fumigating drone shown in FIG. 50.

As indicated earlier the mist and the carrier gas determines the characteristics of the outgoing mist form the discharge device. For example if the carrier gas is oxygen, the outgoing mist would include $OH^*$, $O^*$, $H_2O_2$ and $O_3$. Optionally, when air is the carrier gas, the outgoing mist may include nitrogen radicals $NO^*$ and $NO_2^*$, and peroxynitrite along with other radicals. Further, when the carrier gas is nitrogen only, the radical types will change accordingly. The energy required for ionizing nitrogen is higher than that of oxygen and water. Therefore, the discharge conditions can be specifically tailored to generate specific radicals and their related compounds when desired. A mist containing such radicals can provide multiple functional (harmful to beneficial) applications for living plants as well as agricultural products. Phagocytic immune cells produce significant amounts of ROS and RNS in response to infectious agents as a means of inactivating pathogens. Conversely, ROS can also induce differentiation, migration and proliferation of cells. In eukaryotic microorganisms such as fungi, ROS regulates hyphae growth and differentiation of conidia and fruiting bodies, and fungal development is associated with changes in ROS levels. In addition, nitric oxide (NO) functions as an important signaling molecule in living cells regulating muscle relaxation, apoptosis, disease resistance, sporulation, secondary metabolism, and sexual development. The functional diversity of different reactive species can be applied to solving various agricultural problems. FIG. 49 illustrates a hydroponic application of the mist containing desired radicals for sanitizing living plants as well as simultaneously providing nutritional supplements to the plants with nitrous radicals. Mold growth is one of the common and recurrent problems for indoor growing as well as outdoors, Beyond certain threshold mold counts, the infested product cannot be consumed. Once infested, the crop can be treated with a variety of biological and chemical products which have theft own residual problems. The radicals present in the mist generated according to the teachings of this disclosure are highly active and can be used as preventive as well as post infestation intervention. The mist penetrates to the intricate parts of the plants and buds where the infestation originates and destroys the fungus including theft spores. Incidentally, the radicals are short lived and are neutralized without leaving harmful residuals. Further, some radicals particularly the RNS ones are also easily absorbed by the plants and provide nutritional supplement. It is to be noted that over exposure can cause damages to the plant and therefore, appropriate doses need to be determined depending upon the conditions. Now referring to FIG. 49, the exemplary hydroponic treatment method comprises of deploying a radical generator 451 optionally fixed to a moving track 454, receiving water supply 453 from a source which is converted into a mist by an appropriate misting device and generating radical carrying mist 452 which is sprayed on the plants 455. Optionally, an additional device can be deployed to treat the roots 456. Functionally, this device receives water 458 from a source, generating the desired mist through the generator 451 and releasing the mist 457 on the roots 456, Optionally, the room can be fogged with the mist to treat the entire space. The droplet size in the mist gas may optionally vary between 0.2 and 100 microns. As such, the droplet size is optionally between 5 and 50 microns. The air velocity in the discharge space may optionally vary between 10 m/s and 200 m/s, optionally between 75 and 150 m/s, optionally between 100 and 125 m/s. At 25° C. and atmospheric pressure, the water content in the feed gas is optionally between 10 g per kg of air and 500 g per kg of air, optionally between 100 g per kg of air and 300 g per kg of air. Optionally, other nutrients can be added to the source water when desired. It is to be noted that the treatment method presented here is exemplary only and many variants and combinations can be engineered for different applications. Many types of molds, pests and fungi can be treated by the methods taught in this disclosure FIG. 50 illustrates an adaptation of the radical generator into a drone enabling the flexibility to treat large target areas for sanitization as well as crop care purposes. The drone 460 includes radical generators 462 that function according to the teachings of this disclosure, propellers 464, a track 463 and wheel 466 to provide ground motion capability. Optionally, the drone is powered by an onboard combustion engine. Optionally, the drone is powered by a battery. Optionally, the drone can include solar panels 465 for onboard power generation. The ground motion as well as flying capability enables the treatment of different areas as desired. The internal view of the mist generation system is illustrated in FIG. 51. Particular attention is drawn to the water source for the mist. Typically, the payload capacity of drones is limited and determines the size and cost of the system. For sanitizing large areas a considerable amount of water will be required and that would increase the payload significantly. Keeping this limitation in view, an onboard water generation system is disclosed. The method includes the source moist air 479 which splits into two streams, one that passes through the hot side 478 and the second that passes through the cold side 477 of a thermoelectric device. The moisture from the cold stream precipitates into water droplets and is stored in a reservoir 476. After releasing the moisture, the cold air is directed to cool the electronics for the radical generators. An ultrasonic mister 473 pumps the water from the reservoir 476 and introduces fine droplets into hotter air stream 475. It is to be noted that the hotter stream now has a higher moisture saturation limit after picking up heat from the thermoelectric device and facilitates the uptake of the droplets introduced by the ultrasonic mister. This mist is then directed to the feed chamber 474, from where the mist is taken up to the desired radical generator by its fan/blower 472. Further details of the fumigation system are illustrated in FIG. 52. The mist generation system comprises of a pump 484 that supplies water from the reservoir to the ultrasonic mister 485. The screen 489 removes debris from the incoming stream before it enters into the device. To remove debris from the front screen 489, the fan of the back discharge device 482 is operated in reverse direction to blow air to the front. The back screen 483 guards against debris intake when the fan operates in reverse mode. The blower fan 482 selectively feeds mist to the desired discharge device and directs the radical laden mist to a desired direction. Depending upon the application, either all discharge devices operate simultaneously or each operates individually. The droplet size in the mist gas may optionally vary between 0.2 and 100 microns. As such, the droplet size is optionally between 5 and 50 microns. The air velocity in the discharge space may optionally vary between 10 m/s and 200 m/s, optionally between 75 and 150 m/s, optionally between 100 and 125 m/s. At 25° C. and atmospheric pressure, the water content in the feed gas is optionally between 10 g per kg of air and 500 g per kg of air, optionally between 100 g per kg of air and 300 g per kg of air.

The radical generating drone as disclosed herein, can be utilized for sanitizing against contagious diseases such as Ebola and plague, super bugs, pest infestation, fungal infestation of crops as well as for fertilization. The discharge power is modulated to generate a selective major fraction of radicals such OH*, O* or N* according to the teachings of this disclosure. For example, a plant-choking fungus called coffee rust has swept across many parts of the world, withering trees and slashing production everywhere. Fungicides have been important tools in the management of coffee rust epidemics, however, they are expensive and have residual chemical effects. Alternatively, the radical laden mist as disclosed here can be deployed to manage the fungal attack and at the same time provide nutrients for healthy foliage. This exemplary application is not limiting and many other fungal/pest management applications can be developed following the teachings of this disclosure. Further, the onboard water generation and misting system can be adapted to other mobile systems where drones are not effective of essential.

Figure 53:
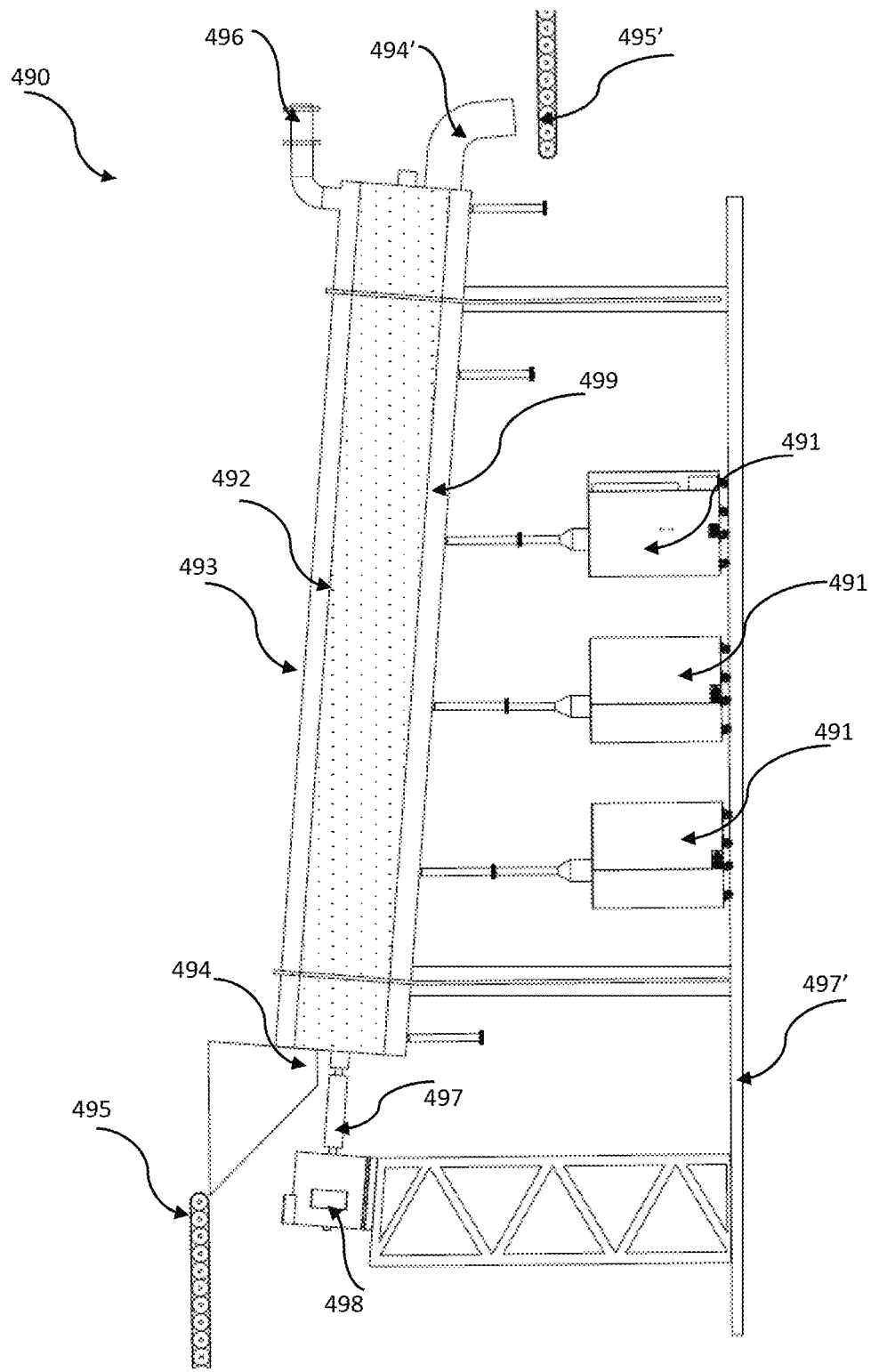
FIG. 53 is a schematic arrangement for fumigating grains and nuts for toxin removal by deploying discharge devices operating according to the teachings of the present disclosure.

As a way of background, mycotoxins are secondary metabolites, or simply chemicals, produced by certain filamentous fungi, commonly found in grains and feed products, Mycotoxins have the potential to cause serious implications for human and animal health. Mold Infection and subsequent synthesis of mycotoxin starts during crop growth and continues during storage. Higher levels of mycotoxin contamination can affect the central nervous system, cardiovascular system, kidney, gastrointestinal system and the immune system. The mycotoxins that are of significant concern to both humans as well as animals are aflatoxins, fumonisin, vomitoxin, zearalenone and T2 toxins etc. Mycotoxin contamination of grain is a complex and frustrating issue. Several methods have been developed to treat mycotoxin contaminated grain and feed products. Application of ammonia (ammonification) to contaminated corn, peanuts, cotton seeds and meals is one potential treatment option that has been used around. The use of chlorine dioxide ($ClO_2$) gas at higher concentrations (500 or 1,000 ppm) with longer exposure time (24 hours) has been found effective to a certain degree. The alternative methods are the use of ozone (U.S. Pat. No. 6,120,822) and gamma irradiation. Most mycotoxin contaminated grain detoxification methods are either leave residue(s) in the commodities that would affect its end use or expensive. A fumigation method to manage mold growth in live plants deploying the radical laden mist generated according to the teachings of this disclosure has already been presented above. Now referring to FIG. 53, a method for detoxification of mycotoxin contaminated grains, beans and nuts etc. is disclosed, comprising a perforated tumbler 492 coaxially deposed in an outer casing 493 leaving a space 499 in between. The coaxial tumbler is rotated along its axis by a motor 498 and a mechanical coupling 497. The rotation speed of the tumbler can be adjusted as desired. The angle between the axis of the tumbler and the base platform 497' is adjustable to enable different slide rates for the feed through the tumbler. The feed to be treated is brought to a hopper 494 by a conveyor belt 495. It is to be noted that various alternative feeding mechanisms can be adopted for this purpose. The radical laden mist is generated according to the teachings of the present disclosure and is fed into the space between the tumbler and the outer casing. The dose and concentration of the mist is adjusted according to the level and type of contamination. This can be achieved by scaling up the discharge device 491 or by deploying multiple discharge devices at different location. The mist injection location, the feed loading, the length of the tumbler and the tumbling rate are adjusted to provide the required interaction time or residence time for detoxification. As the feed traverses down from the feed end to the exit 494', the mist enters into the tumbler through the perforations and mixes well with the feed. Some toxins may be released from the feed and reacts with the mist. At the end of the treatment the feed exits to a conveyor 495'. It is to be noted that the surface of the grains/nuts will be wet as it emerges from the tumbler which requires subsequent drying. The effluent gas is released through 496 and is treated to remove any toxic residue. High water load in the mist may be undesirable for dry grains and nuts. Accordingly, the droplet size in the feed gas may optionally vary between 0.2 and 45 microns. As such, the droplet size is optionally between 5 and 50 microns. The air velocity in the discharge space may optionally vary between 10 m/s and 200 m/s, optionally between 50 and 150 m/s, optionally between 75 and 125 m/s. At 25° C. and atmospheric pressure, the water content in the feed gas is optionally between 10 g per kg of air and 300 g per kg of air, optionally between 75 g per Kg of air and 150 g per kg of air.

Figure 54:
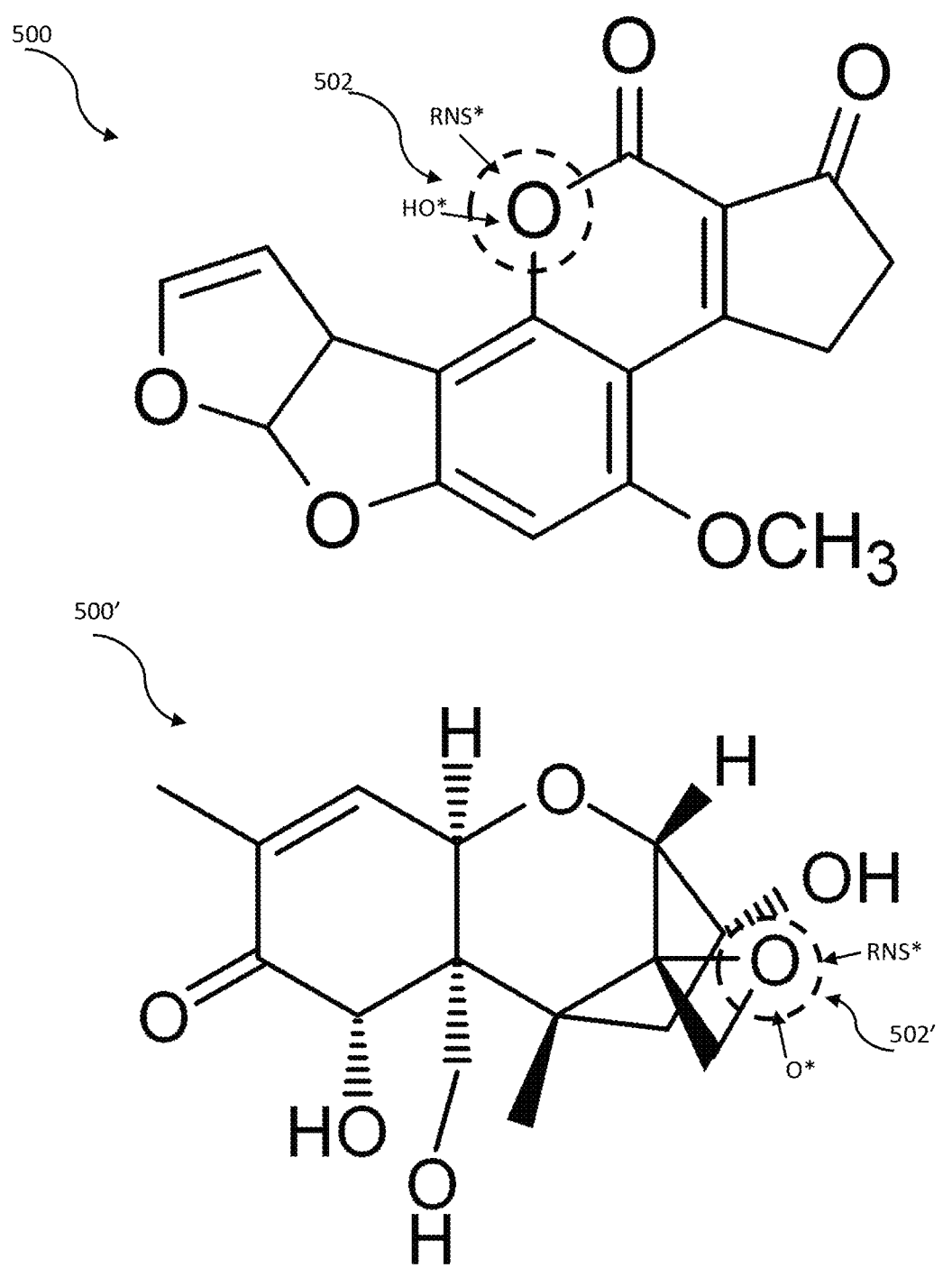

Mycotoxins typically comprise of complex molecular structures and the chemical reaction pathways for detoxification vary from one mycotoxin to another, Now referring to FIG. 54, the molecular model 500 is an aflatoxin typically found in peanuts and sweet corns. One possible detoxification pathway for aflatoxin is to break the bond associated with the oxygen atom 502. Both nitrous and hydroxyl ions can participate in this chemical pathway leading to detoxification. It is to be noted that the complete reaction pathway is not illustrated here, which again depends on the availability of other radicals in the mist. Molecular model 500' is a vomitoxin typically found in wheat grains and the reaction pathway for detoxification is to break the bonds associated with oxygen atom 502', where O* and $H_2N$* radicals can participate. The complex array of radicals present in the mist as taught here creates an effective detoxification environment against a multitude of mycotoxins. Further, the mist containing these radicals effectively attaches to the surface of the grains/nuts compared to gaseous radicals such as ozone or ammonia. Accordingly, the method taught here provides an efficient detoxification technique.

Figure 55:
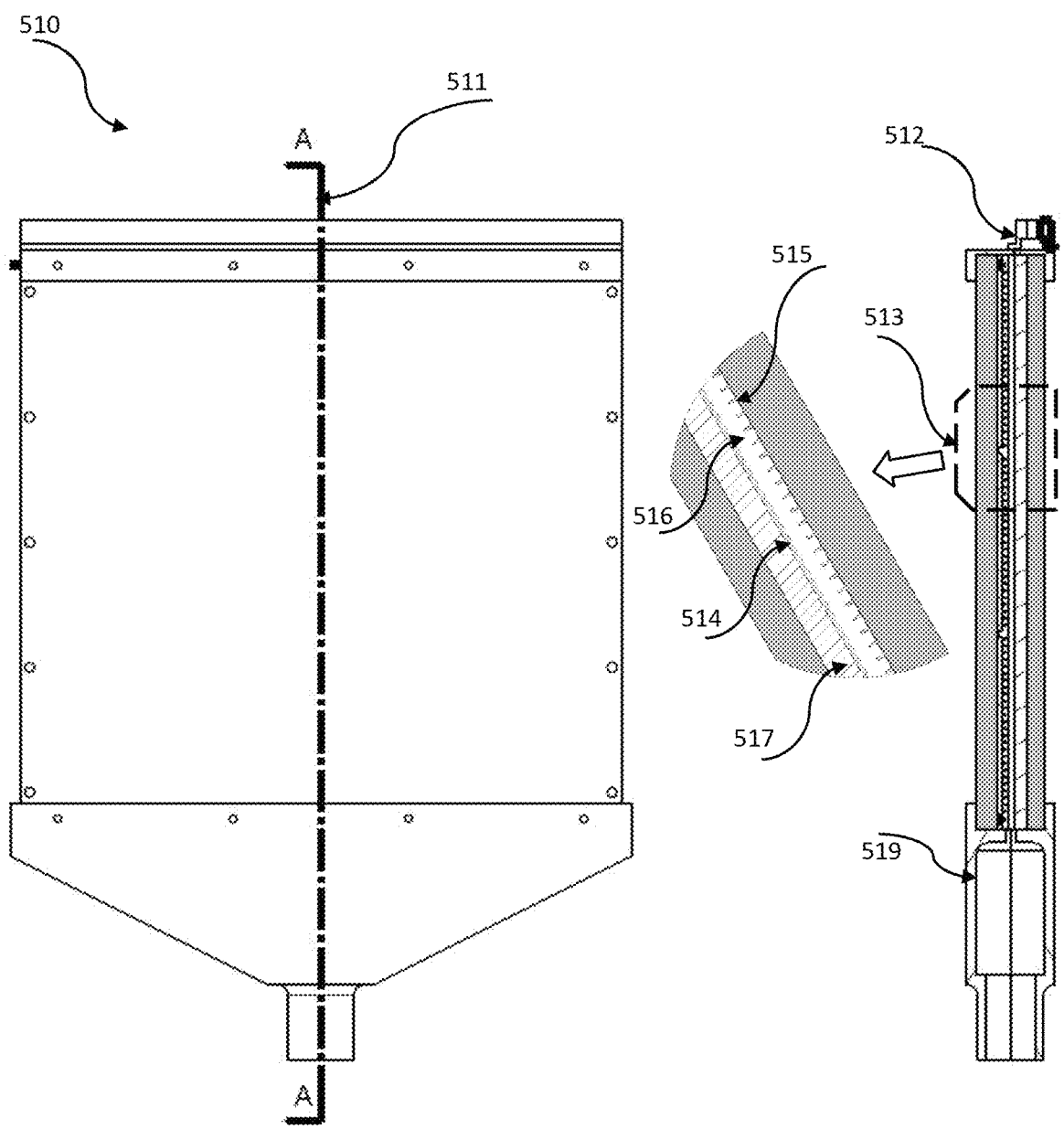
FIG. 55 is a schematic arrangement of a discharge device, having a planar discharge electrode assembly and an optional liquid electrode.

The discharge devices discussed in various forms above utilized a discharge electrode assembled according to the teachings of this disclosure and a counter electrode which is preferably made from a carbonaceous material for resistance against chemical attack. For certain liquid treatment applications it is preferred to deploy the liquid itself as the counter electrode. Now referring to FIG. 55, a planar liquid electrode discharge device 510 is disclosed. The discharge device comprises of a liquid supply member 512, a discharge device assembly 513 and a liquid collection member 519. The enlarged view of the discharge device 513 further illustrates the internal components of the device comprising of a discharge electrode assembly 515, a discharge space 516, a liquid electrode 514 and a back plate 517. The discharge electrode 515 assembly is fabricated according to the teachings of this disclosure that relies on proximity field constrained streamers to cause energetic streamer head for effective ionization and radical generation. The liquid counter electrode 514 is formed by a film of liquid flowing from the supply side to the collection side. The thickness of the film is adjusted such that it maintains a relatively flat surface resulting in a generally uniform discharge space 516. Maintaining a generally uniform discharge gap is critical for maintaining a uniform streamer front on the entire surface. Otherwise the regions with smaller discharge gaps will preferentially generate streamers leaving other regions untreated. Further, too much undulation on the film surface may result in arcing and device malfunction. Therefore, the back plate 517 needs to be carefully selected to maintain a continuous film. It is preferred that that the back plate is made of a conductive material, but most importantly in some aspects it should be hydrophilic. A hydrophilic surface would prevent the breakdown of the films into individual streams. When streamers interact with the film they will induce shock waves and convective flow and with appropriate film thickness a generally stable film can still be maintained. Further, engraving patterns on the back plate can also stabilize the film. There are alternative methods for establishing a uniform liquid layer at the counter electrode. For example, a carbon or graphite felt can be used on the back plate to stabilize the liquid film. Further, a porous bed preferably made out of a catalytic material such as $TiO_2$(and Ag), Zeolite etc. can act as a back plate to provide catalytic reaction in the presence of the plasma. Yet further, the device can be aligned substantially parallel to the ground such that the gravity force acts substantially perpendicular to the flow direction, ensuring flooding of the back plate. The liquid film thickness is optionally between 1 micron and 2.5 cm, optionally between 100 microns and 10 mm, optionally between 0.5 mm and 5 mm. Optionally, fine air or gas bubbles can be introduced into the liquid film. These bubbles can polarize the UV emissions generated from the streamers for further beneficial effect. It is well known that UV emissions can generate radicals in the gas bubbles. Further, UV emissions are also detrimental to microorganisms and disinfect the liquid. However, fine gas bubbles embedded in the liquid film create a polarization effect and make the bubble surface highly active for disinfection and chemical reaction for removing contaminants from the liquid. There are various mechanisms available to introduce microbubbles to the film. Preferably the bubble sizes should be in the order of several hundred microns.

The interaction of the streamer with the liquid electrode causes many physiochemical phenomena depending upon the liquid chemistry, gas in the discharge space as well as the discharge parameters. The type of radicals formed due to streamer interaction with water droplets has already been discussed above. Similar radicals will also form in the liquid water electrode which will sterilize the water against microorganisms as well as facilitate removal/destruction of dissolved substances such as heavy metals and pharmaceutical compounds. Now referring to FIG. 56, a water sterilization and purification system 520 comprising of a liquid electrode radical generator 522, a filtration bed 525 and a flow through capacitive deionization (CDI) system 526 is disclosed. The water electrode radical generator 522 includes a cylindrical discharge electrode assembly 523 assembled according to teachings of this disclosure presented above, a surrounding water stream 524 supported by a back cylindrical wall 529 and a discharge space 528. The thickness of the water stream 524 is controlled by a control valve 521 which can reduce or increase the gate 527 and thereby controls the amount of water released into the liquid electrode stream. The stream maintains a reasonably flat surface (~±0.5 mm) to maintain a reasonably uniform discharge gap (~3-10 mm) and generate a uniform streamer front for maximum treatment efficiency. The liquid film thickness is optionally between 1 micron and 2.5 cm, optionally between 100 microns and 10 mm, optionally between 0.5 mm and 5 mm. To keep the ignition tips free from water droplets and clean, the discharge electrode assemble 350 is preferred, however, it is not a limiting factor. The radical generator can operate with gas flow through the discharge gap. The streamer interaction with the liquid electrode would create many types of radicals in the water stream and subsequent reactions will take place including the destruction of the microorganisms. Any solid particulates that are generated through the reactions will be filtered in the filter bed 535. For example, dissolved lead, arsenic and several heavy metals are converted to insoluble form of their respective compounds by streamer interaction and the precipitated particulates are trapped in the filter bed and thus eliminate them from the stream. Optionally, the filter media can include activated carbon or glass to provide further functionality. The filtered water then passes to the capacitive deionization unit 526. As a way of background, capacitive deionization relies on the application of an electrical voltage to a pair of electrodes that attract dissolved cations or anions to the respective electrode for adsorption, thus removing dissolved salts from the stream. For capacitive deionization to effectively work, the water should possess good conductivity. Particularly, low concentrations of dissolve metals such as lead and arsenic although dangerous for consumption, wouldn't provide sufficient conductive to efficiently operate a capacitive deionization cell. Incidentally, the streamer treated water possesses far superior conductivity due to the creation transient radicals in the water. As a result, the CDI cell can effectively operate in the streamer treated water enabling removal of low concentrations of dissolved ions resulting in ultrapure water.

An exemplary application is haemodialysis. A high quality water is required for haemodialysis and approximately 120 to 300 liters of water is required for a single dialysis session. Contamination of microorganisms (bacteria and endotoxins) or metals and chemicals such as aluminum, copper, calcium, fluoride, chlorine, chloramines and pesticides are harmful to someone on haemodialysis and must be removed from the water prior to use. Typically, the final step of water purification for haemodialysis includes a reverse osmosis (RO) unit. Water is forced through a membrane under pressure, leaving any remaining contaminants behind. The RO membrane removes 99% of contaminants that may be present in the water after all other water treatment has been done (e.g. sediment and carbon filtration). The contaminants are 'rejected' or expelled, along with some water, down the drain. Because of the resistance of the RO membrane, a significant amount of energy is spent in pumping the water through the membrane. Further, the membranes also get plugged with impurities after a period and need to be replaced which is expensive. Alternatively, the water sterilization and purification system 520 provides a low cost complete solution for this application. The liquid electrode radical generator sterilizes the water against microorganisms as well as removes many dissolved impurities in the water and the CDI unit operating on high conductive water from the generator removes dissolved ions even at low concentrations. The CDI process consumes much lower energy compared to RO process. Similar applications for ultrapure water also exists in semiconductor industry, where the current solution is RO process. Incidentally, the streamer treated water can also be used in conjunction with RO unit. The radicals of the streamer treated water can keep the membranes clean and increase their life.

Figure 56:
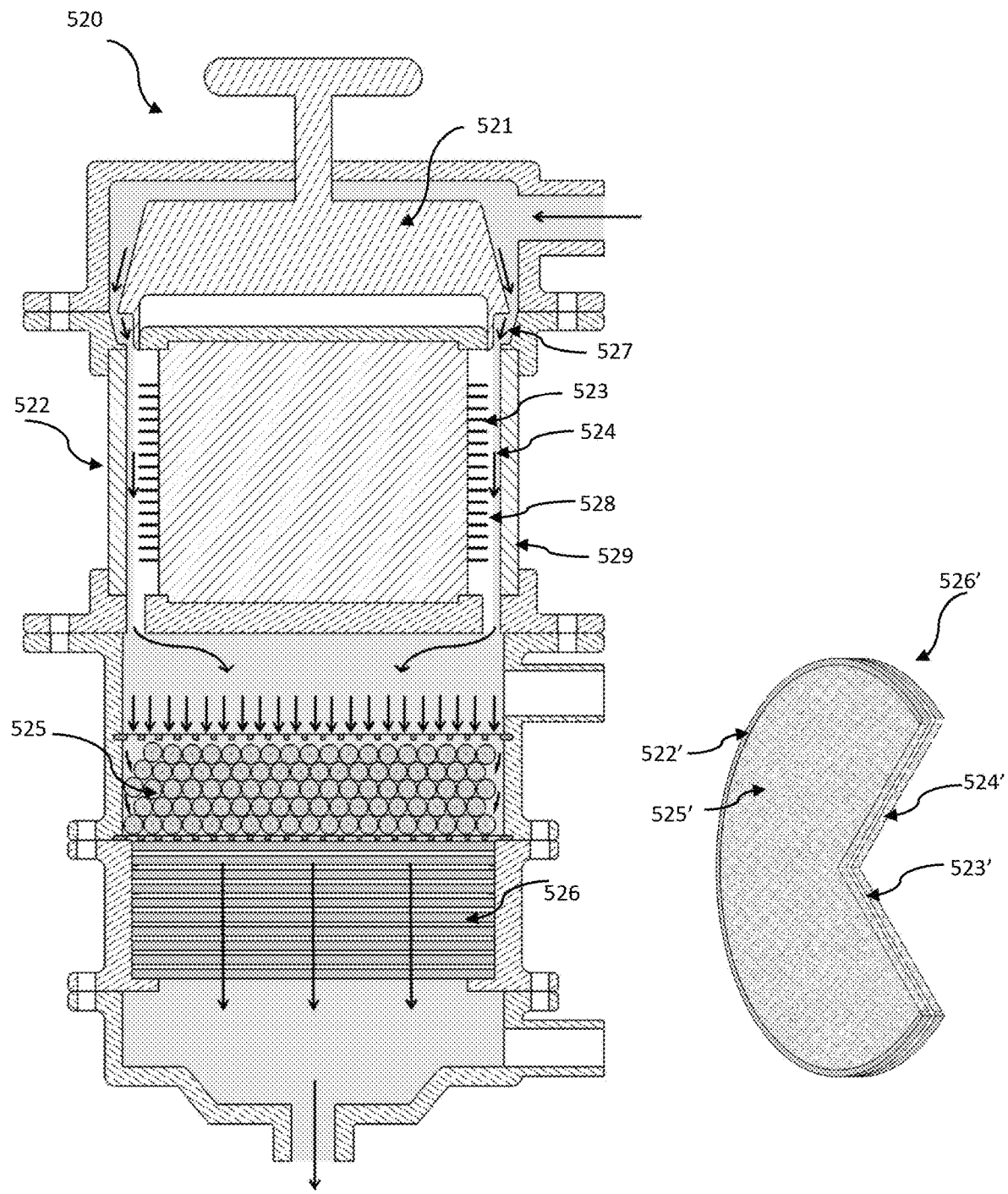
FIG. 56 is a schematic arrangement of a water treatment device employing a cylindrical liquid electrode and an optional flow through capacitive de-ionization system.

Now specific attention is drawn to an exemplary CDI cell as illustrated in FIG. 56. The CDI cell includes a series electrode pairs 526', which includes a flow through electrodes 524' separated by a porous separator 523', which electrically isolates the electrodes. The flow through electrode 524' comprises a porous cloth 525' and an electrically conductive, optionally metal or other conductive material (e.g. carbon such as graphitized carbon), frame 522'. There are several carbon based fibrous materials are used to make these flow through electrodes (cloth) due to their electrical conductivity and chemical resistance. However, to mechanically fasten them to form cell and to electrically connect them to a circuit, an electrically conductive frame 522' is required. Joining metals to carbon fiber based cloth to establish a mechanical frame as well as electrical contact is quite challenging. An additively manufactured porous electrode is disclosed here, comprising a method to infiltrate liquid metal into the fibrous cloth to fabricate the frame 522'. This is preferably done by melting metallic powder by a laser beam and infiltrating the said material along a predefined path. Upon consolidation the desired mechanical and electrical contact layer 522' is formed.

Figure 57:
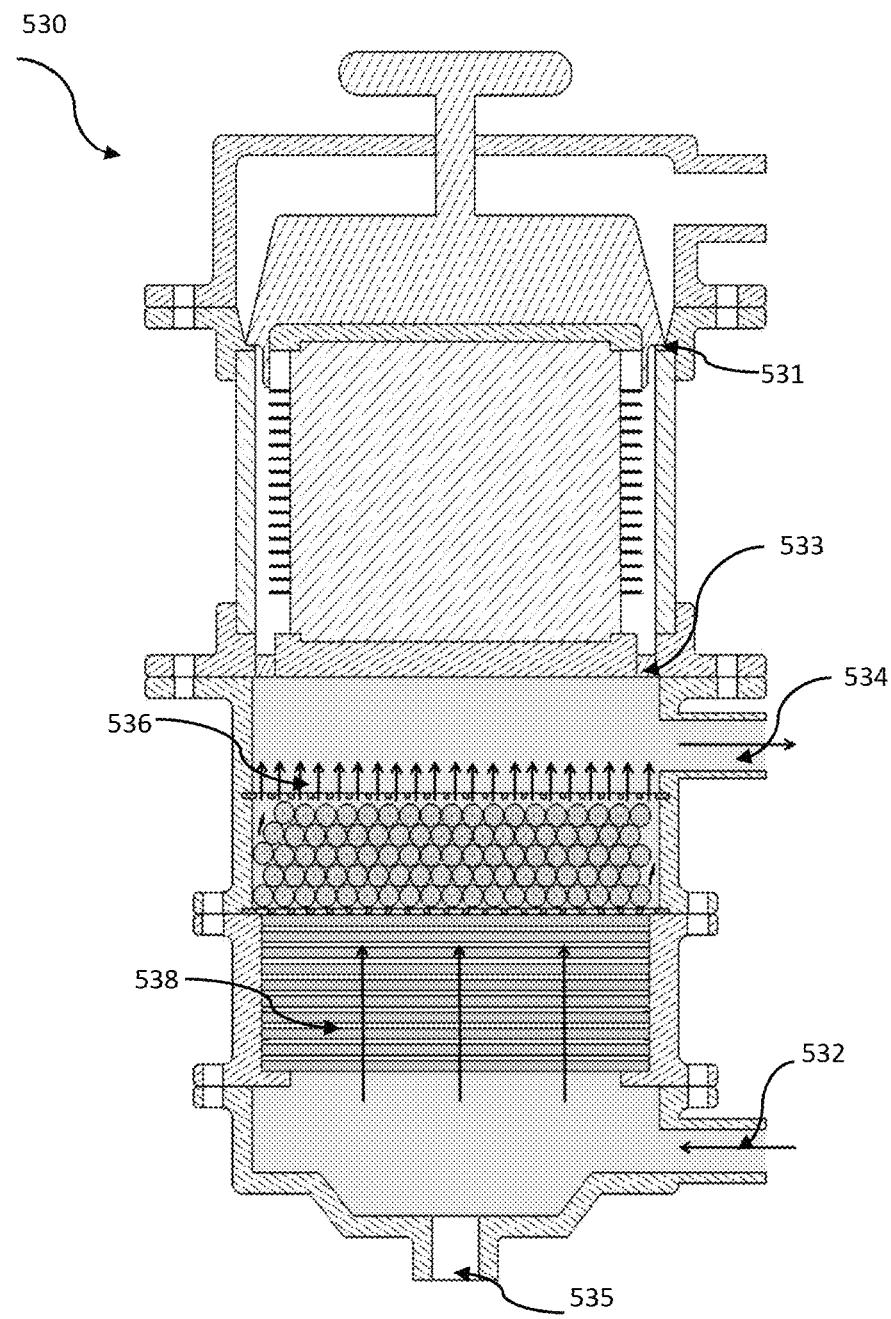
FIG. 57 is a schematic illustration showing the desorb cycle of the capacitive deionization process and filter backwashing for the device shown in FIG. 56.

The CDI cell operates in cycles namely, absorption and desorption cycles. In the absorption cycle, as the water passes through the porous cloth, the positive ions such as $Pb^{30}$, $Na^+$, $As^{+3}$ get absorbed by the negative electrode and the corresponding negative ions such as $Cl^-$, $SO_4^-NO_3^-$ are absorbed in positive electrode, resulting in clean water. As these electrodes get saturated with ions, the polarity is reversed whereby the absorbed ions are released to the water resulting in waste water and clean the electrodes for the next cycle. The absorption cycle is longer than desorption cycle. Now referring to FIG. 57, in desorption cycle, the water valves 531 and 533 prevent water flow to the radical generator. Valve 535 is also closed. The water is then supplied in a reverse direction through valve 532 which flows backwards through the CDI assembly 538 carrying the desorbed ions as well as the filter bed 536, backwashing the filter bed. The waste water is discarded through valve 534. Thus an effective water treatment system is provided.

Figure 58:
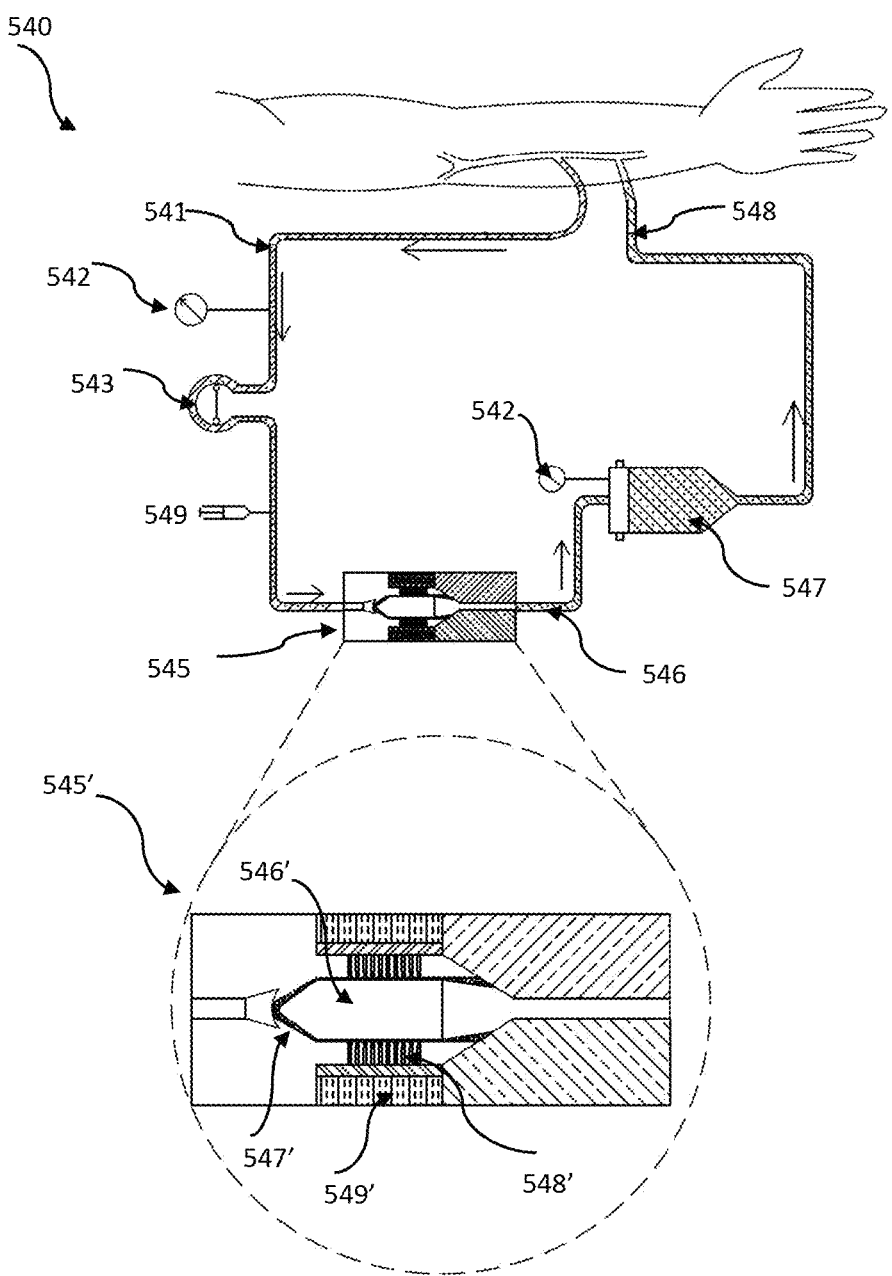
FIG. 58 is a schematic arrangement for blood treatment deploying a liquid electrode discharge device operating according to the teachings of the present disclosure.

The discharge device with liquid electrode can be utilized for a variety of application besides water treatment as described above. Referring to FIG. 58, a system 540 to treat blood against diseases is disclosed. Here the blood stream itself acts as a liquid electrode. The motivation to treat blood directly with streamers emerges from the fact that many active radicals are created with this interaction which can beneficially be utilized for therapeutic purpose such as inducing cell growth arrest and apoptosis or anti-proliferative properties. Non-thermal plasma treatment against various cancer cell lines have yielded promising results, for example colorectal cancer and leukemia cells. These studies were performed by utilizing an atmospheric plasma jet emitting form a dielectric barrier discharge device on cultured biological samples. The therapeutic treatment system 540 disclosed herein comprises of a supply line 541 drawing blood via a pump 543 and delivering it to the streamer generation device 545. The supply line further includes a pressure gauge 542 and a blood pump 543 to regulate flow as desired as well as inlet 549. The inlet 549 can be utilized to introduce a desired fluid such as an anticoagulant or drug. The enlarged view of the discharge device 545' shows further details comprising a central body 546' upon which the inlet blood stream forms a uniform film 547' which functions as the ground electrode. A discharge electrode assembly 548' fabricated according to the principles of the current teachings surrounds the central counter electrode 546' coaxially. The gas environment in the discharge device can be controlled by a gas manifold 549' which in communication with a source. The streamer treated blood 546 from the discharge device is collected in a reservoir 547 where its pressure and residence time is monitored. It is desirable that gaseous bubble if any should be avoided going into the return line. Optionally, the return line includes a pump to regulate the return flow. Although many return and supply configurations can be deployed, it is preferred that the supply and return line are connected to a vein for practical purpose. The arteries are located deeper from the skin and it will require a surgical procedure to connect to the device. Further considerations also should be given to the blood flow requirement. Although the device can be connected to a vein when the blood flow rate is low, however for larger flow rates a catheter should be utilized as in the case of haemodialysis. The blood flow rates into the discharge device is optionally 200 ml/min, optionally 300 ml/min, optionally 400 ml/min, optionally 500 ml/min, optionally 600 ml/min, optionally 700 ml/min, optionally 800 ml/min. The liquid film thickness is optionally between 0.5 mm and 5 mm.

Figure 59:
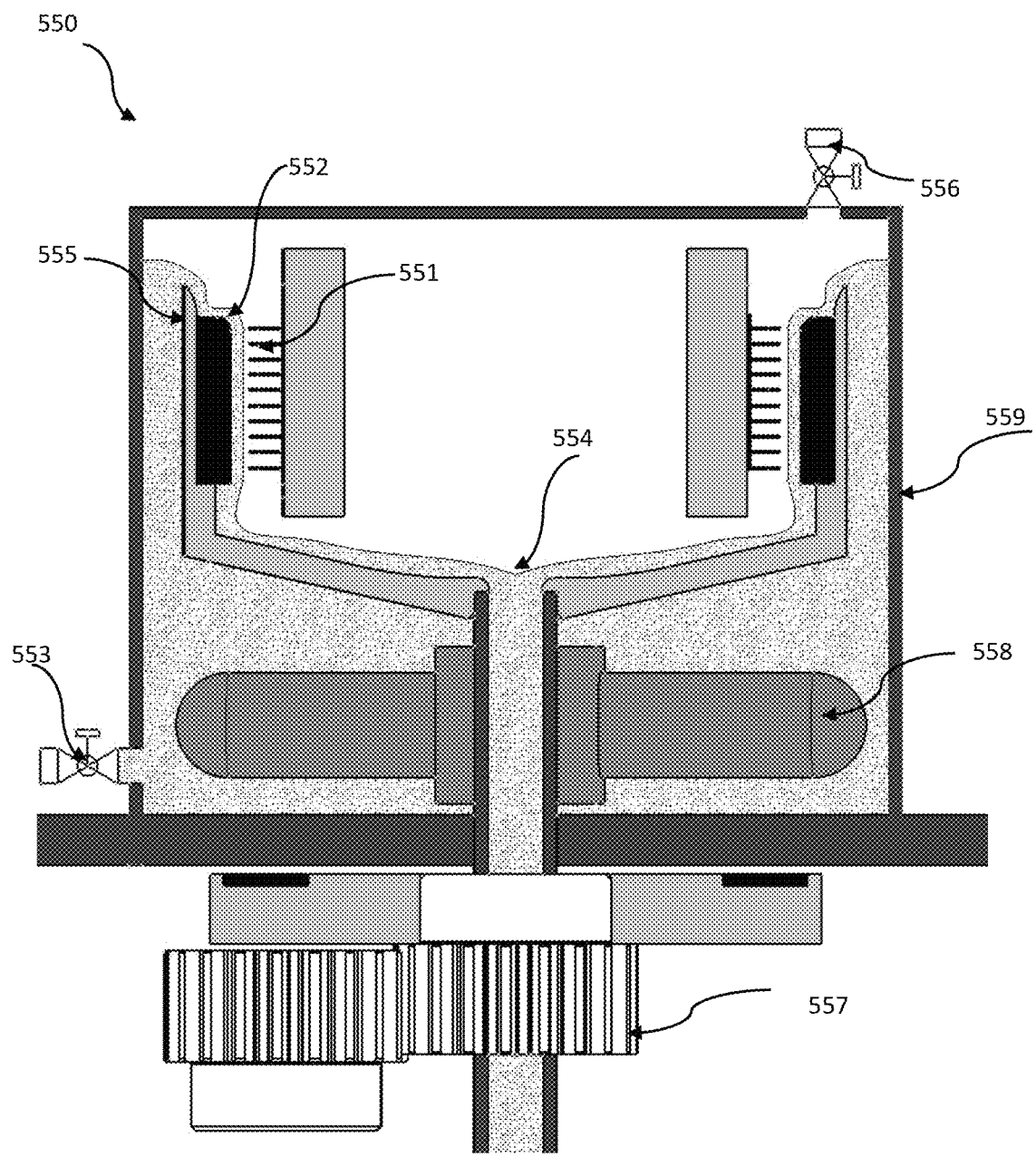
FIG. 59 is a Schematic arrangement of a liquid treatment device employing liquid electrode discharge device and a magnetic impeller.

As mentioned above, plasma jets from dielectric barrier devices have been utilized in experimental studies involving cancer cell lines. To generate a plasma one must utilize a gas flow and the composition of gas into the discharge device determines the reactive species that interacts with the samples. For example, with air it is expected to have O, $O_2$, $O^-_2$, $O_3$, OH, NO and $NO_2$ etc. By deploying the blood stream as the liquid electrode, one can completely avoid the use of an external gas supply and yet generate free radicals utilizing the $O_2$ and $H_2O$ of the blood stream. When desired, an external gas can be supplied to the discharge space to generate other free radicals. Managing the oxidative stress is critical for the success of the therapy and therefore enabling control and flexibility provides better therapeutic outcome. Accordingly, FIG. 59 provides for a liquid electrode discharge device comprising of a magnetic stirring mechanism to control the flow and thickness of the liquid electrode. The device 550 includes a magnetic stirrer 558 deposed in an outer fluid chamber 559 which is in communication with the liquid supply 553 as well as a gas supply line 556. The magnetic stirrer 558 is coupled to a pair of magnets and a drive mechanism 557. The inner chamber forms the discharge device comprising of a discharge electrode assembly 551 assembled according to the teachings of the current disclosure, a counter electrode 552 and a fluid outlet 554. When engaged, the rotation of the magnetic stirrer pushes the liquid into the inner chamber forming the liquid electrode 552. The streamers from the discharge electrode assembly cause physiochemical reaction in the liquid electrode which exits the chamber through outlet 554. An external gas can be supplied to the chamber through 556 to maintain a desired environment in the device. The flow rate and in turn the thickness of the liquid electrode can be controlled by the inlet flow and the magnetic stirrer speed. It should be noted that the stability of the liquid electrode plays a crucial role on the operational stability of the device. The blood flow rates into the discharge device is optionally 200 ml/min, optionally 300 ml/min, optionally 400 ml/min, optionally 500 ml/min, optionally 600 ml/min, optionally 700 ml/min, optionally 800 ml/min. The liquid film thickness is optionally between 0.5 mm and 5 mm.

Figure 60:
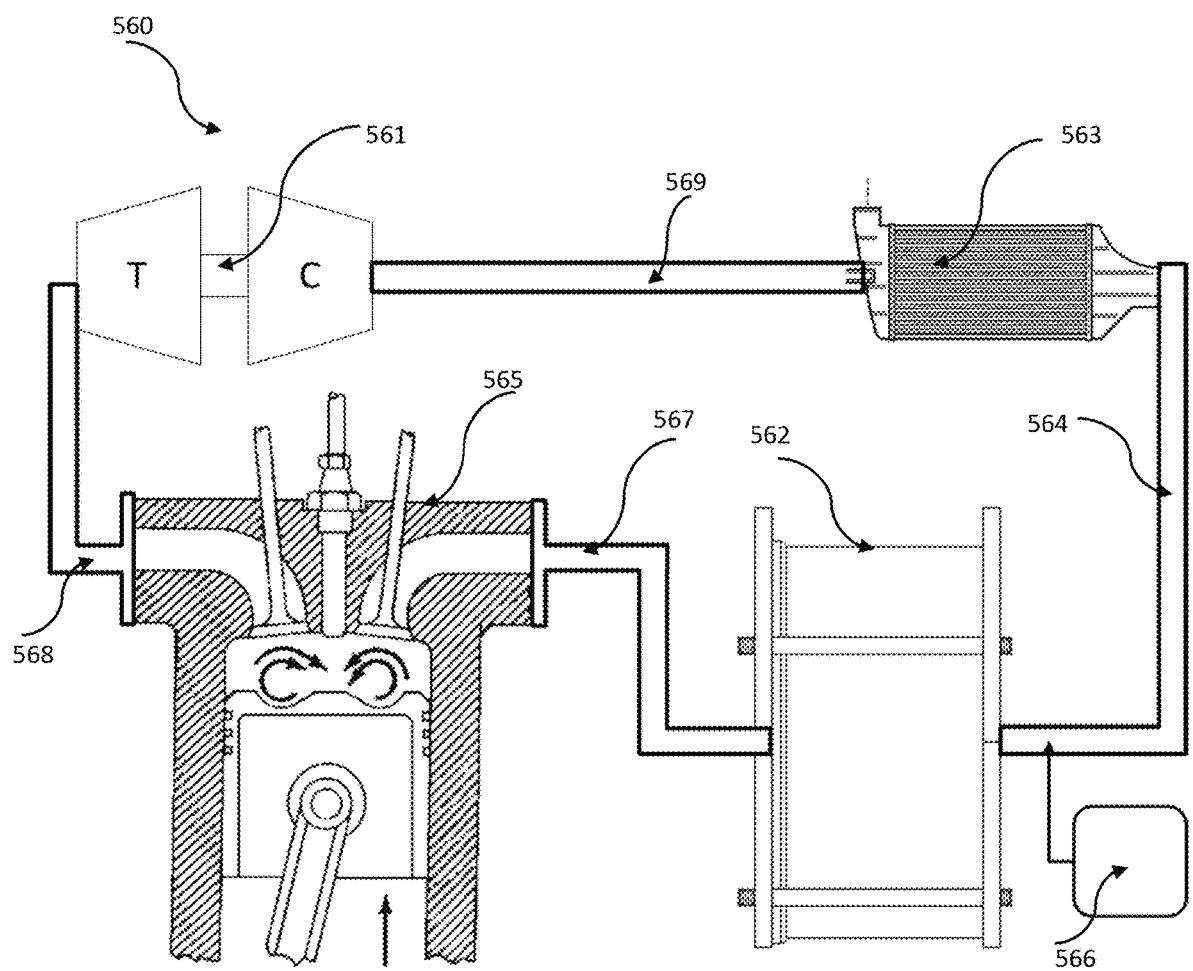
FIG. 60 is a schematic arrangement for combustion engine intake air ionization employing an optional discharge device of the present disclosure.

Now referring to FIG. 60, a system arrangement 560 to provide free radicals to an internal combustion engine is provided. The free radicals improve combustion efficiency and reduce emissions. The system includes the IC engine 565 from which the exhaust gas 568 is utilized in the turbocharger 561 which supplies compressed air 569 to a cooler 563. The cold compressed air is fed into the discharge device 562 of the current disclosure which generates free radicals. The control system 566 monitors the temperature and flow conditions of the feed air and directs an appropriate amount of air through the discharge device for optimum performance. The free radical laden intake air 567 is taken into the IC engine for combustion. Optionally, a discharge device 562 can also be deployed at the exhaust 568 for emission reduction.

EXPERIMENTAL

1: Discharge Phenomena and Streamer Interactions

Figure 61:
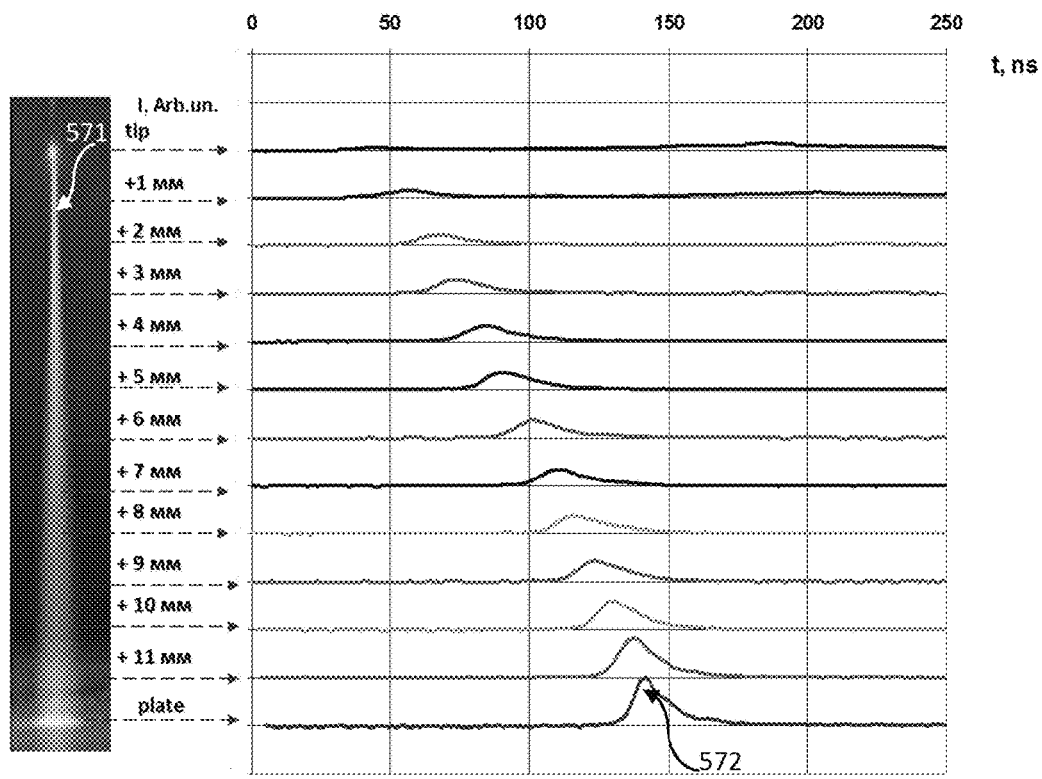
FIG. 61 presents the light emission intensity from a positive streamer along the discharge gap (V=9.5 kV, $I_{total}$=50 µA, discharge gap G=12 mm)
Figure 62:
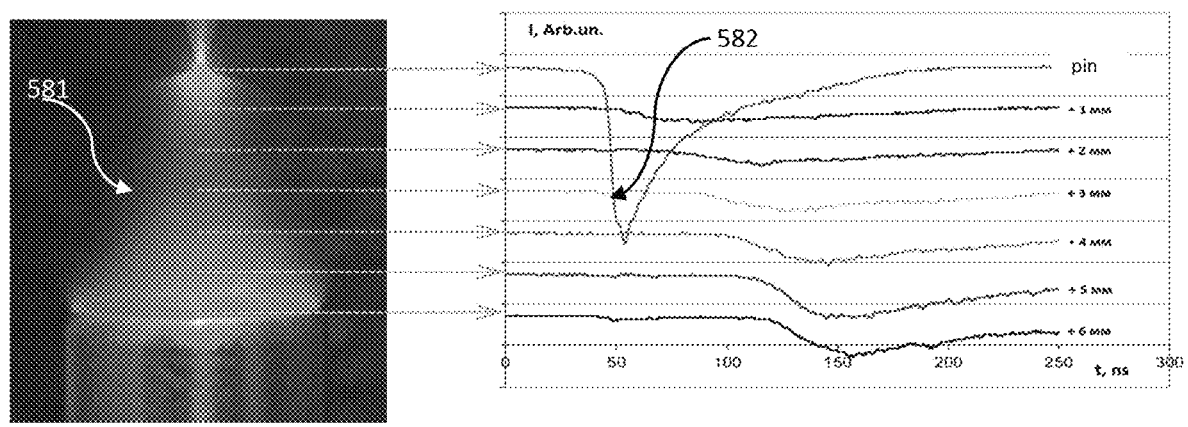
FIG. 62 presents the light emission intensity from a negative streamer along the discharge gap (V=10.5 kV, $I_{total}$=100 µA, discharge gap G=7 mm)
Figure 63:
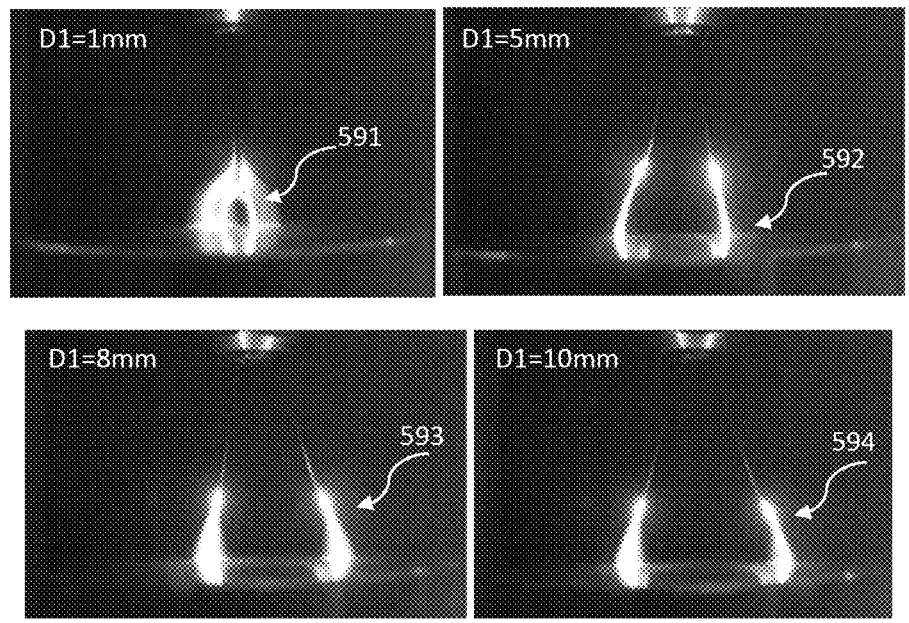
FIG. 63 presents the repulsive interaction between positive streamers (V=5.0 kV, $I_{total}$=50 μA, discharge gap G=5 mm)
Figure 64:
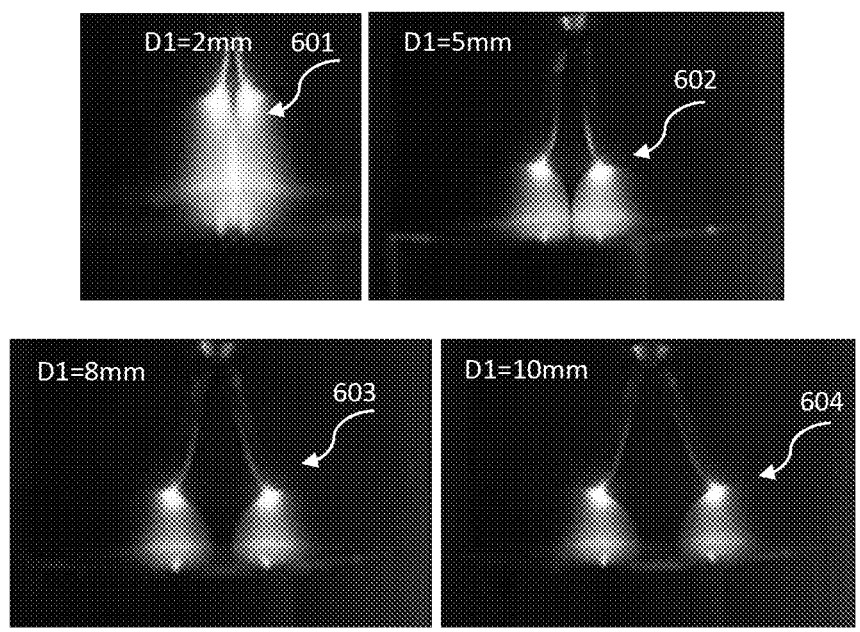
FIG. 64 presents the repulsive interaction between two negative streamers (V=7.5 kV, $I_{total}$=100 μA, discharge gap G=5 mm)
Figure 65:
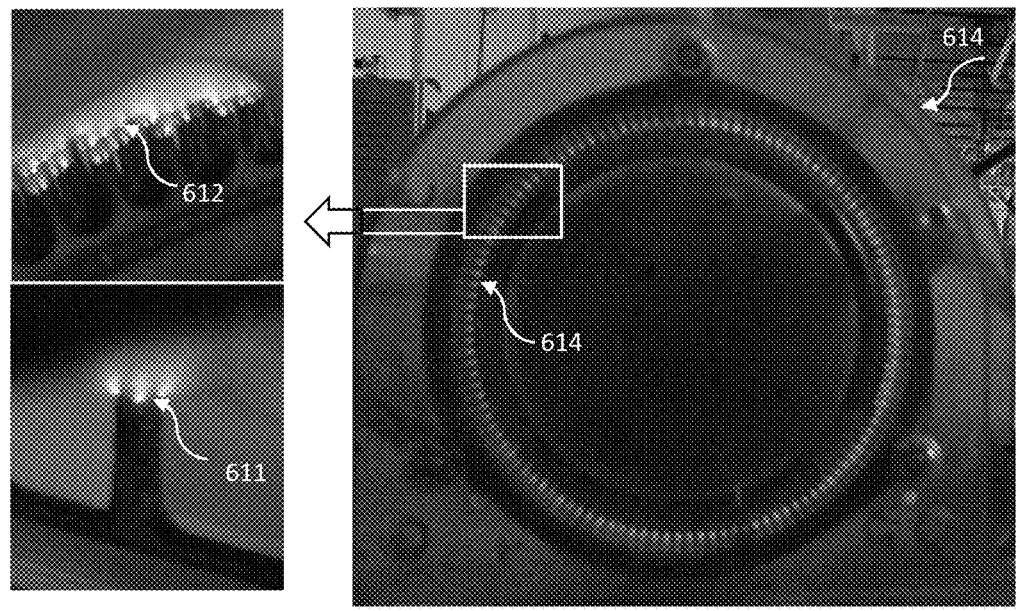
FIG. 65 presents an experimental discharge device assembled according to the teachings of the present disclosure.

As described above, the streamer behavior depends on the polarity of the electrode, the geometry of the discharge pins as well as their proximity to other discharge pins or ignition tips. FIG. 61 demonstrates the characteristics of a single positive streamer 571. As can be seen the streamer is narrow and the field enhancement 572 at the tip continues to increase as the streamer propagates through the discharge gap. The field enhancement here is measured indirectly via emission intensity as streamer traverses through the discharge gap by photo diodes positioned at slits cut in at different distances from the ignition tip. This characteristics of the positive streamers enable operation of a discharge device with larger gap. As a comparison, FIG. 62 presents the characteristics of a single negative streamer 581. As can be seen the negative streamer broadens its diameter rapidly and accordingly the field enhancement at the tip 582 also quickly weakens as it traverses through the discharge gap. Such tip broadening is not preferred as its radical generation capability or in other words the probability of high energetic electrons diminishes, which often leads to zero net ionization. Therefore, mechanisms to constrain the radius enlargement are necessary for effective radical generation. FIG. 63 demonstrates the repulsion between two nearby positive streamers at various inter tip distances D1; 591 at 1 mm inter tip distance, 592 at 5 mm inter tip distance, 593 at 8 mm inter tip distance, and 594 at 10 mm inter tip distance. Due to strong identical electric fields developed at the streamer head they repel each other as they traverse through the discharge space. Note that there are no restrictive forces outside the inter pin gap, thus enabling them to travel along a curved path until they reach the counter electrode. FIG. 64 demonstrates the repulsion between two negative streamers at various inter tip distances, D1. Due to the weak field enhancement at the negative streamer head the repulsive force is expected to be weaker, nevertheless the streamers of same polarity, either positive or negative would always repel each other in contrast to the teachings of some prior art discussed earlier. Accordingly, the current disclosure teaches to deploy the repulsive force between streamers to provide field constraints from all sides to each streamer and in turn limit the streamer head broadening to generate an ionization front with high field intensity. FIG. 65 presents a device that was fabricated with discharge pins having four ignition tips 611, according to the teachings of this disclosure. The generation of four streamers from an isolated discharge pin including a square top hat profile is demonstrated here. As seen here, these streamers repel each other away from the pin normal as there is no surrounding constraints present. The device 614 utilized 3840 (960 discharge pins, square size=0.25×0.25 mm$^2$) ignition tips, with inter pin distance=2.5 mm and ignition tip to counter electrode distance=4.5 mm, arranged on a discharge electrode assembly having diameter of 122 mm and 25 mm height. The discharge electrode was connected to negative polarity with the following voltage parameters: $V_{applied}$=−9.5 kV, Pulse width=1 µs, f=15 kHz, with an average power of 150 Wh. The discharge electrode was made from stainless steel and the ground electrode was made from graphite. Air was drawn into the discharge space with a fan at 50 m$^3$/hour. As observed here, when the discharge electrodes are assembled according to the teachings of this disclosure, the streamers 614 experience field constraints from the surrounding streamers which push them towards the pin normal. Importantly, this restriction limits the streamer broadening which is essential to maintain field enhancement at the head and prevent the generation of secondary streamers. The propagation of the corresponding ionization front is shown in the enlarged view 612.

2. Effect of Bias Voltage and Gas Flow

Figure 66:
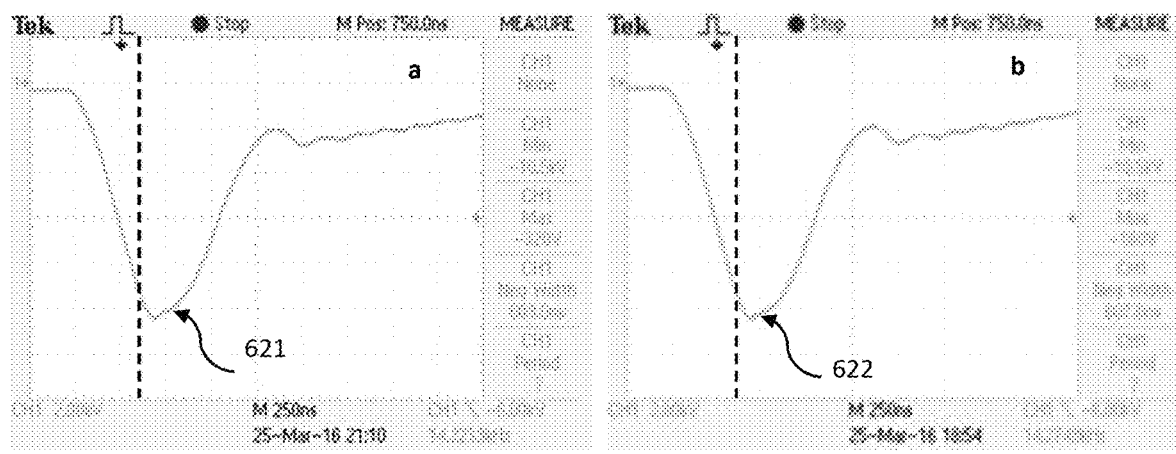
FIG. 66 presents exemplary voltage pulses at 85 W Power, Q=5 m3/h air flow; (a) 0 V bias, (b) 200V bias.
Figure 67:
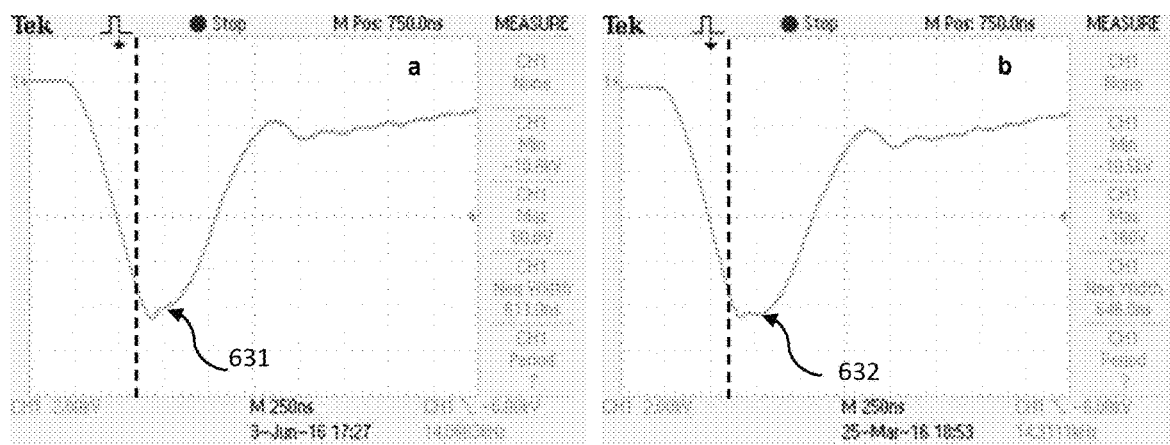
FIG. 67 presents exemplary voltage pulses at 100 W Power, Q=5 m3/h air flow; (a) 0 V bias, (b) 200V bias.
Figure 68:
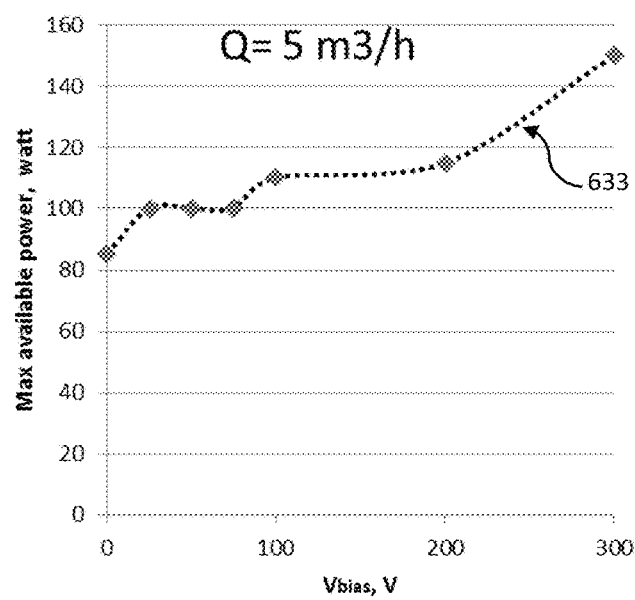
FIG. 68 presents the availability of maximum power for discharge at different bias voltage for a given flow Q=5 $m^3/h$.
Figure 69:
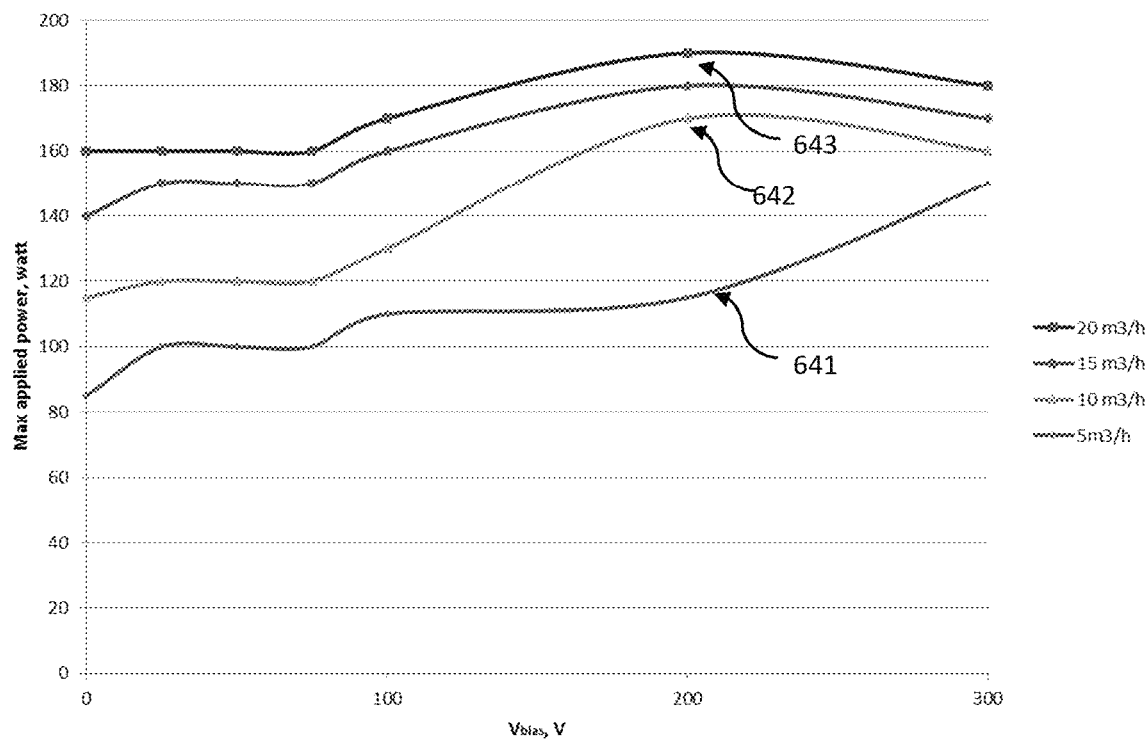
FIG. 69 presents the availability of maximum power with respect to applied bias voltage at different flow rates.
Figure 70:
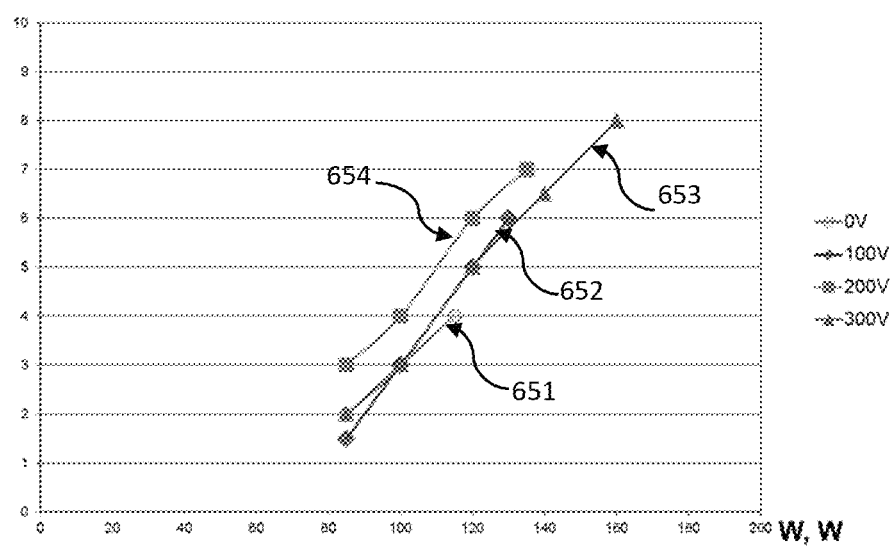
FIG. 70 demonstrates ozone productivity variation with respect to applied bias voltage at 10 $m^3/h$ flow rate.
Figure 71:
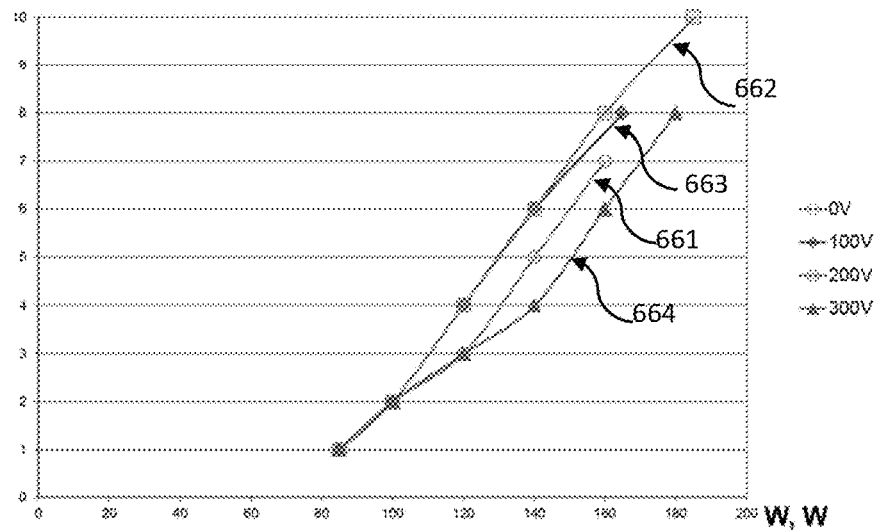
FIG. 71 demonstrates ozone productivity variation with respect to bias voltage at 20 $m^3/h$ flow rate.

As indicated above ozone forms via $O(^3P)+O_2+M \rightarrow O_3+M (M=N_2, O_2, O_3)$ and that the high energy atomic oxygen $O(^1D)$ loses its excessive energy due to relaxation collision with gas molecules via $O(^1D)+M \rightarrow O(^3P)+M$. If dry gas is fed to the discharge space, then OH* generation as described above will be suppressed leading to primarily $O_3$ formation. To study the effect of the bias voltage and the gas flow on the discharge behavior, ozone production was monitored as an indicator. A device was assembled according to the teachings disclosed here. The device parameters were kept as follows: 15500 (3875 discharge pins, square size=0.25×0.25 mm2) ignition tips, with inter pin distance=2.5 mm and ignition tip to counter electrode distance=4.25 mm, arranged on a discharge electrode assembly having diameter of 30 mm and 430 mm height. The discharge electrode was connected to negative polarity with the following voltage parameters: $V_{applied}$=−9.5-10.5 kV, Pulse width=600ns-1 µs, f=15 kHz. The discharge electrode was made from stainless steel and the ground electrode was made from graphite. An air drier (Parker PRD10) supplied dry air to the device. An ozone monitor (Teledyne API 454 Process Ozone Analyzer) was employed to measure the ozone concentration at the exit and the specific energy consumption was calculated. An oscilloscope with high voltage probe was utilized to study the pulse behavior. FIG. 66 presents the exemplary voltage pulses at 85 W power and 5 m$^3$/h air flow rate. The bias voltage for pulse 621 was set at 0 V whereas, the bias voltage for pulse 622 was set at 200V. The streamers ignite at a voltage where the dashed vertical line intersects the trace of the voltage pulse. After the streamer ignition, any further increase in the voltage is not useful. However, any broadening of the pulse tip after the streamer ignition point represents an increase in the amount of useful energy that is utilized in the discharge process. As can be seen, with the application of a bias voltage the pulse tip 622 broadens. This is further illustrated in FIG. 67, which presents the exemplary voltage pulses at 100 W power and 5 m$^3$/h air flow rate. The bias voltage for pulse 631 was 0 V whereas, the bias voltage for pulse 632 was set at 200V. As can be seen, after the streamer ignition, the pulse tip 632 broadened considerably representing a significant increase in the useful energy for discharge. FIG. 68 presents the maximum available power in the discharge space at different bias voltages. As can be seen, the impact of the bias voltage becomes significant after 100 V. The role of the bias voltage is to sweep the space charge from the discharge space between successive pulses, so that the conductivity of the discharge space can be maintained within a predictive range. It is to be noted that the influence of the bias voltage tapers off after certain values (~500V) as well as at high gas flow rates. FIG. 69 presents the availability of maximum power with respect to applied bias voltage at different flow rates. At low rates such as 5-10 m$^3$/h the influence of the bias voltage after 100V is quite significant. On the other hand at 20 m$^3$/h flow rate the change in maximum available power is not as significant as at low flow rates. Higher flow rates move residual charges from the discharge space similar to that of bias voltage. FIG. 70 demonstrates ozone productivity with respect to applied bias voltage at 10 m$^3$/h flow rate. As can be seen, in the absence of a bias voltage 651, it is not possible to put much power (max. 120 W) into the device which yields maximum 4 g/h ozone. On the other hand, at 300V bias voltage 653, it was possible to put 160 W of power into the same device resulting in 8 g/h of ozone. FIG. 71 demonstrates ozone productivity variation with respect to bias voltage at 20 m$^3$/h flow rate. As seen here, when the flow rate was increased to 20 m$^3$/h, even at 0 bias voltage 661, it was possible to put 160 W of power into the same device resulting in 7 g/h ozone. According to the teachings of this disclosure, even at this high flow rates, the bias voltage still has a positive influence and thus enabling 10 g/h ozone production at 180 W power and 200V bias voltage 662. The disclosed bias voltage application technique is particularly beneficial when the moisture content in the air is high and the flow rate is low, thus enabling the operation of the discharge device over a broad range of operational parameters.

3. $C_2H_4$ Removal from Gas Stream

Figure 72:
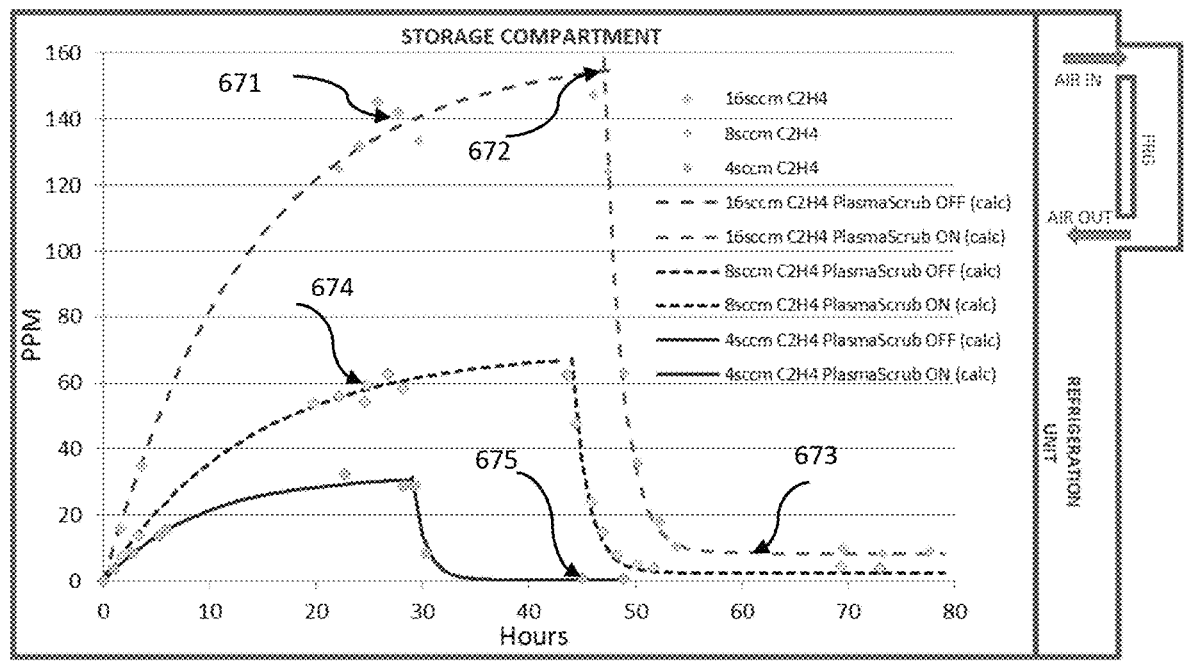
FIG. 72 demonstrates the ethylene build up and removal from a 40 feet reefer container by the discharge device of the present disclosure operating in on and off state.
Figure 73:
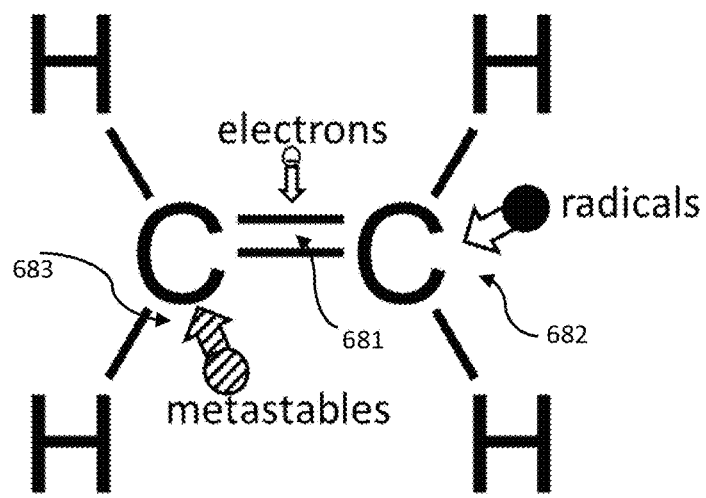
FIG. 73 illustrates the possible mechanisms for ethylene destruction by the discharge device of the present disclosure.
Figure 74:
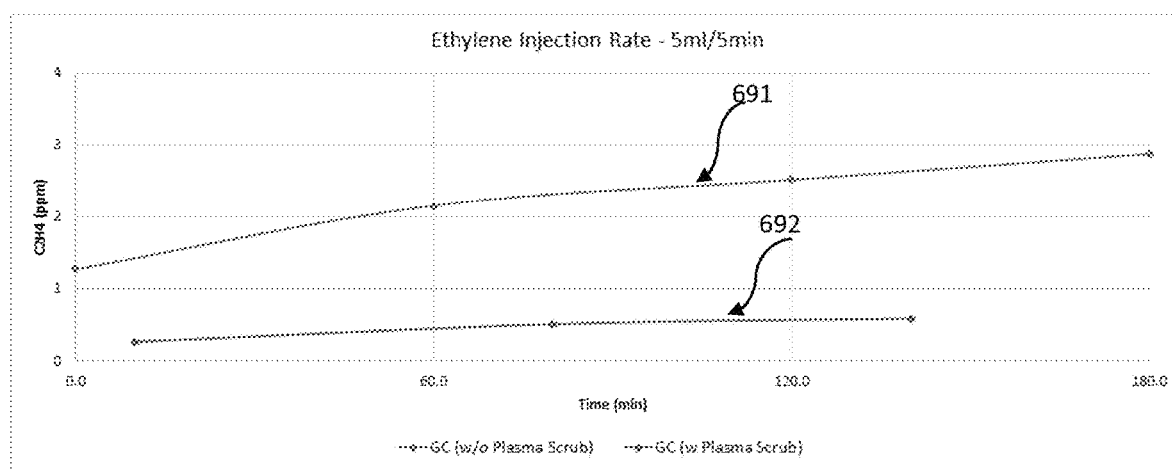
FIG. 74 demonstrates the efficacy of an optional discharge device of the present disclosure in removing ethylene in 40' reefer container at low concentrations.

This example provides an application of the discharge device disclosed herein, for removing ethylene from a fresh produce storage environment. As mentioned earlier, ethylene, a natural plant hormone has many effects such as triggering ripening and senescence. Therefore, removal or destruction of ethylene is a critical requirement to enhance shelf life of fresh produce. To demonstrate this application, six identical devices discussed in Example 2 were installed in a 40 ft refrigerated container that is commonly used for produce transport. The devices were installed through the air exchange port of the container as shown in FIG. 72. Each discharge device was connected to a power supply with the following parameters: $V_{applied}$=−9.5-10.5 kV, Pulse width=600 ns-1 µs, f=15 kHz., with total average power of 700 Wh. The flow rates were maintained at 160 m$^3$/h. The air was drawn into the discharge device from the container and the treated air was released back into the container. The high air circulation rate of the container system ensured fresh supply of ethylene laden air into the discharge device continuously. To simulate a storage environment, synthetic ethylene was injected from a cylinder into the container at a given rate. Further, a humidifier was utilized to maintain the relative humidity level inside the container between 85-90%, which is typical of produce storage environment. The average temperature was maintained at 5° C. An electrochemical sensor (ICA56 sensor) and a gas chromatograph (HP 6890) was used to measure the ethylene content in the air. As shown in FIG. 72, the ethylene level inside the container increased continuously 671, when the discharge device was off. However, when the FRG device was switched on 672, the ethylene concentration started falling down reaching a steady level 673, although fresh ethylene at the rate of 16 sccm was continuously being injected during this time. In other words, the FRG was able to destroy the injected ethylene as well as the accumulated ethylene during this time. Further, it was also observed that the level of ethylene didn't come to zero at 16 sccm feed rate for this device configuration. However, at 4 sccm feed rate, the ethylene level in the container stayed near zero 675. From the experimental measurements (diamond and circle), it was deduced that the ethylene concentration in the container can be mathematically described (the lines) as:

$$\frac{d[C_2H_4]}{dt} = qt - k[C_2H_4];$$

where q is a rate of ethylene production/injection, t is the time and k is a decomposition rate for $C_2H_4$. The parameters q and k depend on the temperature, humidity, flow rate as well as the power. Now referring to FIG. 73, many possible pathways exist for the destruction of ethylene in the discharge space. First, $C_2H_4$ can possibly be dissociated by electrons 681 within the discharge space according to $C_2H_4$ +e$^-$→CH*$_2$+CH*$_2$ and the associated dissociation energy is in the order of 4.5 eV (Szymańska et al.) which overlaps with that of $H_2O$+e$^-$→OH*+H* dissociation. The CH*$_2$ and O* can combine to form $CH_2O$, which further can combine with OH* to form HCOOH (formic acid) and further oxidation of formic acid with OH* can lead to $H_2O$, $CO_2$ and H. Alternatively, the OH* and O* radicals can possibly form other radicals via dehydrogenation process of ethylene according to R—H+O*→R*+OH* and R—H+OH*→R*+ $H_2O$; R* being $C_2H_3$* here. Alternatively, oxidation of R* with $O_2$ can lead to R—O—O (peroxy radical), which upon further oxidation may form $CO_2$ and $H_2O$. Radical chain reactions such as: R—O—O+R—H→ROOH+R* are also possible. The secondary radicals such as $O_3$ and $HO_2$ can also participate in oxidation of $C_2H_4$ forming $CO_2$ and $H_2O$, however, in the presence of the primary radicals, oxidation pathways involving primary radicals will be dominant. It is to be noted that $CO_2$ dissociation energy is around 5.52 eV. Therefore, it is possible that the $CO_2$ byproduct may undergo the dissociation process. The most important reactions are electron impact dissociation into CO and O, electron impact ionization into CO$^+_2$, which recombines with electrons or O$^-_2$ ions into CO and O and/or $O_2$, and electron dissociative attachment into CO and O$^-$. The created CO molecules are relatively stable, but may form other compounds in the discharge space. It is to be noted that certain level of $CO_2$ is beneficial for the storage environment, however, high $CO_2$ level is damaging to many produce. Therefore, using the discharge device disclosed herein, one can effectively remove $C_2H_4$, as well as control $CO_2$ level simultaneously by forming water soluble byproducts which can be easily scrubbed from the gas stream as it passes through the filter attached to the device. Several prior devices have used ozone to oxidize $C_2H_4$ from the storage environment but introduce high levels of $CO_2$ that may not be an effective solution. Further, the introduction of ozone into controlled atmosphere storage where the oxygen is deliberately kept low defeats the purpose of controlled atmosphere. Therefore, the conversion pathways possible in the discharge device enables one to effectively control the ethylene as well as $CO_2$, and thus provides a unique solution. FIG. 74 presents the ethylene level in the container when the injection rate was kept at 1 ml/min and simultaneously two devices were deployed with average power of 200 Wh and flow rate of 30 m³/hour. As can be seen, the power utilized to remove ethylene (w/ppm) is significantly higher at lower concentrations compared to that of required at high concentrations (FIG. 72). This is due to the low collision probability when a fewer ethylene molecules are present in the discharge space and much of the energy is utilized in creating other radicals. Nevertheless, the discharge device can effectively keep the ethylene level at sub ppm level which is critical for many storage environments. Many studies have demonstrated that maintaining the ethylene level at sub ppm level can extend the shelf life considerably. It is to be noted that the ICA56 sensor readings 691 were higher than that of gas chromatograph measurements 692. This is due to the interference of other radicals such as $O_3$ with the ICA56 sensor which operates based on electrochemical principles.

4: Fumigation for Bacterial Spores

Figure 42:
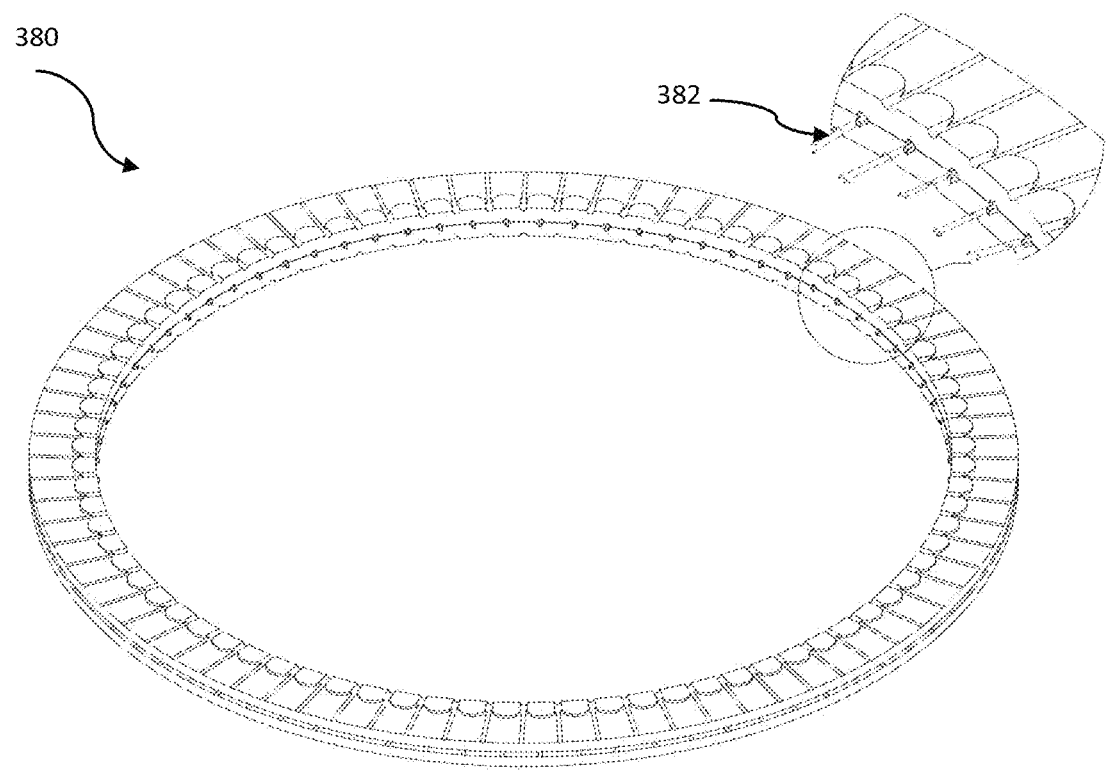
FIG. 42 is a schematic arrangement for disc type discharge electrode having converging discharge pins encapsulated in a cassette to provide airflow around the discharge pins.
Figure 43:
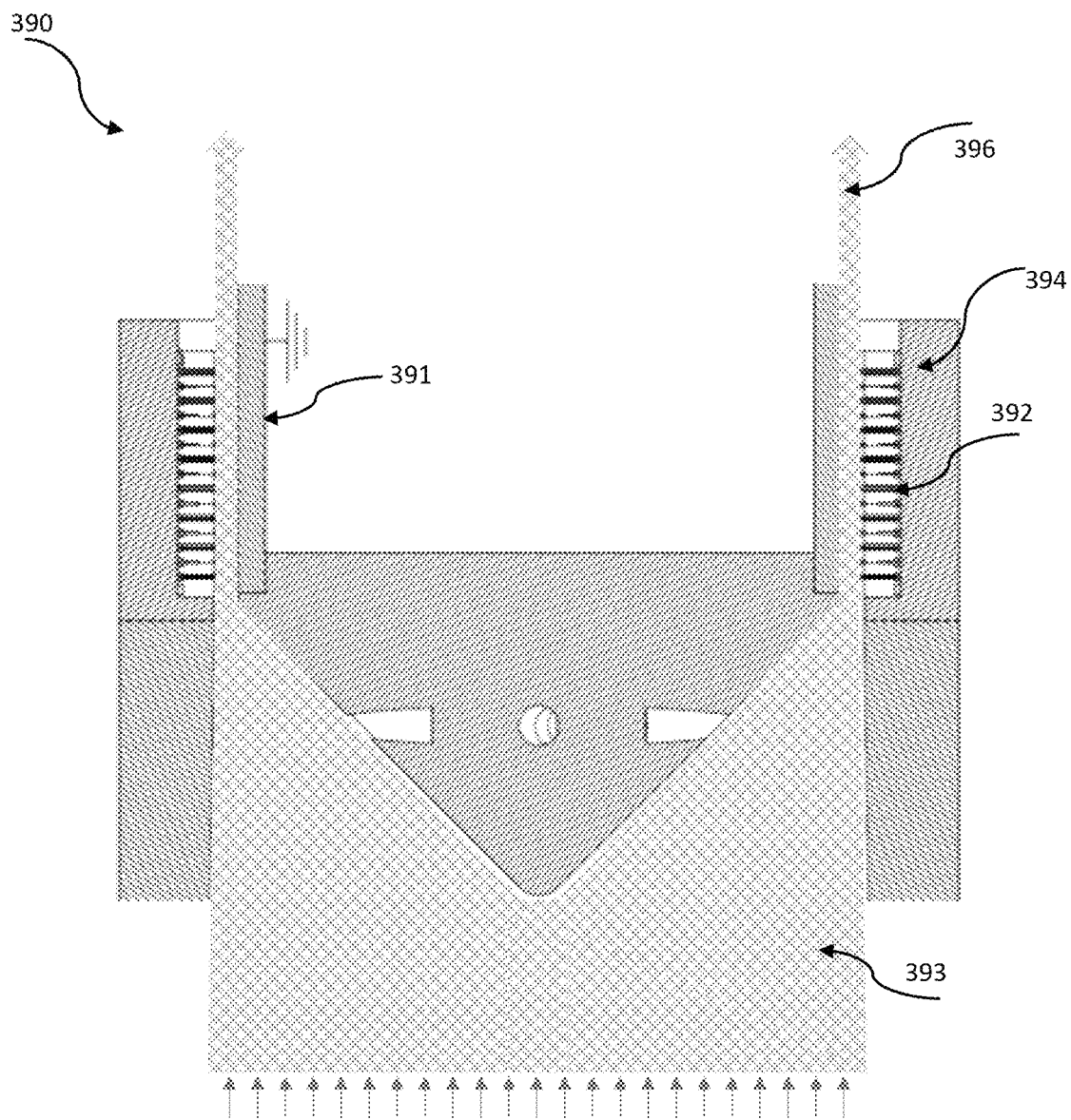
FIG. 43 is a schematic arrangement for a discharge device operating with a gas feed optionally having suspended liquid droplets (or a mist) and converging discharge pins according to the teachings of the present disclosure.
Figure 44:
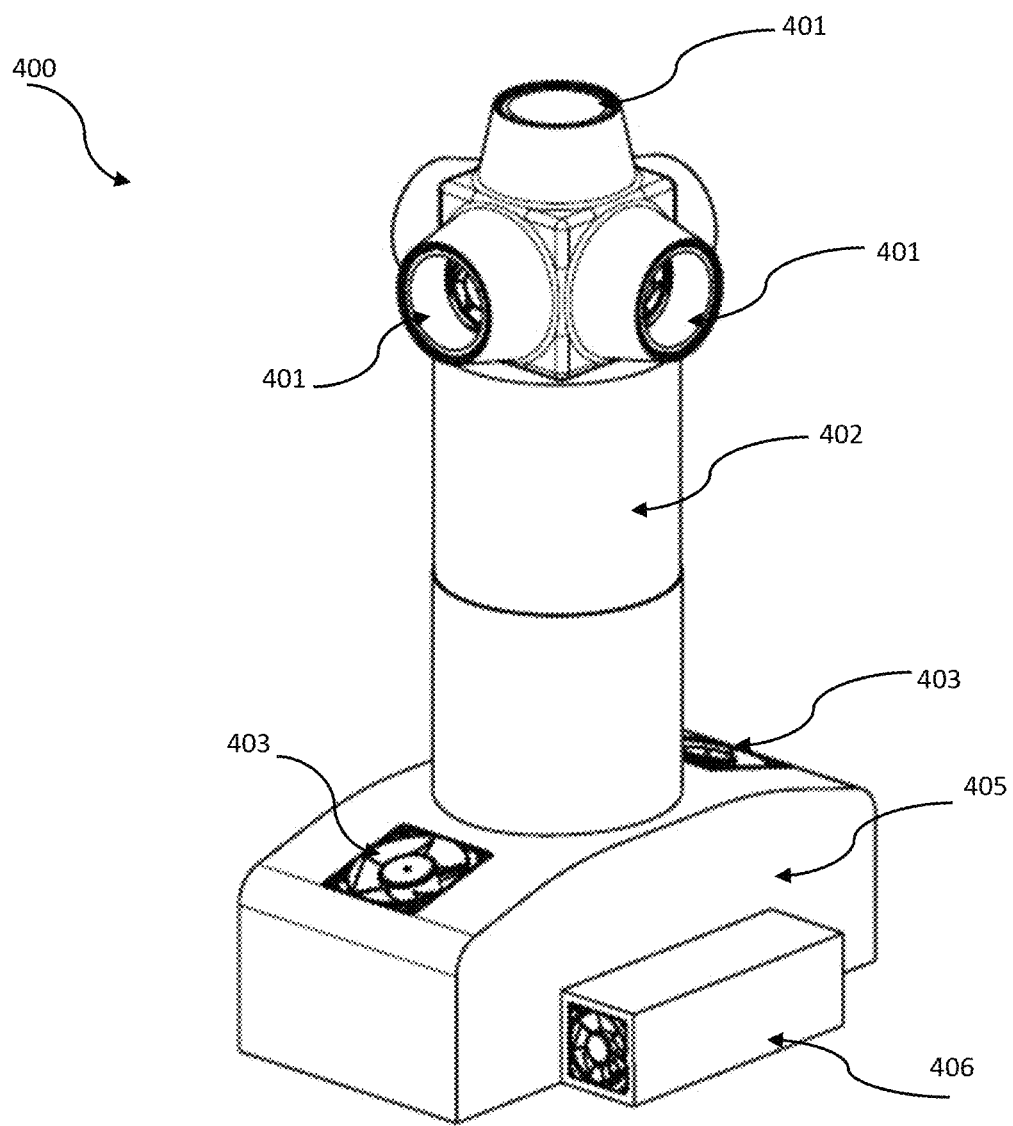
FIG. 44 is a schematic arrangement for a fumigation device optionally having multiple discharge devices operating according to the teachings of the present disclosure and a common gas feed optionally having suspended liquid droplets (or a mist)
Figure 45:
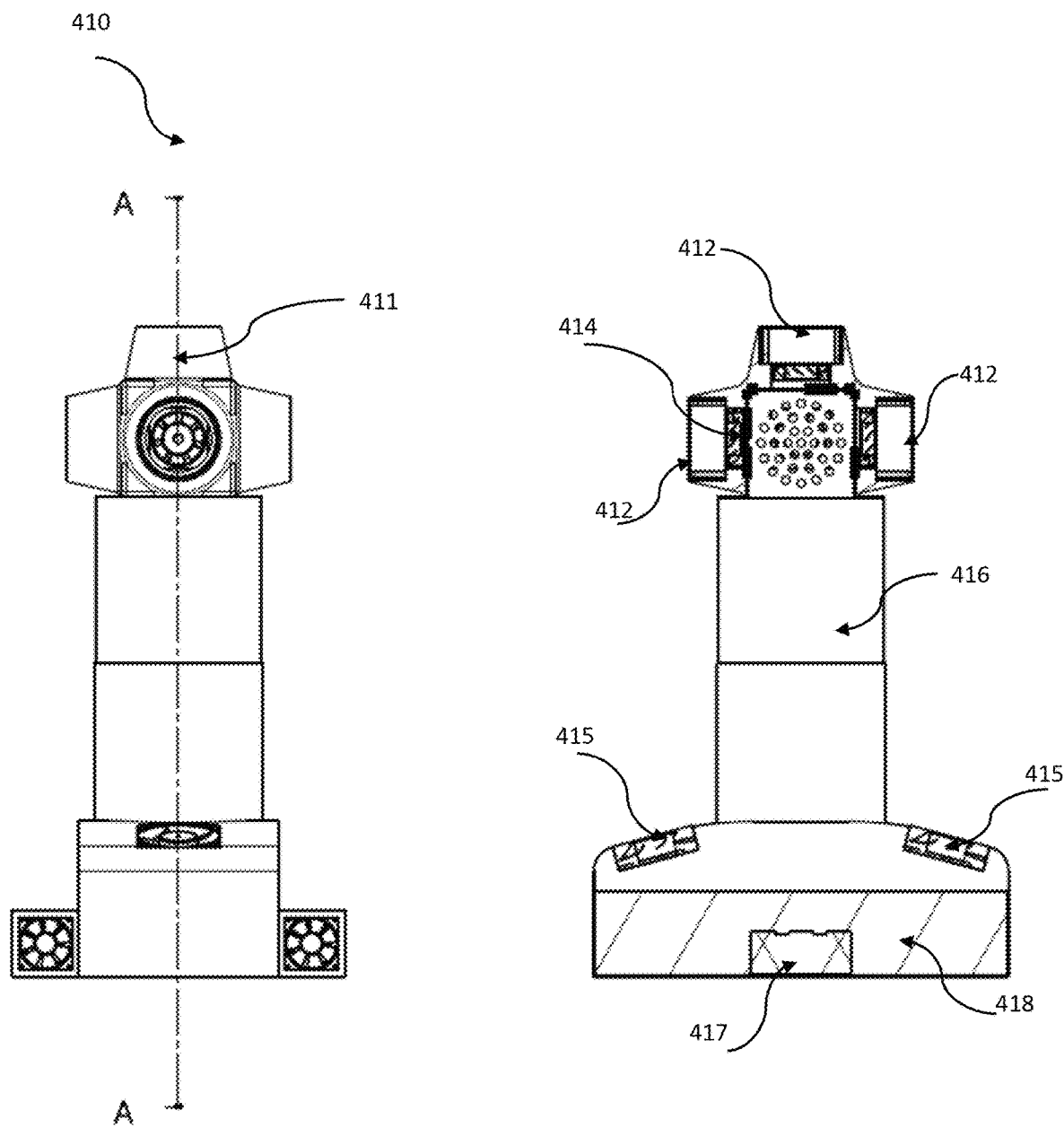
FIG. 45 is a schematic cross section view of the fumigation device shown in FIG. 44.
Figure 46:
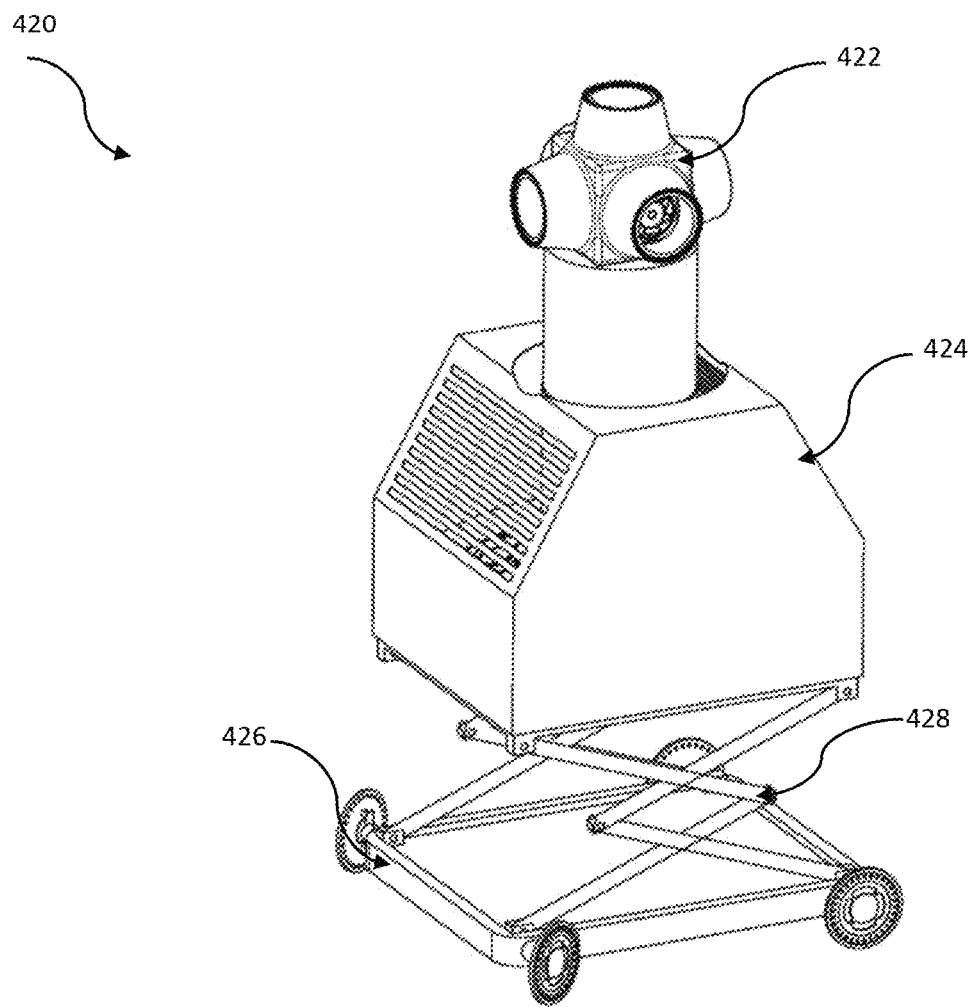
FIG. 46 is a schematic arrangement for a fumigation device operating according to the teachings of the present disclosure and optionally mounted on a mobile and adjustable stage.

This example demonstrates the application of the discharge device in fumigation mode as disclosed here in for sterilization against resistant bacteria spores. A device was assembled according to the descriptions provided in FIG. 43. The device parameters were kept as follows: 19200 (4800 discharge pins, square size=0.25×0.25 mm²) ignition tips, with inter pin distance=2 mm and ignition tip to counter electrode distance=5 mm. The discharge electrodes were encapsulated into cassettes according to FIG. 42 and were connected to negative polarity power supply with the following voltage parameters: $V_{applied}$=−9.5-10.5 kV, Pulse width=600ns-1 µs, f=15 kHz, with an average power of 320 Wh. The discharge electrode was made from stainless steel and the ground electrode was made from graphite. Ambient air at a rate of 30 m3/h was supplied to a chamber that contained water with an ultrasonic fogger which supplied approximately 500 g water per hour. The supplied air picked up the mist from the chamber and then passed through the discharge space as described in FIG. 43.

Initially the device was partially powered by only connecting 1200 discharge pins and the output gas from the discharge device was collected into a cooled chamber to condense the moisture. Chemetrics K-5510 kit (Midland, VA) was used to measure dissolved hydrogen peroxide in 25 ml of condensed moisture. The CHEMets ampule was broken inside the sample cup, which fills up with sample water. Color change is obtained by Ferric thiocyanate method. The ferric thiocyanate method consists of ammonium thiocyanate and ferrous iron in acid solution (contained inside the ampules). Hydrogen peroxide oxidizes ferrous iron to the ferric state, resulting in the formation of a red thiocyanate complex. The resultant red color is compared with the comparator provided. An average of 4 ppm $H_2O_2$ was observed in the sample. The observed $H_2O_2$ in the condensed moisture is a clear indicator of abundant OH* radical formation in the generator. It is possible that $H_2O_2$ may form inside the discharge space, however, the dissociation energy for $H_2O_2$ is in the order of 2.21 eV and will preferably again dissociate to OH* as almost all the gas gaseous stream is directed to interact with the streamers until they exit the discharge space according to the teachings of this invention.

Figure 75:
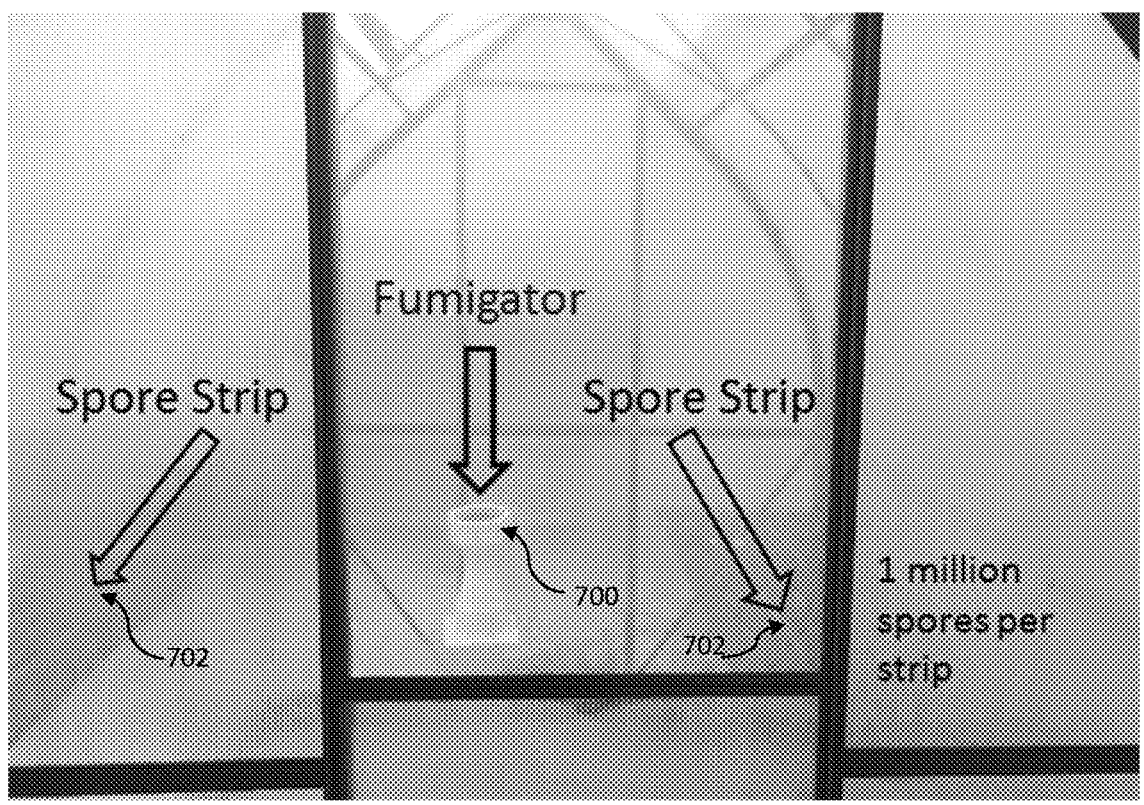
FIG. 75 illustrates an experimental fumigation set up to demonstrate the spore decontamination capability of an optional discharge device of the present disclosure.

The fumigation device was then placed in the middle 700 of a 7'×7'×7' enclosure as shown in FIG. 75. Three types of bacteria spore strips containing 1 million spores per strip were placed at sample location 702. The included bacteria spores were; *Bacillus atrophaeus*, *Bacillus pumilus* and *Geobacillus stearothermophilus*. As observed in FIG. 75, the room was filled with the mist containing radicals. The treatment time was set at 6 hours. It is to be noted that this time is not optimized and it is believed that the optimized time will be much less. The observations and inferences are tabulated in Table 1 below. As can be seen, all the three bacteria spores were completely annihilated by the fumigation process demonstrating the sterilization capability of the process that only utilizes water and electricity. Operation of discharge devices in air with suspended water droplets has traditionally been problematic due to arcing leading to electrode damages. Upon inspection no electrode damage was observed after continuous run for 6 hours a day for a week, demonstrating the benefits of the teachings of this disclosure.

TABLE 1

| S No | Name of spore | Sample description | Culture media | Pre-incubation color | Post incubation color | Inference |
|---|---|---|---|---|---|---|
| 1 | *Bacillus atrophaeus* | No spore strip added | GMBTB tryptic soy broth | Green | Green | Broth media is uncontaminated |
| 2 | *Bacillus atrophaeus* | Untreated *B. atrophaeus* strip added | GMBTB tryptic soy broth | Green | Yellow | Spores are viable |
| 3 | *Bacillus atrophaeus* | Spore strip treated 2 feet from fumigation unit | GMBTB tryptic soy broth | Green | Green | Total annihilation of spores during treatment |
| 4 | *Bacillus pumilus* | No spore strip added | GMBTB tryptic soy broth | Green | Green | Broth media is uncontaminated |
| 5 | *Bacillus pumilus* | Untreated *B. pumilus* strip added | GMBTB tryptic soy broth | Green | Yellow | Spores are viable |
| 6 | *Bacillus pumilus* | Spore strip treated 2 feet from fumigation unit | GMBTB tryptic soy broth | Green | Green | Total annihilation of spores during treatment |
| 7 | *Bacillus pumilus* | Spore strip treated 6 feet from fumigation unit | GMBTB tryptic soy broth | Green | Green | Total annihilation of spores during treatment |

TABLE 1-continued

| S No | Name of spore | Sample description | Culture media | Pre-incubation color | Post incubation color | Inference |
|---|---|---|---|---|---|---|
| 8 | Geobacillus stearothermophilus | No spore strip added | GMBCP tryptic soy broth | Purple | Purple | Broth media is uncontaminated |
| 9 | Geobacillus stearothermophilus | Untreated G. stearothermophilus strip added | GMBCP tryptic soy broth | Purple | Yellow | Spores are viable |
| 10 | Geobacillus stearothermophilus | Spore strip treated 2 feet from fumigation unit | GMBCP tryptic soy broth | Purple | Purple | Total annihilation of spores during treatment |
| 11 | Geobacillus stearothermophilus | Spore strip treated 6 feet from fumigation unit | GMBCP tryptic soy broth | Purple | Purple | Total annihilation of spores during treatment |

5: Discharge Device with Liquid Electrode

Figure 76:
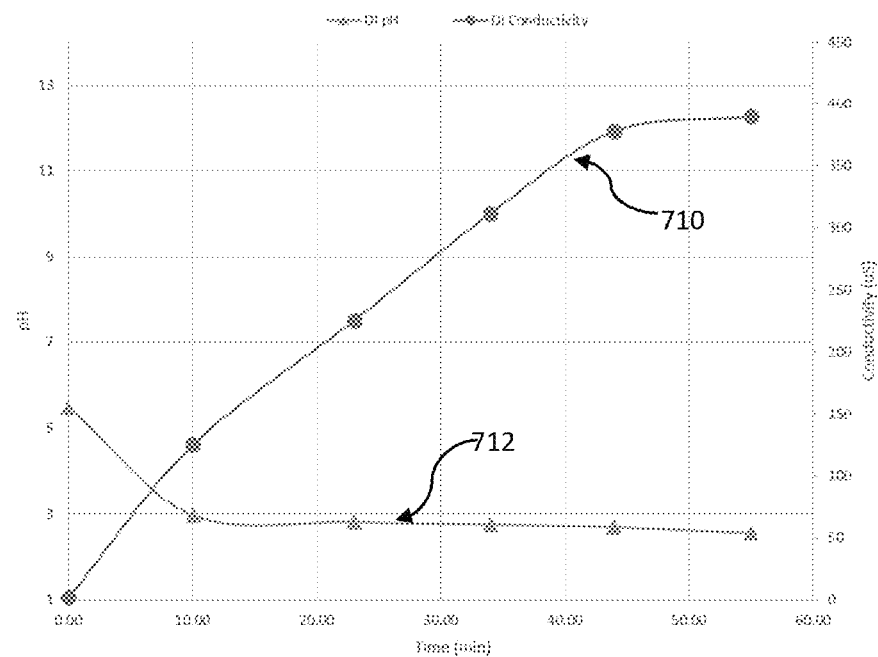
FIG. 76 presents the conductivity and pH change in water due to the discharge device operating with water electrode.
Figure 77:
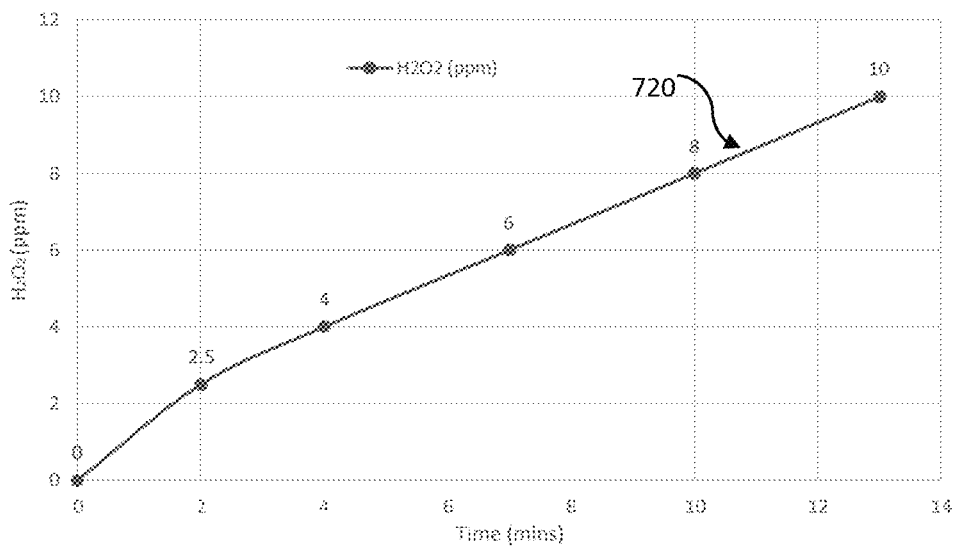
FIG. 77 presents the peroxide formation in water with a water electrode discharge device of the present disclosure.

This example demonstrates the application of the discharge device with liquid electrode for removal of various impurities from water via advanced oxidation process. A device was fabricated according to the descriptions provided in FIG. 56. It comprised of 11520 (2880 discharge pins, square size=0.25×0.25 mm$^2$) ignition tips, with inter pin distance=2.5 mm and ignition tip to counter electrode distance=4.5 mm, arranged on a discharge electrode assembly having diameter of 122 mm and 75 mm height. The discharge electrode was connected to negative polarity with the following voltage parameters: $V_{applied}$=-9.5-10.5 kV, Pulse width=600ns-1 µs, f=15 kHz, with an average power of 320 Wh. The counter electrode here was the film of water flowing over a graphite cylinder. Various experiments were conducted with different impurities mixed into the water. FIG. 76 presents the change in the conductivity and pH of deionized water with respect to treatment time. The water flow through the discharge device was set at 350 ml per min, which was recycled continuously through a 5 gallon reservoir. The power was set at 100 W. As can be seen the conductivity of the water 710 increased considerably as the discharge process continued. The pH 712 on the other dropped considerably in the beginning and then stabilized. The observed conductivity change can only happen due to the creation of dissolved charged species. Many possible species are expected to form such as OH*, O*, $H_2O_2$, $O_3$, NO* and $NO_2$*, and peroxynitrite along with other radicals. FIG. 77 presents the $H_2O_2$ concentration 720 at different treatment times. These primary and secondary radicals can be used beneficially for removing impurities from water as well as for sterilization. Capacitive deionization (CDI) has been recognized as an efficient method for removing dissolved ionic compounds such as salts and heavy metals. However, to operate a CDI cell efficiently, the water must possess good conductivity. Therefore, when the water contains very low level of dissolved ions, CDI cannot run effectively and most of the energy is lost as heat generation. As demonstrated above, the discharge process increases the conductivity significantly and as a result CDI process can be utilized after the discharge to eliminate dissolved ions to make ultrapure water cost effectively.

Figure 78:
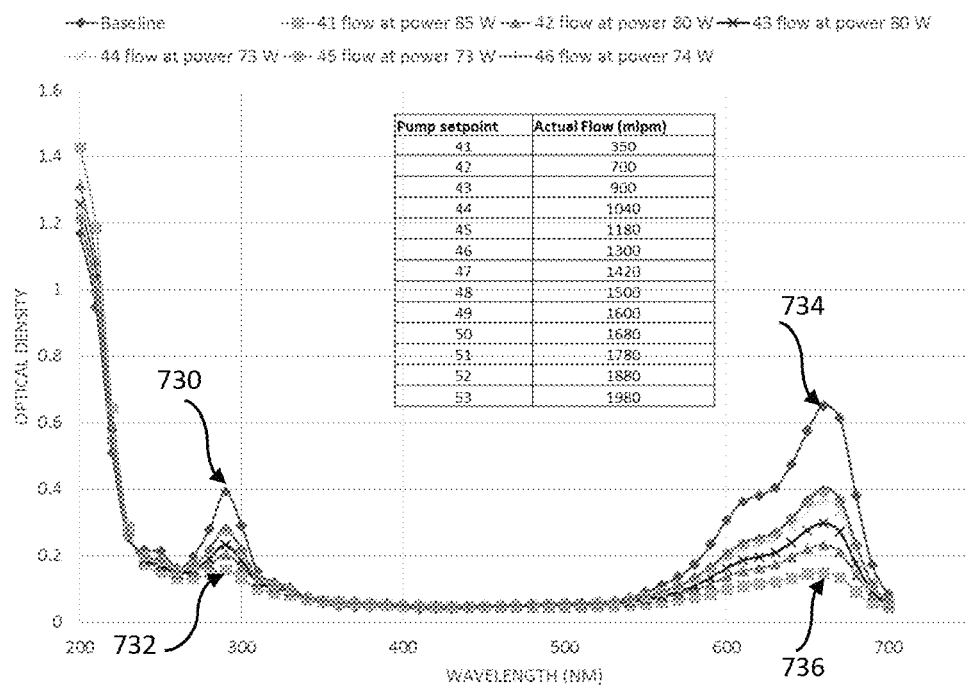
FIG. 78 presents the progression of methylene blue removal from water by water electrode discharge device of the present disclosure.

Now utilizing the discharge device disclosed here, the neutralization/removal of various impurities dissolved in water will be demonstrated. About 15% of the total world production of dyes is lost during the dyeing process and is released as liquid effluents. Color removal from such wastes is one of the most difficult requirements, faced by the textile finishing, dye manufacturing, pulp and paper industries. Among the various types of dye, various cationic dyes, including methylene blue, are used in dye, paint production and wool dyeing. Methylene blue is also used in microbiology, surgery, diagnostics and as a sensitizer in photo-oxidation of organic pollutants. To demonstrate solutions to this environmental problem, a model dye, methylene blue (MB), was dissolved in water and the resulting solution was deployed as the liquid electrode according to the teachings of this disclosure. The level of MB was determined by absorption spectroscopy (BioTek Epoch 2 Microplate Spectrophotometer). FIG. 78 presents the optical density indicating the level of MB in the water. The starting solution optical density is indicated by the highest peaks 730 and 734. Experiments were conducted at various flow rates. As seen the highest removal efficiency indicated by the lowest peaks 732 and 736 was observed at the lowest flow rate 350 ml per min. This demonstrates that with optimized process conditions dyes can be effectively removed from the effluent.

Methyl tertiary-butyl ether (MTBE) is another man-made chemical, used since the nineteen eighties almost exclusively as a fuel additive in gasoline. Because MTBE dissolves easily in water and does not readily bond with soil, finding MTBE in public water systems and private drinking wells is not uncommon. MTBE does not degrade easily in the environment and is resistant to microbial decomposition, and thus it is difficult and costly to remove from ground water. MTBE makes drinking water taste very offensive and gives off an unpleasant odor. MTBE exposure can cause nausea, nose and throat irritation, digestive tract irritation, liver and kidney damage, and nervous system effects including mental confusion. While, MTBE's full effects on human health have not been extensively studied, EPA reports link MTBE exposure to cancer in lab animals and so classify MTBE as a potential carcinogen. Experiments were conducted by dissolving MTBE into water which was used as the liquid electrode as above. The flow rate was maintained at 350 ml/m, and the water was recirculated from a 5 gallon reservoir and the power was set at 100 W. The concentration of MTBE in the water sample was determined according to EPA 524.4 method which utilizes Gas Chromatography/Mass Spectrometry using Nitrogen purge gas. Table 3 presents the MTBE level in the water sample at different times after the treatment. As can be seen a significant reduction in MBTE (1000 µg/L to 180 µg/L) occurs in a single pass through the discharge device. It is to be noted that the desired conversion pathway of MTBE is to convert it to $CO_2$ ensuring that it doesn't form any other harmful compounds. As seen in Table 2, the $CO_2$ level increased corresponding to the reduction in MTBE level. No other intermediate compounds were observed.

TABLE 2

| Sample ID | Sample Description | Dissolved CO2 (ppm) | MTBE Content (µg/L) |
|---|---|---|---|
| 051216B | Baseline Sample. 0.125 ml of MTBE injected into 5 gal of DI water and agitated for mixing | 2.5 | 1000 |
| 051216OP | Sample collected directly under direct plasma reactor - in one pass after baseline | 11.25 | 180 |
| 0512164HR | Sample collected from 5 gal bulk after 4 hours of exposure to direct plasma | 19.5 | 30 |

Figure 79:
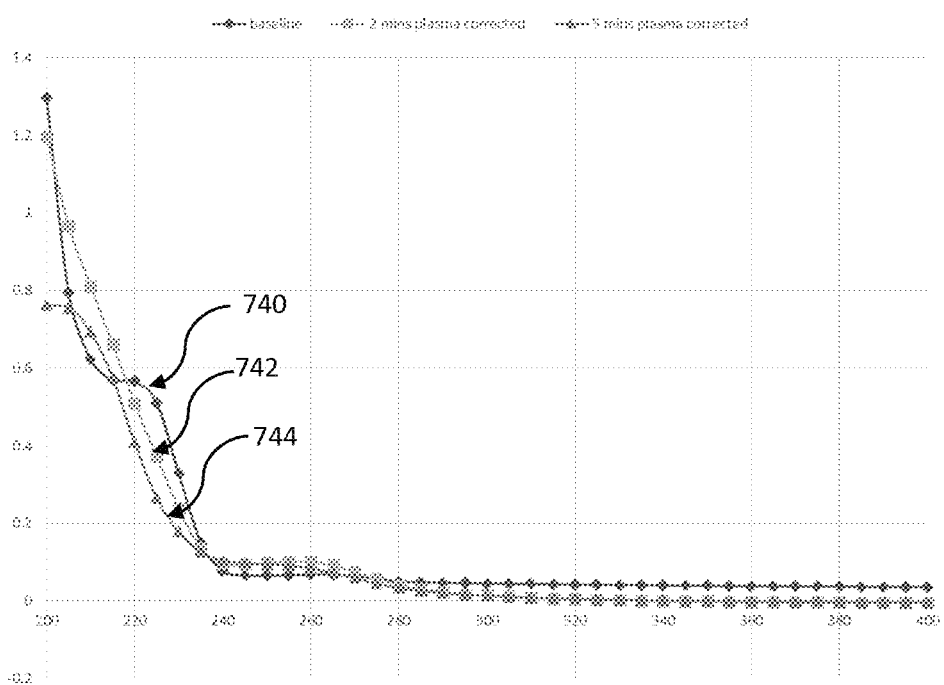
FIG. 79 presents the progression of Ibuprofen removal from water by water electrode discharge device of the present disclosure.

The presence of emerging contaminants in water has become a serious concern. Typical water treatment facilities are not designed to remove pharmaceuticals from drinking water. These drugs, both prescription and over-the-counter, can end up in water supplies. There are many concerns that this is a result of flushing drugs, but many drugs are not completely metabolized by the body, and enter the environment after passing through wastewater treatment facilities. The effluents from such treatment facilities are discharged into bodies of water that can end up in water supplies, from which drinking water is taken. One contaminant in particular that is being found in water is the pharmaceutical ibuprofen. It is a widely administered drug used for the relief of symptoms of arthritis, fever, and to reduce pain. There have been some implications of long-term effects on the ecosystem from ibuprofen by its killing of the species *Lemna minor* as well as negatively impacting fish population. To demonstrate the removal of pharmaceuticals from effluent water, ibuprofen was dissolved into water which was then used as the liquid electrode for the discharge device of the present disclosure. The concentration of ibuprofen was monitored via optical density utilizing an absorption spectrophotometer (BioTek Epoch 2 Microplate Spectrophotometer). The flow rate was maintained at 350 ml/m, and the water was recirculated from a 5 gal reservoir and the power was set at 100 W. FIG. 79 presents the intensity peak relevant to ibuprofen 740 being the highest for the baseline solution. With 5 minutes of treatment, the ibuprofen peak 744 was completely eliminated.

Figure 80:
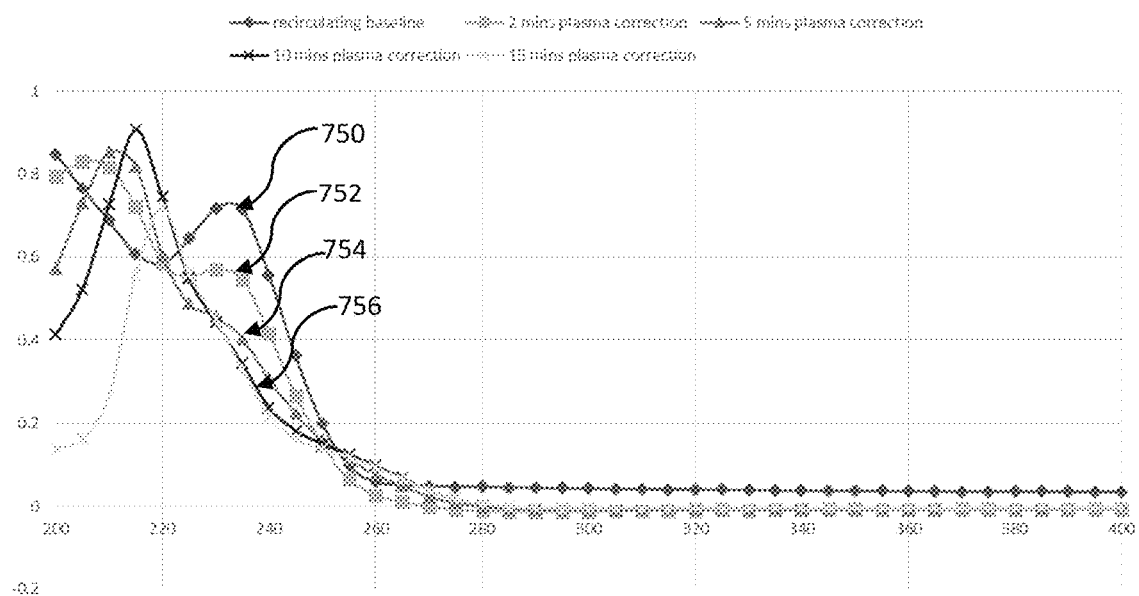
FIG. 80 presents the progression of metformin removal from water by water electrode discharge device of the present disclosure.

The widely prescribed anti-diabetic metformin is among one of the most abundant of pharmaceuticals found in effluent and has been blamed for the occurrence of intersex fish, where male reproductive tissues show evidence of feminization. The disclosed liquid electrode discharge device can be utilized for destroying metformin from water. Commercially available metformin was dissolved in water which was used as the liquid electrode. The flow rate was maintained at 350 ml/m and the water was recirculated from a 5 gal reservoir and the power was set at 100 W. FIG. 80 presents the metformin level as determined by the spectrophotometer. The highest metformin peak 750 is located between 220-240nm wavelength and belongs to the baseline starting solution. After 15 minutes of recirculation the metformin peak 756 had disappeared, demonstrating the ability of destroying metformin from water affluent. Although limited number of pharmaceutical examples have been demonstrated here, the technique disclosed here can be utilized for a wide variety of pharmaceuticals.

Figure 81:
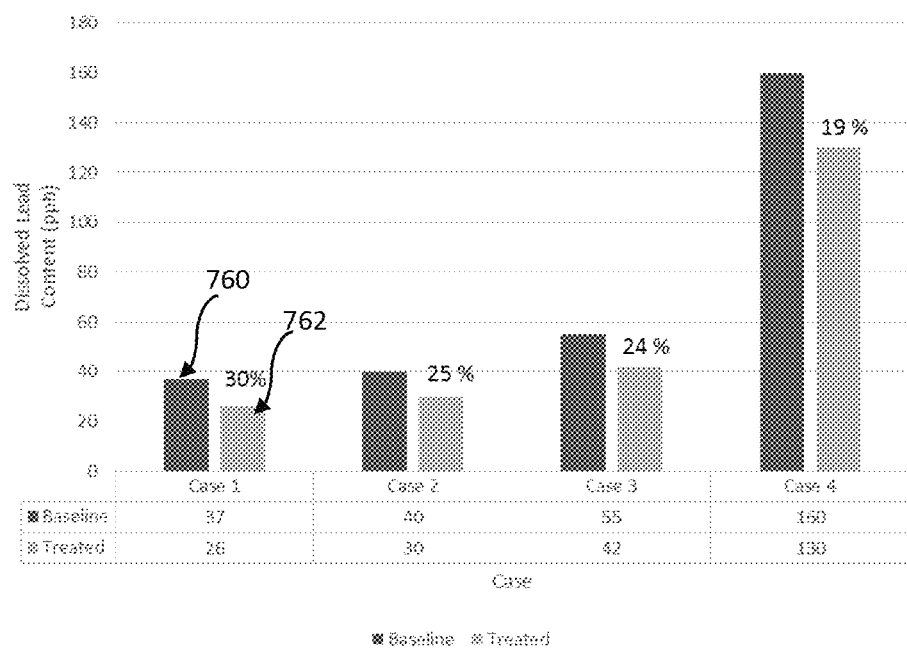
FIG. 81 presents the progression of soluble to insoluble lead (Pb) conversion in water by water electrode discharge device of the present disclosure.

The main threats to human health from heavy metals are associated with exposure to lead, cadmium, mercury and arsenic. Often the exposure occurs though food and drinking water. Metals in our water supply may occur naturally or may be the result of contamination. Naturally occurring metals are dissolved in water when it comes into contact with rock or soil material. Other sources of metal contamination are corrosion of pipes and leakage from waste disposal sites. The heavy metals present in undissolved suspended particulate form can be removed by filtration process. One possible way to remove the dissolved heavy metals is to convert them into undissolved particulates through advanced oxidation process which then can be filtered out. Due to the creation of many complex radicals during the discharge process, it is possible to utilize them to form undissolved heavy metal particulates. To demonstrate this, lead nitrate and acetate were dissolved into water. The dissolved lead concentration was determined by inductively coupled plasma mass spectrometry (ICP-MS) after filtering the solution through a 0.1 micron filter paper to make sure that no undissolved material was left in the solution. The lead contaminated solution was then utilized as the liquid electrode in the discharge device disclosed here. The flow rate was maintained at 350 ml/min and the water was recirculated from a 5 gal reservoir and the power was set at 85 W. The treated water was then filtered through a 0.1 micron filter paper to determine the dissolved lead content. FIG. 81 presents the dissolved lead concentration before and after the discharge process at various concentrations. Note that the reduction in the dissolved lead concentration presented for each case was just after one pass through the discharge device. For example, in case 1 the initial concentration 760 was 37 ppm and after one pass through the discharge device and the filter the concentration 762 was 26 ppm representing a 30% reduction. When the filter was removed from the path the lead concentration didn't change indicating that the undissolved particulates formed during the discharge process contributed to the total concentration. Note that the CDI cell included in the FIG. 56 was not utilized in these experiments. When the CDI cell was powered, the dissolved lead was removed. Table 3 presents the results when the CDI cell was operational with a current of 1 amp. The starting solution had 120 ppm dissolved lead and after 4 circulations, the lead content went to 20 ppm. When the cell was reversed (desorption cycle), it gave back the adsorbed lead into the solution and the lead content went to 87 ppm, indicating that much of the dissolved lead was removed by the CDI process. Note that the output from the desorption cycle needs to be disposed as described earlier. When both the discharge component and the CDI component of the device presented in FIG. 56 are operational together, part of the lead will be removed by advance oxidation process and filtration and part by the CDI process. Most importantly, the conductivity improvement due to the discharge process makes the CDI process run efficiently.

Figure 82:
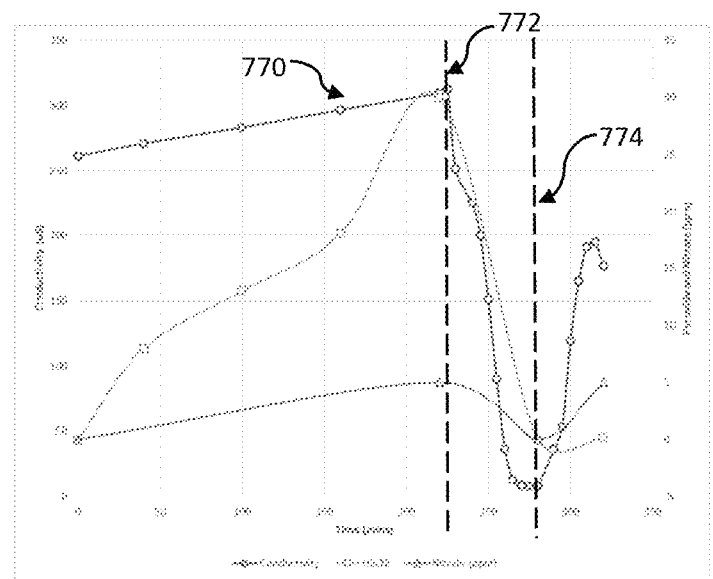
FIG. 82 presents the change in the conductivity, peroxide concentration and nitrate concentration as the with water goes through the discharge space and then through the capacitive deionization cell according to the present disclosure.

Although the discharge process with liquid electrode as disclosed here can remove many impurities, the presence of $H_2O_2$ and nitrates makes the water undrinkable. This has been a known challenge in plasma treated water. Fortunately, the CDI process cures this issue. FIG. 82 presents the conductivity, $H_2O_2$ and nitrate concentration change as the water goes through different process stages. In the discharge stage 770, the conductivity, $H_2O_2$ and nitrate concentration increase considerably. Note that the nitrate comes from the nitrogen in the air as well as dissolved in the water. In the CDI adsorption cycle 772, the conductivity, $H_2O_2$ and nitrate concentration decrease considerably. Further, in desorption cycle 774, the conductivity and nitrate concentration increase again, but the $H_2O_2$ concentration remains low. The $H_2O_2$ once dissociated wasn't expected to be regenerated. Since the output during desorption cycle is discarded, the increased nitrate concentration doesn't pose any health risks.

Thus, the hybrid device disclosed here provides an effective way to treat drinking water, removing a variety of impurities, pharmaceuticals, heavy metals and biologics.

TABLE 3

| Condition | No. Of cycles | Lead Concentration |
|---|---|---|
| Baseline | 0 | 120 ppm |
| Adsorption Cycle | 4 | 20 ppm |
| Desorption Cycle | 2 | 87 ppm |

Figure 83:
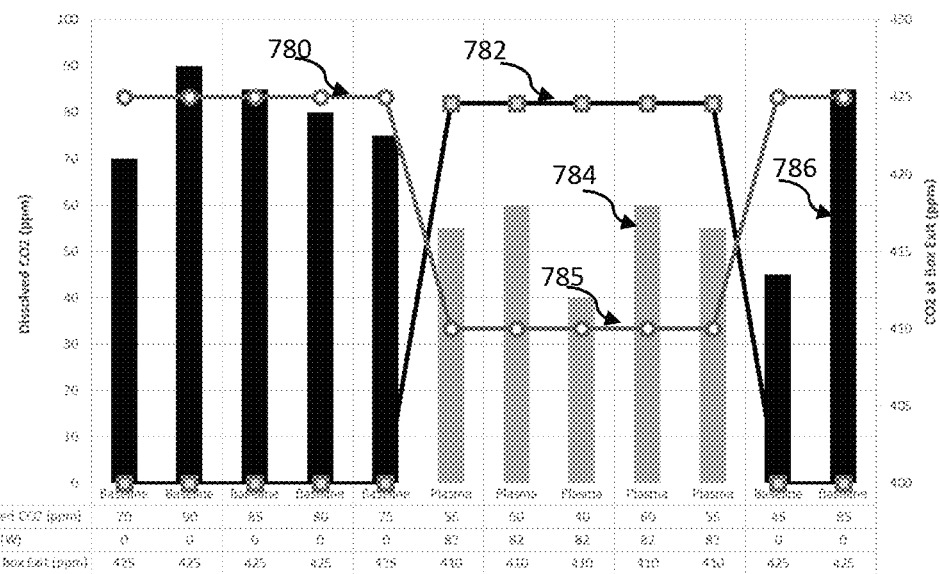
FIG. 83 presents the conversion of $CO_2$ into water soluble byproducts by water electrode discharge device of the present disclosure.

The chemical transformation of carbon dioxide into useful products is becoming increasingly important as $CO_2$ levels in the atmosphere continue to rise as a consequence of human activities. For example, one can produce methanol, methane ($CH_4$), or formic acid (HCOOH) from $CO_2$. Often catalysts along with high pressure chemical reactions are utilized to facilitate the conversion and determine product specificity. Streamer discharge with liquid electrodes as disclosed here can facilitate this conversion cost effectively due to the generation of appropriate radicals. To demonstrate the feasibility, the liquid electrode discharge device discussed above was utilized. $CO_2$ was dissolved into water, which was then used as the liquid electrode. Since it is possible that the dissolved $CO_2$ may escape the water during the discharge process, the device was enclosed in a sealed box having an exit port and the exit gas concentration was measured by pSense Portable $CO_2$ Meter AZ-0001. The dissolved $CO_2$ before and after streamer discharge was also measured by spectrophotometry with an assay kit "KFORM" from Megazyme. FIG. 83 presents the dissolved $CO_2$ measurements as well as $CO_2$ measurement in the exit gas from the box. As seen when the discharge device was not powered, both the $CO_2$ in the exit gas 780 as well as the dissolved $CO_2$ 786 were high. When the discharge device was powered 782, both the dissolved $CO_2$ 784 as well as the $CO_2$ in the exit gas 785 were significantly lower. This demonstrates that the streamer discharge process as disclosed here facilitates the conversion of $CO_2$ into water dissolvable byproducts. The process can be further enhanced with the use of appropriate catalysts to specify the by products such as methanol or formic acid (HCOOH).

While aspects of the invention have been illustrated and described, it is not intended that these aspects illustrate and describe all possible forms of the invention. Rather, the words used in the specification are words of description rather than limitation, and it is understood that various changes may be made without departing from the spirit and scope of the invention.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

REFERENCE LIST

US Patent Documents

| 8857371 B2 | October 2014 | Tabata et al. |
| 5061462 | October 1999 | Suzuki, N. |
| 7724492 B2 | May 2010 | Botvinnik, I. |
| 7042159 B2 | May 2006 | Tanaka et al. |
| 7753994 B2 | July 2010 | Motegi et al. |
| 9132383 B2 | September 2015 | Ursem et al. |
| US 2006/0056130 A1 | March 2006 | Kim et al. |
| US 2013/0177473 A1 | July 2013 | Albrecht et al. |
| US 2015/0179411 A1 | June 2015 | Laux et al. |
| 8293171 B2 | October 2012 | Haven |
| 8388900 B2 | March 2013 | Benedek et al. |
| 6120822 | September 2000 | Denvir et al. |
| 6695953 B1 | February 2004 | Locke et al. |

Non Patent Documents

Szymańska et al., Dissociative electron attachment and dipolar dissociation in ethylene, International Journal of Mass Spectrometry, Vol. 365-366,15 May 2014, Pages 356-364.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular embodiments of the invention, but is not meant to be a limitation upon the practice thereof.

We claim:

1. A free radical generator comprising:
a counter electrode; and
a discharge electrode assembly comprising discharge electrode pins in an array arranged in a radial pattern and electrically configured to receive one or more voltage pulses, wherein each of the discharge electrode pins comprises 3-8 ignition tips, defined by an angle and positioned at a terminus of the discharge electrode pins proximal to the counter electrode, the discharge electrode pins configured such that a field proximity of surrounding streamers constrain a streamer head emitted from adjacent electrode pins of said discharge electrode pins;
wherein the discharge electrode assembly is surrounded by the counter electrode and is separated therefrom by a discharge gap comprising a flow passage, and
at least one end cap electrically isolates the discharge electrode assembly from the counter electrode and permits the flow of gas through the flow passage.

2. The free radical generator of claim 1 wherein the one or more discharge electrode pins comprise 4 to 8 ignition tips.

3. The free radical generator of claim 1, wherein the counter electrode is absent one or more counter electrode pins.

4. The free radical generator of claim 1, wherein each of the one or more discharge electrode pins comprise a tip profile substantially perpendicular to a length of the discharge electrode pin, wherein the tip profile is in the shape of a triangle, a square, a pentagon, a hexagon, a heptagon, or an octagon.

5. The free radical generator of claim 1, wherein the discharge electrode assembly comprises a plurality of rows of the discharge electrode pins extending substantially perpendicular to a length of the discharge electrode array.

6. The free radical generator of claim 5, wherein each subsequent row of discharge electrode pins proceeding in the length of the discharge electrode array is offset from a preceding row.

7. The free radical generator of claim 1, further comprising a gas supply, wherein the at least one end cap comprises an inlet and gas is supplied to the free radical generator such that it flows through the discharge gap.

8. The free radical generator of claim 1, wherein the discharge electrode assembly further comprises:
   a central rod;
   one or more rows of the discharge electrode assemblies, wherein each row of the one or more rows of discharge electrode assemblies comprises a disc having a central hole and the discharge electrode pins extending therefrom; and wherein
   the disc is placed on the central rod to form the array of discharge electrodes.

9. The free radical generator of claim 8, wherein a sixth disc or said one more rows is positioned such that the electrode pins are substantially directly parallel to the electrode pins of a first disc parallel to the length of the central rod.

10. The free radical generator of claim 1, wherein the discharge electrode pins obstruct the flow of gas between the pins.

11. The free radical generator of claim 1, further comprising a bias voltage application circuit, wherein the bias voltage application circuit is configured to apply a bias voltage to the one or more discharge electrodes such that a space charge in the discharge gap is reduced to a negligible level.

12. A process of producing a radical in a fluid comprising:
   passing the fluid through the discharge gap of the free radical generator of claim 1;
   applying a pulse voltage between the discharge electrode pins and the counter electrode, the pulse voltage applied for a pulse time; and
   generating the streamers extending between the discharge electrode pins and the counter electrode, the streamers generating the radical within the fluid.

13. The process of claim 12 wherein the fluid is a gas.

14. The process of claim 13 wherein
   said fluid is a gas, said gas comprises oxygen and nitrogen, the free radical optionally a nitrogen radical or a hydroxyl radical;
   said fluid is a gas, said gas comprising ethylene; or
   said fluid comprises water.

15. The process of claim 12 wherein the pulse voltage is 5 kV to 20 kV.

16. The process of claim 12 further comprising applying a bias voltage between the discharge electrode pins and the counter electrode, the applying between successive voltage pulses.

17. The process of claim 12 wherein a gas velocity is 0.1 m/s to 200 m/s, optionally 5 m/s to 50 m/s.

18. The process of claim 12 further comprising repeating the step of applying and the step of generating, the repeating defined by a pulse width, the pulse width from 10 nanoseconds to 50 microseconds, optionally 400 nanoseconds to 1 microsecond.

19. The process of claim 12 further comprising repeating the step of applying and the step of generating, the repeating defined by a pulse frequency, the pulse frequency from 100 Hz to 100 kHz, optionally 10 kHz to 30 kHz.

* * * * *